US011744853B2

(12) United States Patent
Beal

(10) Patent No.: US 11,744,853 B2
(45) Date of Patent: *Sep. 5, 2023

(54) METHOD OF ADMINISTRATION AND TREATMENT

(71) Applicant: Dyve Biosciences, Inc., Thousand Oaks, CA (US)

(72) Inventor: Ryan Beal, Thousand Oaks, CA (US)

(73) Assignee: Dyve Biosciences, Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/514,653

(22) Filed: Oct. 29, 2021

(65) Prior Publication Data

US 2022/0047624 A1 Feb. 17, 2022

Related U.S. Application Data

(60) Continuation of application No. 17/488,143, filed on Sep. 28, 2021, now abandoned, which is a
(Continued)

(51) Int. Cl.
| | |
|---|---|
| *A61K 33/00* | (2006.01) |
| *A61K 31/198* | (2006.01) |
| *A61K 31/4172* | (2006.01) |
| *A61K 31/133* | (2006.01) |
| *A61K 9/00* | (2006.01) |
| *A61K 35/00* | (2006.01) |
| *A61K 9/16* | (2006.01) |
| *A61K 33/42* | (2006.01) |
| *A61P 35/04* | (2006.01) |
| *A61K 31/704* | (2006.01) |
| *A61K 39/395* | (2006.01) |
| *A61K 31/661* | (2006.01) |
| *A61K 9/06* | (2006.01) |
| *A61K 31/045* | (2006.01) |
| *A61K 31/685* | (2006.01) |
| *A61K 33/30* | (2006.01) |
| *C07K 16/28* | (2006.01) |
| *A61K 9/70* | (2006.01) |
| *A61K 47/02* | (2006.01) |
| *A61K 47/10* | (2017.01) |
| *A61K 47/12* | (2006.01) |

(Continued)

(52) U.S. Cl.
CPC ............ *A61K 33/00* (2013.01); *A61K 9/0014* (2013.01); *A61K 9/06* (2013.01); *A61K 9/16* (2013.01); *A61K 9/7023* (2013.01); *A61K 31/045* (2013.01); *A61K 31/133* (2013.01); *A61K 31/198* (2013.01); *A61K 31/4172* (2013.01); *A61K 31/661* (2013.01); *A61K 31/685* (2013.01); *A61K 31/704* (2013.01); *A61K 33/30* (2013.01); *A61K 33/42* (2013.01); *A61K 35/00* (2013.01); *A61K 39/3955* (2013.01); *A61K 47/02* (2013.01); *A61K 47/10* (2013.01); *A61K 47/12* (2013.01); *A61K 47/14* (2013.01); *A61K 47/183* (2013.01); *A61K 47/22* (2013.01); *A61K 47/24* (2013.01); *A61P 35/04* (2018.01); *C07K 16/2818* (2013.01); *A61K 2039/505* (2013.01); *C07K 2317/76* (2013.01)

(58) Field of Classification Search
CPC .... A61K 33/00; A61K 31/198; A61K 31/133; A61K 9/0014; A61K 35/00; A61K 9/16; A61K 33/42; A61K 35/04; A61K 39/3955; A61K 31/661; A61K 9/06; A61K 31/045; A61K 31/685; A61K 33/30; A61K 9/7023; A61K 47/02; A61K 47/10; A61K 47/12; A61K 47/14; A61K 47/183; A61K 47/22; A61K 47/24; A61K 2039/505; A61P 31/704; C07K 16/2818; C07K 2317/76

See application file for complete search history.

(56) References Cited

U.S. PATENT DOCUMENTS

| | | |
|---|---|---|
| 918,934 A | 4/1909 | Voss |
| 2,802,005 A | 8/1957 | Heidelberger et al. |

(Continued)

FOREIGN PATENT DOCUMENTS

| | | |
|---|---|---|
| AU | 2002335635 B2 | 6/2008 |
| AU | 2008206231 A1 | 7/2008 |

(Continued)

OTHER PUBLICATIONS

Mowat et al. (Ann.rheum. Dis (1976),35,498)).*

(Continued)

*Primary Examiner* — Shirley V Gembeh
(74) *Attorney, Agent, or Firm* — Wilson Sonsini Goodrich & Rosati

(57) ABSTRACT

Provided herein are formulations for topical and/or transdermal administration, and methods of using these formulations for the treatment of proliferative diseases related to cancer such as cancers and related conditions, and solid tumors. Also provided are formulations for topical and/or transdermal administration, and methods of using these formulations for melasma, gout, skin disorders, and other diseases and disorders described herein as well as methods for modulating the pH (e.g. raising) of a tissue or microenvironment proximal to a tumor, modulating pH, or improving the effectiveness of know chemotherapeutic agents, immunotherapy and the like for the prevention, treatment of cancers and related conditions described herein.

20 Claims, 17 Drawing Sheets

Related U.S. Application Data continuation of application No. 17/168,114, filed on Feb. 4, 2021, which is a continuation of application No. 16/866,466, filed on May 4, 2020, now Pat. No. 10,933,088, which is a division of application No. 16/546,256, filed on Aug. 20, 2019, now Pat. No. 10,639,326, which is a division of application No. 16/132,358, filed on Sep. 14, 2018, now abandoned, and a division of application No. 16/132,357, filed on Sep. 14, 2018, now abandoned, said application No. 16/132,358 is a continuation-in-part of application No. PCT/US2018/028017, filed on Apr. 17, 2018.

(60) Provisional application No. 62/639,904, filed on Mar. 7, 2018, provisional application No. 62/609,982, filed on Dec. 22, 2017, provisional application No. 62/562,725, filed on Sep. 25, 2017, provisional application No. 62/559,947, filed on Sep. 18, 2017, provisional application No. 62/559,360, filed on Sep. 15, 2017.

(51) Int. Cl.
*A61K 47/14* (2017.01)
*A61K 47/18* (2017.01)
*A61K 47/22* (2006.01)
*A61K 47/24* (2006.01)
*A61K 39/00* (2006.01)

(56) References Cited

U.S. PATENT DOCUMENTS

| | | | |
|---|---|---|---|
| 3,018,302 A | 1/1962 | Herbert et al. | |
| 3,032,584 A | 5/1962 | Franz et al. | |
| 3,046,301 A | 7/1962 | Phillips et al. | |
| 3,732,340 A | 5/1973 | Arnold et al. | |
| 3,923,785 A | 12/1975 | Ryder et al. | |
| 4,080,325 A | 3/1978 | Ellard | |
| 4,267,173 A | 5/1981 | Draper | |
| 4,474,753 A * | 10/1984 | Haslam | A61K 47/18 514/199 |
| 4,933,184 A | 6/1990 | Tsuk | |
| 5,176,918 A | 1/1993 | Jones | |
| 5,411,750 A | 5/1995 | Lajoie et al. | |
| 5,614,178 A | 3/1997 | Bloom et al. | |
| 5,690,914 A | 11/1997 | Suetsugu et al. | |
| 5,976,556 A | 11/1999 | Norton et al. | |
| 6,069,150 A | 5/2000 | Spinelli et al. | |
| 6,080,751 A | 6/2000 | Stehlin et al. | |
| 6,136,839 A * | 10/2000 | Isakson | A61P 9/08 514/471 |
| 6,569,437 B1 | 5/2003 | Bishop et al. | |
| 6,586,428 B2 | 7/2003 | Geroni et al. | |
| 6,669,951 B2 * | 12/2003 | Rothbard | A61P 27/12 564/243 |
| 7,029,692 B1 | 4/2006 | Bracht | |
| 7,150,975 B2 | 12/2006 | Tamada et al. | |
| 7,592,369 B2 | 9/2009 | Zerangue et al. | |
| 8,697,147 B2 | 4/2014 | Le Fur et al. | |
| 8,895,626 B1 | 11/2014 | Chen et al. | |
| 9,161,963 B2 | 10/2015 | Keller et al. | |
| 9,549,896 B2 | 1/2017 | Crutchley et al. | |
| 9,555,051 B2 | 1/2017 | Mayo et al. | |
| 9,574,001 B2 | 2/2017 | Wisniewski et al. | |
| 10,058,524 B2 | 8/2018 | O'Haimhirgin | |
| 10,076,539 B2 | 9/2018 | Wang | |
| 10,336,710 B2 | 7/2019 | Yang et al. | |
| 10,632,146 B2 | 4/2020 | Beal | |
| 10,639,326 B2 | 5/2020 | Beal | |
| 10,758,490 B2 | 9/2020 | Viladot et al. | |
| 10,933,088 B2 | 3/2021 | Beal | |
| 11,052,152 B2 | 7/2021 | Sand et al. | |
| 11,116,778 B2 | 9/2021 | Gottesman et al. | |
| 2002/0019417 A1 | 2/2002 | Zhang et al. | |
| 2002/0028227 A1 | 3/2002 | Yu et al. | |
| 2002/0034554 A1 | 3/2002 | Hsu et al. | |
| 2003/0059450 A1 | 3/2003 | Maibach et al. | |
| 2003/0099678 A1 | 5/2003 | Maibach et al. | |
| 2003/0104041 A1 | 6/2003 | Hsu et al. | |
| 2003/0129259 A1 | 7/2003 | Mahalingam et al. | |
| 2003/0235543 A1 | 12/2003 | Maibach et al. | |
| 2005/0287089 A1 | 12/2005 | Mahalingam et al. | |
| 2006/0099173 A1 | 5/2006 | Puglia et al. | |
| 2008/0102107 A1 | 5/2008 | Lewellyn et al. | |
| 2009/0042846 A1 | 2/2009 | Gupta | |
| 2009/0053290 A1 | 2/2009 | Sand et al. | |
| 2009/0197825 A1 | 8/2009 | Quart et al. | |
| 2011/0064828 A1 | 3/2011 | Pazoles et al. | |
| 2011/0230551 A1 | 9/2011 | Gunatilaka et al. | |
| 2011/0237527 A1 | 9/2011 | Liu et al. | |
| 2012/0003168 A1 | 1/2012 | Lyga et al. | |
| 2012/0121622 A1 | 5/2012 | Van Nest et al. | |
| 2012/0232152 A1 | 9/2012 | King-Smith et al. | |
| 2012/0277245 A1 | 11/2012 | Gillies et al. | |
| 2012/0282194 A1 | 11/2012 | Florence et al. | |
| 2014/0187599 A1 | 7/2014 | Schafer et al. | |
| 2015/0057361 A1 | 2/2015 | Phanstiel, IV et al. | |
| 2015/0337001 A1 | 11/2015 | Kim et al. | |
| 2016/0051602 A1 | 2/2016 | Chen et al. | |
| 2016/0058723 A1 | 3/2016 | Lee et al. | |
| 2016/0235646 A1 | 8/2016 | Shah et al. | |
| 2016/0235851 A1 | 8/2016 | Sand et al. | |
| 2017/0360827 A1 | 12/2017 | Wang | |
| 2018/0028663 A1 | 2/2018 | Lee et al. | |
| 2018/0156800 A1 | 6/2018 | Lin et al. | |
| 2018/0256471 A1 | 9/2018 | Rinsch et al. | |
| 2018/0297959 A1 | 10/2018 | Yang et al. | |
| 2019/0083386 A1 | 3/2019 | Brunner et al. | |
| 2019/0083527 A1 | 3/2019 | Beal et al. | |
| 2019/0365798 A1 | 12/2019 | Beal | |
| 2020/0030371 A1 | 1/2020 | Beal | |
| 2020/0069805 A1 | 3/2020 | Fikstad et al. | |
| 2020/0108147 A1 | 4/2020 | Muni et al. | |
| 2020/0172909 A1 | 6/2020 | Fitzgerald et al. | |
| 2020/0330506 A1 | 10/2020 | Beal | |
| 2020/0345849 A1 | 11/2020 | Ali et al. | |
| 2020/0390743 A1 | 12/2020 | Ervin et al. | |
| 2021/0007989 A1 | 1/2021 | Garraway et al. | |
| 2021/0015748 A1 | 1/2021 | McCook et al. | |
| 2021/0045998 A1 | 2/2021 | Docherty et al. | |
| 2021/0059755 A1 | 3/2021 | Lam | |
| 2021/0077420 A1 | 3/2021 | Hooper | |
| 2021/0154226 A1 | 5/2021 | Beal | |
| 2021/0228623 A1 | 7/2021 | Beal | |
| 2021/0260001 A1 | 8/2021 | Perricone et al. | |
| 2021/0299020 A1 | 9/2021 | Cruz et al. | |
| 2021/0393655 A1 | 12/2021 | Garraway et al. | |
| 2022/0016158 A1 | 1/2022 | Beal | |
| 2022/0016159 A1 | 1/2022 | Beal | |
| 2022/0023336 A1 | 1/2022 | Beal | |
| 2022/0031612 A1 | 2/2022 | Chen et al. | |
| 2022/0040225 A1 | 2/2022 | Beal | |
| 2022/0062329 A1 | 3/2022 | Beal | |

FOREIGN PATENT DOCUMENTS

| | | |
|---|---|---|
| AU | 2008203281 A1 | 8/2008 |
| AU | 2003284353 B2 | 7/2009 |
| AU | 2017270858 B2 | 9/2019 |
| CA | 2464436 A1 | 4/2003 |
| CA | 2503539 A1 | 5/2004 |
| CA | 2411222 C | 1/2010 |
| CA | 2736117 A1 | 3/2010 |
| CA | 2784899 A1 | 7/2011 |
| CA | 2802692 C | 1/2016 |
| CN | 101897784 A | 12/2010 |
| CN | 103565743 A | 2/2014 |
| CN | 105997979 A | 10/2016 |
| CN | 106236937 A | 12/2016 |
| EP | 1551358 A2 | 7/2005 |
| EP | 1598057 B1 | 4/2012 |
| EP | 2683376 A2 | 1/2014 |

(56) References Cited

FOREIGN PATENT DOCUMENTS

| | | | |
|---|---|---|---|
| EP | 1562531 B1 | 1/2016 | |
| EP | 3002004 A1 | 4/2016 | |
| JP | 2014500867 A | 1/2014 | |
| JP | 2014114291 A | 6/2014 | |
| NZ | 538597 A | 9/2006 | |
| NZ | 579372 A | 2/2012 | |
| WO | WO-9747283 A1 | 12/1997 | |
| WO | WO-03026680 A2 | 4/2003 | |
| WO | WO-03103591 A2 | 12/2003 | |
| WO | WO-2004000259 A1 | 12/2003 | |
| WO | WO-2004037201 A2 | 5/2004 | |
| WO | WO-2008070859 A2 | 6/2008 | |
| WO | WO 2008/083158 | * | 7/2008 |
| WO | WO-2008083158 A2 | 7/2008 | |
| WO | WO-2008105803 A1 | 9/2008 | |
| WO | WO-2009063491 A2 | 5/2009 | |
| WO | WO-2010147899 A1 | 12/2010 | |
| WO | WO-2011041609 A2 | 4/2011 | |
| WO | WO-2011082044 A1 | 7/2011 | |
| WO | WO-2012064429 A2 | 5/2012 | |
| WO | WO-2012133114 A1 | 10/2012 | |
| WO | WO-2014170792 A1 | 10/2014 | |
| WO | WO-2015023926 A1 | 2/2015 | |
| WO | WO-2015123264 A1 | 8/2015 | |
| WO | WO-2016105499 A1 | 6/2016 | |
| WO | WO-2017072668 A1 | 5/2017 | |
| WO | WO-2017095823 A1 | 6/2017 | |
| WO | WO-2017117182 A1 | 7/2017 | |
| WO | WO-2017127834 A1 | 7/2017 | |
| WO | WO-2018162645 A1 | 9/2018 | |
| WO | WO-2018195111 A1 | 10/2018 | |
| WO | WO-2019055880 A2 | 3/2019 | |
| WO | WO-2020028723 A1 | 2/2020 | |
| WO | WO-2020093069 A1 | 5/2020 | |
| WO | WO-2020118113 A1 | 6/2020 | |
| WO | WO-2021167810 A1 | 8/2021 | |
| WO | WO-2021222535 A1 | 11/2021 | |
| WO | WO-2022036051 A1 | 2/2022 | |
| ZA | 200503906 B | 7/2006 | |

OTHER PUBLICATIONS

Babu et al. (Drug delivery 12: 165-169(2005).*
Anonymous: Baking Soda Treatment for Gout, https:222.earthclinic. combaking-soda-for-gout.html XP055765385 (2016).
Bailey et al.: Mechanisms of buffer therapy resistance. Neoplasia. 16(4):354-364 (2014).
Bailey et al., Mechanisms of buffer therapy resistance. Neoplasia 16(4):354-64.e1-3 (2014).
Braunwald et al.: Harrison's Principles of Internal Medicine. 15th Ed., McGraw-Hill, New York, N.Y., pp. 536-544 (2001).
Cuvier et al.: Exposure to hypoxia, glucose starvation and acidosis: effect on invasive capacity of murine tumor cells and correlation with cathepsin (L+B) secretion. Clin Exp Metastasis. 15:19-25 (1997).
Hashim et al.: Reduction of metastasis using a non-volatile buffer. Clin Exp. Metastasis. 28:841-849. (2011) DOI 10.1007/s10585-011-9415-7.
Igel et al.: Recent advances in understanding and managing. F1000Re. 6:247 (2017) doi: 10.12688/f1000research.9402.1. e Collection 2017.
Kruger et al.: Immune based therapies in cancer. Histol. Histopathol v22. 687-696 (2007).
Kunta et al.: Effect of menthol and related terpenes on the percutaneous absorption of propranolol across excised hairless mouse skin. J. Pharm. Sci. 86(12):1369-1373 (1997).
Li et al.: BMJ Open. Diagnosis and treatment for hyperuricaemia and gout: a protocol for a systematic review of clinical practice guidelines and consensus statements. 7:e014928.doi:10.1136/bmjopen-2016-014928 (2017).
N'da, D., Prodrug strategies for enhancing the percutaneous absorption of drugs. Molecules 19:20780-20807 (2014).

PCT/US2018/028017 International Search Report and Written Opinion dated Sep. 7, 2018.
PCT/US2018/051250 International Search Report and Written Opinion dated May 13, 2019.
Ribeiro et al.: J. Nutr Food Sci. 2:6-16 (2013).
Robey et al..: Bicarbonate increases tumor pH and inhibits spontaneous metastases. Cancer Res. 69(6):2260-2268 (2009).
Robey et al.: BioMed Res International. 1-10 (2013).
Robey et al.: BMC Cancer. 11:235-245 (2011).
Robey et al.: J. Integr. Uncol. 4:1-8 (2015).
Rofstad et al.: Acidic extracellular pH promotes experimental metastasis of human melanoma cells in athymic nude mice. Cancer Res. 66:6699-6706 (2006).
Silva et al.: The Potential Role of Systemic Buffers in Reducing Intratumoral Extracellular pH and Acid-Mediated Invasion. Cancer Res. 69(6):2677-2684 (2009).
Topical Edge (2018).
Turner: Increased release of tumour cells by collagenase at acid pH: A possible mechanism for metastasis. Experientia. 35:1657-1658 (1979).
U.S. Appl. No. 16/132,357 Office Action dated Feb. 6, 2020.
U.S. Appl. No. 16/132,357 Office Action dated Oct. 9, 2020.
U.S. Appl. No. 16/132,358 Office Action dated May 29, 2019.
U.S. Appl. No. 16/546,256 Office Action dated Sep. 24, 2019.
U.S. Appl. No. 16/546,260 Office Action dated Oct. 28, 2019.
U.S. Appl. No. 16/866,466 Notice of Allowance dated Oct. 22, 2020.
Vavrova et al., Biodegradable derivatives of tranexamic acid as transdermal permeation enhancers. J Control Release 104(1):41-49 (2005).
Verdolini et al.: Old fashioned sodium bicarbonate baths for the treatment of psoriasis in the era of futuristic biologies: An old ally to be rescued. Journal of Dermatological Treatment. UK. 16(1):26-29 (2005) XP055765406.
U.S. Appl. No. 17/488,132 Office Action dated Nov. 9, 2021.
ASHBY: pH studies in human malignant tumours. Lancet. 2:312-315 (1966).
Australian Application No. 2018255294 First Examination Report dated Apr. 22, 2022.
Dong et al.: Acidosis activation of the proton-sensing GPR4 receptor stimulates vascular endothelial cell inflammatory responses revealed by transcriptome analysis. PLoS One. 8:e61991 (2013).
Dvorak: Tumors: wounds that do not heal. Similarities between tumor stroma generation and wound healing. N Engl J Med. 315:1650-1659 (1986).
Frothingham, Scott: Baking Soda for Gout: Is it Effective. 11 pages. www.healthline.com-health-baking-soda-for-gout Feb. 2019.
Gillies et al.: Bicarbonate for Tumor Related Pain. ClinicalTrials gov NCT01350583 (2011).
Hussain et al., Development of a novel ketoprofen transdermal patch: effect of almond oil as penetration enhancers on in-vitro and ex-vivo penetration of ketoprofen through rabbit skin. Pak J Pharm Sci. 25(1):227-232 (2012).
Japanese Patent Application No. 2020-506134 Notice of Rejection dated May 10, 2022.
Maeda et al.: Topical trans-4-aminomethylcyclohexanecarboxylic acid prevents ultraviolet radiation-induced pigmentation. J. Photochem. Photobiol. B. 47:136-141 (1998).
Manosroi et al.: Stability and release of topical tranexamic acid liposome formulations. J. Cosmet. Sci. 53:375-386 (2002).
Pilon-Thomas et al.: Neutralization of Tumor Acidity Improves Antitumor Responses to Immunotherapy. Canceres.aacrjournals. org. pp. 1381-1392 DOI: 10.1158/0008-5472.CAN-15-1743 (2015).
Springett et al.: Gem-TABS in Unresectable Pancreatic Cancer. ClinicalTrials gov NCT01198821 (2010).
U.S. Appl. No. 17/488,143 Final Office Action dated Mar. 24, 2022.
U.S. Appl. No. 17/488,143 Office Action dated Dec. 3, 2021.
U.S. Appl. No. 17/488,154 Final Office Action dated Mar. 29, 2022.
U.S. Appl. No. 17/488,154 Office Action dated Dec. 15, 2021.
U.S. Appl. No. 17/488,132 Notice of Allowance dated Mar. 15, 2022.
U.S. Appl. No. 17/497,794 Office Action dated Feb. 11, 2022.
U.S. Appl. No. 17/497,794 Office Action dated Mar. 15, 2022.

(56) References Cited

OTHER PUBLICATIONS

U.S. Appl. No. 17/497,799 Office Action dated Jan. 20, 2022.
Ye et al.: Synergistic Transcutaneous Immunotherapy Enhances Antitumor Immune Responses through Delivery of Checkpoint Inhibitors. ACS Nano 10(9):8956-8963 (2016).

* cited by examiner

METHOD OF ADMINISTRATION AND TREATMENT

CROSS-REFERENCE TO RELATED APPLICATIONS

This application is a continuation of U.S. Ser. No. 17/448,143, filed Sep. 28, 2021. U.S. Ser. No. 17/448,143 is a continuation of U.S. Ser. No. 17/168,114, filed Feb. 4, 2021. U.S. Ser. No. 17/168,114 is a continuation of U.S. Ser. No. 16/866,466, filed May 4, 2020 and issued as U.S. Pat. No. 10,933,088 on Mar. 3, 2021. U.S. Ser. No. 16/866,466 is a divisional of U.S. Ser. No. 16/546,256, filed Aug. 20, 2019 and issued as U.S. Pat. No. 10,639,326 on May 5, 2020. U.S. Ser. No. 16/546,256 is a divisional of U.S. Ser. No. 16/132,358, filed Sep. 14, 2018 and a divisional of U.S. Ser. No. 16/132,357, filed Sep. 14, 2018. U.S. Ser. No. 16/132,358 and U.S. Ser. No. 16/132,357 are each a Continuation in-part of PCT/US18/28017 filed Apr. 17, 2018. PCT/US18/28017 claims priority to U.S. 62/559,360 filed Sep. 15, 2017; U.S. 62/559,947 filed Sep. 18, 2017, U.S. 62/562,725 filed Sep. 25, 2017; U.S. 62/609,982 filed Dec. 22, 2017; and U.S. 62/639,904 filed Mar. 7, 2018. Each of the aforementioned patent applications is incorporated by reference in its entirety.

FIELD OF INVENTION

This invention relates generally to methods of treatment and therapeutic uses for enhanced formulations for transdermal or topical delivery of therapeutic agents.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

Progression to metastasis remains the highest mortality risk for cancer patients, despite significant efforts to therapeutically target metastatic lesions. Tumor invasion and metastasis associated with neoplastic progression are the major causes of cancer deaths and understanding the mechanisms determining metastatic spread of malignant cells via invasion to distant tissues is, perhaps, the central question in oncology.

It is known that microenvironmental acidosis in a primary tumor increases cellular motility and invasiveness, leading to increased metastasis and that solid tumors exist in a microenvironment of relatively low pH, presumably because of the hypoxic nature of such tumors, increased glycolytic metabolism of glucose and poor perfusion. As early as 1979, Turner, G A, Experientia (1979) 35:1657-1658 reported that acid pH encouraged the release of tumor cells by collagenase, thus encouraging metastases. Curvier, C. et al., Clin. Exp Metastasis (1997) 15:19-25 reported enhanced invasive capacity of tumor cells due to glucose starvation, hypoxia and acidosis. Rofstad, E. K. et al., Cancer Res (2006) 66:6699-6706 reported that the acidic extracellular pH of human melanoma cells promoted metastasis in mice.

The extracellular pH of malignant solid tumors is acidic, in the range of 6.5 to 6.9, whereas the pH of normal tissues is significantly more alkaline, 7.2 to 7.5. These observations have led to the "acid-mediated invasion hypothesis," wherein tumor-derived acid facilitates tumor invasion by promoting normal cell death and extracellular matrix (ECM) degradation of the parenchyma surrounding growing tumors.

According to miscellaneous sources in the popular press, certain physicians have experimented with intravenous sodium bicarbonate as a method of inhibiting metastatic cancer. A series of articles by Robey, I. F. et al., beginning with a publication in Cancer Res (2009) 69:2260-2267 demonstrated that oral bicarbonate reduces the formation of spontaneous metastases in mouse models of metastatic breast cancer. Additional publications such as Robey, I. F. et al., BMC Cancer (2011) 11:235-245 and Robey, I. F., et al. BioMed Res International (2013) pages 1-10 and Robey, I. F. et al., J. Integr. Uncol. (2015) 4:1-8 described oral administration of bicarbonate as an inhibitor of metastases first in mice, and then in human volunteers. Ribeiro, M. de L., et al., J. Nutr Food Sci (2013) 2:6-16 assigned various pH scores to foods (including wine) and also described oral administration of lysine buffer and bicarbonate in mice bearing prostate cancer. In addition, Silva, A. S. et al., Cancer Res (2009) 2677-2684 described the role of systemic buffers in reducing metastases. Sircus, M. published a book, Sodium Bicarbonate: Nature's Unique First Aid Remedy, Garden City Park, N.Y.: Square One Publishers, 2014, advocating sodium bicarbonate as a remedy for various conditions.

Thus, the idea of using buffers to modulate the pH of the tissues surrounding tumors is not a new concept, however in practice it has failed. A primary reason for this failure is that oral and conventional administration of buffers has serious limitations in practice—specifically intolerance and side effects including diarrhea, gastric intolerance, nausea, vomiting and abdominal discomfort. Therapeutically effective amounts of pharmaceutical formulations comprising pH modulating buffers and the like cannot be administered, delivered, and tolerated orally. Intravenous i.e. systemic administration has also been discredited. Also, it is not clear what cancers would respond to an adjustment of microenvironmental pH and what buffers would be effective. The possibility that other metabolic processes, pathways and mechanisms of action, and the like that are ancillary or independent of adjusting the microenvironmental pH may be involved warrants further study and development.

New treatments, formulations and methods of administration of buffers (e.g. sodium bicarbonate and others) need to be developed that overcome the current deficiencies in such buffering formulations in order to determine the efficacy of various buffering formulations on the treatment of cancer, gout, immunological disorders, skin disorders, and other diseases and disorders described herein. For example, also needed are buffering formulations for topical administration and methods to inhibit cancer or prevent the metastasis, intravasion, invasion, and the growth of cancer cells or tumors. Also lacking in the art are effective buffering formulations and methods for topical administration for the prevention of cancers, for maintaining remission, and for palliative care. Another area that the inventors believe is unmet is formulations of one or more buffering agent and methods of use in combination with other agents or treatments such as chemotherapeutics, immunotherapeutics, or other bioactive agents or Biologics such as antibody-based therapies or therapeutics. The inventions described herein address these unmet needs.

In another aspect of the invention, new treatments, formulations and methods of administration of buffers (e.g. sodium bicarbonate and others) need to be developed for the treatment of gout/hyperuricaemia. Gout is a major health problem worldwide, with the prevalence varying from 0.1% to 10% in different regions. A National Health and Nutrition Examination Survey 2007-2008 showed that among adults aged over 20 years in the United States, 3.9% had self-reported gout, while only 2.9% of the population reported gout in the 1988-1994 survey. In mainland China, a systematic review of data from 2000 to 2014 suggested the prevalence of hyperuricaemia and gout in the general population were 13.3% and 1.1%, respectively. In general, both developed and developing countries presented with increasing prevalence and incidence of gout in recent decades. Patients with hyperuricaemia or gout are at risk of developing a variety of comorbidities, such as hypertension, chronic kidney disease, cardiovascular diseases, metabolic syndromes and psychiatric disorders. A recent survey found that 5%-10% of patients with gout had at least seven comorbidities and that hypertension was presented in at least 74% patients with gout. Li nQ., Li X., Kwong J. S-W. et al., BMJ Open, 2017, 7:e014928. doi:10.1136/bmjopen-2016-014928. Unfortunately, gout remains under-diagnosed and under-treated in the general community. Despite major advances in treatment strategies, as many as 90% of patients with gout are poorly controlled or improperly managed and their hyperuricemia and recurrent flares continue. Igel., T. F., et al., Recent advances in understanding and managing gout, F1000Res., 2017 Mar. 10; 6:247. doi: 10.12688/f1000research.9402.1. e Collection 2017. Thus, it appears that current treatment approaches have failed to make an impact on the treatment of gout. Further inventions described herein address this unmet need.

SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

Applicants have found that the drawbacks of intravenous and oral administration of buffers and other anti-metastatic agents can be overcome by administering these agents topically and/or transdermally, but other types of administration are possible, including for example, intranasally or via transmembrane administration for example by suppository or intranasal application.

Accordingly, in one aspect a method of treating a proliferative disorder associated with cancer in a patient is provided. In some embodiments the method comprises administering topically and/or transdermally an effective amount of a formulation for transdermal delivery comprising one or more buffering agent to a patient in need thereof, where the administration is effective to i) inhibit or prevent the growth of a tumor or tumor cells, ii) inhibit or prevent the metastasis of tumors or cancer cells, iii) inhibit or prevents carcinogenesis, iv) inhibit or prevent the intravasation of tumor cells, or v) improve or extend the duration of remission, or maintain remission of a cancer or tumor.

A proliferative disorder associated with cancer may include any condition, disease, disorder, cellular or metabolic state that is associated with carcinogenesis or a cancer, tumor, cancer cells, or the like. In certain embodiments, treating a proliferative disorder inhibits or prevents the growth of a tumor or tumor cells. In certain embodiments, treating a proliferative disorder inhibits or prevents the metastasis of tumors or cancer cells. In certain embodiments, treating a proliferative disorder inhibits or prevents carcinogenesis. In certain embodiments, treating a proliferative disorder inhibits or prevents the intravasation of tumor cells. In certain embodiments, treating a proliferative disorder improves or extends the duration of remission or maintains remission of a cancer or tumor.

In one aspect, a method of treating cancer in a patient is provided comprising administering topically and/or transdermally an effective amount of a formulation comprising one or more buffering agent to a patient in need thereof, where the administration is effective to inhibit or prevent the growth of a tumor or tumor cells.

In one aspect, a method of preventing or inhibiting the metastasis of tumors is provided comprising administering topically and/or transdermally an effective amount of a formulation comprising one or more buffering agent to a patient in need thereof, where the administration is effective to inhibit or prevents the metastasis of tumors or cancer cells.

In one aspect, a method of preventing the intravasation of tumor cells is provided comprising administering topically and/or transdermally an effective amount of a formulation comprising one or more buffering agent to a patient in need thereof, where the administration is effective to inhibit or prevent the intravasation of tumor cells.

In another aspect, a method of improving, extending the duration of remission, or maintaining remission of a cancer or tumor is provided comprising administering topically and/or transdermally an effective amount of a formulation comprising one or more buffering agent to a patient in need thereof, where the administration is effective in improving, extending the duration of remission, or maintaining remission of a cancer or tumor.

In another aspect, a method of preventing carcinogenesis is provided comprising administering topically and/or transdermally an effective amount of a formulation comprising one or more buffering agent to a patient in need thereof, where the administration is effective to inhibit or prevent carcinogenesis. In another aspect, embodiments are provided herein for preventing or inhibiting carcinogenesis that include the administration of another anti-cancer agent. An exemplary embodiment of this aspect is a method of preventing or inhibiting carcinogenesis comprising i) selecting a therapeutic agent (e.g. a biological agent, chemotherapeutic or immunotherapeutic agent), ii) formulating the therapeutic agent in a suitable formulation, iii) administering the formulation comprising the therapeutic agent, and iv) before, during or after step iii), administering a formulation comprising one or more buffering agent topically and/or transdermally in an amount effective to inhibit or prevent carcinogenesis.

In another aspect, a method of maintaining remission of a cancer is provided comprising administering topically and/or transdermally an effective amount of a formulation comprising one or more buffering agent to a patient in need thereof, where the administration is effective to maintain remission. In another aspect, embodiments are provided herein for maintaining remission that include the administration of other agents (e.g. an anti-cancer agent). An exemplary embodiment of this aspect is a method of maintaining remission of a cancer comprising i) selecting a therapeutic agent (e.g. a biological agent, chemotherapeutic or immunotherapeutic agent), ii) formulating the therapeutic agent in a suitable formulation, iii) administering the formulation comprising the therapeutic agent, and iv) before, during or after step iii), administering a formulation comprising one or more buffering agent topically and/or transdermally in an amount effective to maintain remission of a cancer.

In another aspect, a method of treating cancer in a patient is provided where an effective amount of a formulation comprising one or more buffering agent is administering topically and/or transdermally to a patient in need thereof such that the administration is effective to alter the pH of a tissue or microenvironment proximal to a solid tumor or cancer cells in the patient. In certain embodiments, the change in the pH of a tissue or microenvironment proximal to a solid tumor or cancer cells inhibits the growth of said solid tumor or cancer cells.

In another aspect, a method of altering the pH of a tissue or microenvironment proximal to a solid tumor or cancer cells in a patient is provided where an effective amount of a formulation comprising one or more buffering agent is administering topically and/or transdermally to a patient in need thereof such that the administration is effective to alter the pH of a tissue or microenvironment proximal to a solid tumor or cancer cells in the patient.

In another aspect, a method of preventing metastasis of tumors is provided where an effective amount of a formulation comprising one or more buffering agent is administering topically and/or transdermally to a patient in need thereof such that the administration is effective to alter the pH of a tissue or microenvironment proximal to a solid tumor or cancer cells in the patient and the change in the pH of a tissue or microenvironment proximal to a solid tumor or cancer cells inhibits or prevents the metastasis of tumors or cancer cells.

In another aspect, a method of preventing the intravasation of tumor cells is provided where an effective amount of a formulation comprising one or more buffering agent is administering topically and/or transdermally to a patient in need thereof such that the administration is effective to alter the pH of a tissue or microenvironment proximal to a solid tumor or cancer cells in the patient and the change in the pH of a tissue or microenvironment proximal to a solid tumor or cancer cells inhibits or prevents the intravasation of tumor cells.

In another aspect, a method of treatment of cancer is provided comprising i) selecting a therapeutic agent (e.g. a chemotherapeutic or immunotherapeutic agent), ii) formulating the therapeutic agent in a suitable formulation, iii) administering the formulation comprising the therapeutic agent, and iv) before, during or after step iii), administering a formulation comprising one or more buffering agent topically and/or transdermally in an amount effective to inhibit or prevent the growth of a tumor or tumor cells. The therapeutic agent is typically formulated in a formulation suitable for a route of administration other than topical and/or transdermal, however in certain embodiments the therapeutic agent is formulated with the buffering agent in the same formulation.

In another aspect, methods of increasing the efficacy of conventional approaches to cancer treatment are provided. In some embodiments, methods of increasing the efficacy of immunotherapy are provided comprising administering i) a formulation comprising one or more buffering agent topically and/or transdermally, and ii) before, during or after step i), administering a formulation comprising a immunotherapeutic agent. In some embodiments, methods of increasing the efficacy of biological therapeutic agents are provided comprising administering i) a formulation comprising one or more buffering agent topically and/or transdermally, and ii) before, during or after step i), administering a formulation comprising a selected biological therapeutic agent. In other embodiments, methods of increasing the efficacy of chemotherapy are provided comprising administering i) a formulation comprising one or more buffering agent topically and/or transdermally, and ii) before, during or after step i), administering a formulation comprising a chemotherapeutic agent.

In another aspect, methods of palliative care for terminally ill cancer subjects are provided comprising administering topically and/or transdermally an effective amount of a formulation comprising one or more buffering agent to a patient in need thereof, where the administration is effective to improve the quality of life of a terminally ill patient.

In another aspect, a method of treating gout is provided where an effective amount of a formulation comprising one or more buffering agent is administering topically and/or transdermally to a patient in need thereof such that the administration is effective to treat or reduce the symptoms of gout in said patient.

In another aspect, a method of treating a skin disorder in a subject is provided where an effective amount of a formulation comprising one or more buffering agent is administering topically and/or transdermally to a patient in need thereof such that the administration is effective to treat or reduce the skin disorder symptoms in said patient.

In another aspect, a method of treating melasma in a subject is provided where an effective amount of a formulation comprising one or more buffering agent is administering topically and/or transdermally to a patient in need thereof such that the administration is effective to treat or reduce the melasma symptoms in said patient.

In another aspect, a method of improving, extending the duration of remission, or maintaining remission of a cancer or tumor is provided where an effective amount of a formulation comprising one or more buffering agent is administering topically and/or transdermally to a patient in need thereof. In certain embodiments the administration is effective to alter the pH of a tissue or microenvironment proximal to a solid tumor or cancer cells in the patient and the change in the pH of a tissue or microenvironment proximal to a solid tumor or cancer cells to improve, extend the duration of remission, or maintain remission of a cancer or tumor.

In another aspect, the invention is directed to a method to inhibit metastasis and/or growth of a solid tumor contained in a subject which method comprises administering by a topical and/or transdermal route of administration to a subject in need of such inhibition an effective amount of an anti-metastasis agent. In some embodiments, the anti-metastasis agent may be buffer sufficient to increase the pH of the microenvironment of the solid tumor or cancer cells, or a protease inhibitor, an inhibitor of $Na^+/H^+$ exchanger activity, an inhibitor of epidermal growth factor receptor (EGFR), an inhibitor of src homology region 2-containing protein tyrosinase phosphatase (Shp2), withaferin A or combinations thereof. The administration is by non-systemic parenteral route includes topical administration, especially transdermal.

For transdermal topical administration in particular for agents other than buffer, a suitable formulation typically involves a penetrant that enhances penetration of the skin and is, in some embodiments, composed of chemical permeation enhancers (CPEs). In some cases, it can also include peptides designed to penetrate cells i.e. cell penetrating peptides (CPPs) also known as skin penetrating peptides (SPPs). The formulation may be applied for example in the form of topical lotions, creams, and the like, as described herein.

If the active agent is a buffer, the choice of buffer system is based on the criteria of capability of buffering at a suitable pH typically between 7 and 10.5, as well as biocompatibility of the buffer system itself and the compatibility of the buffer system with the remaining components of the formulation. Conversely, the formulation is chosen to be compatible with the buffer selected; amounts of penetrants are generally less than those advantageous for therapeutic agents in general.

Some tumors may be resistant to lower doses, but treatable with higher doses. When the pH is adjusted for the purpose of inhibiting metastasis, treatment is followed by assessment of effectiveness. More importantly, as noted above, it has been found that some tumors are resistant to buffer treatment—i.e., raising the pH does not have a metastasis inhibiting effect. See, for example, Bailey, K M, et al., *Neoplasia* (2014) 16:354-364 (supra). It is therefore one aspect of the invention to evaluate the tumors of potential subjects for treatment with buffer, e.g., by culturing biopsies for sensitivity/resistance to pH adjustment. In a related aspect, particular types of tumors are evaluated for sensitivity/resistance to pH adjustment and capacity for treatment as a function of dosage and buffer formulation composition, As described in more detail herein, raising the pH in the vicinity of other diseases, disorders, and conditions can also an effective treatment. For example, raising the pH in the vicinity of melasmas and gout is also an effective treatment. The methods of the invention can usefully be applied to treatment of these conditions as well. Thus, another aspect of the invention such methods of treatment directed to melasma and gout.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

DETAILED DESCRIPTION

Figure 1:
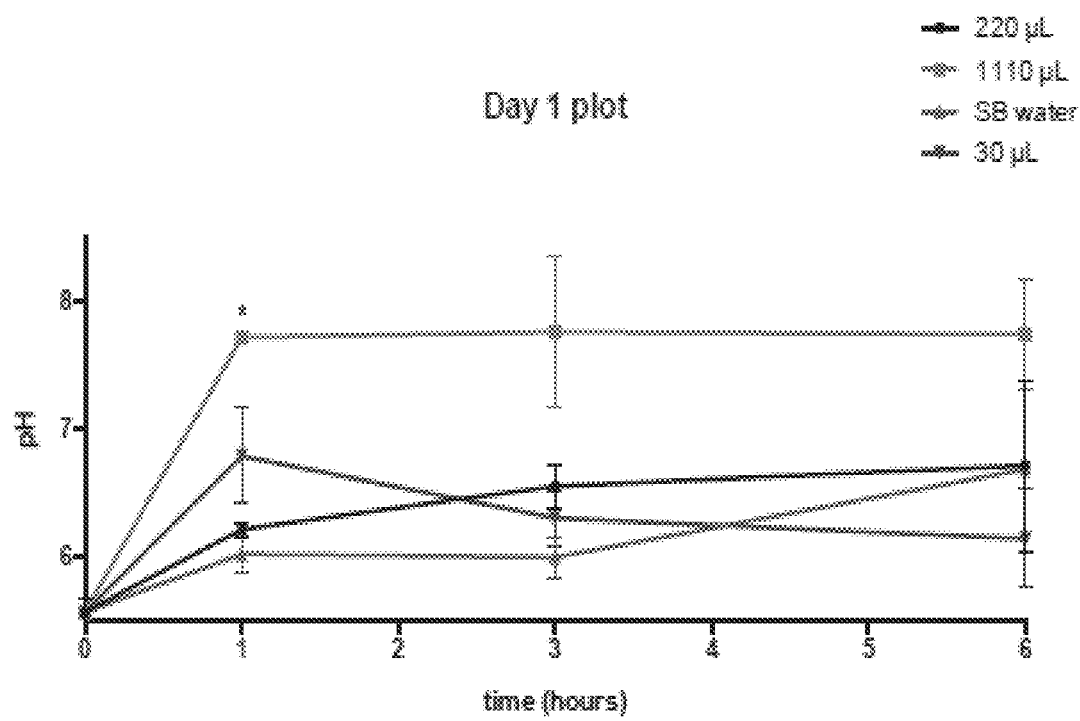
FIG. 1 shows the time course of urine pH immediately following topical administration of sodium bicarbonate in various formulations and dosage regimes.

The practices described herein employ, unless otherwise indicated, conventional techniques of tissue culture, immunology, molecular biology, microbiology, cell biology and recombinant DNA, which are within the skill of the art. See, e.g., Harlow and Lane eds. (1999) Antibodies, A Laboratory Manual and Herzenberg et al. eds (1996) Weir's Handbook of Experimental Immunology.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof. On the other hand, "one" designates the singular.

As used herein, the term "comprising" is intended to mean that the compositions and methods include the listed elements, but do not exclude other unlisted elements. "Consisting essentially of" when used to define compositions and methods, excludes other elements that alters the basic nature of the composition and/or method, but does not exclude other unlisted elements. Thus, a composition consisting essentially of the elements as defined herein would not exclude trace amounts of elements, such as contaminants from any isolation and purification methods or pharmaceutically acceptable carriers, such as phosphate buffered saline, preservatives, and the like, but would exclude additional unspecified amino acids. "Consisting of" excludes more than trace elements of other ingredients and substantial method steps for administering the compositions described herein. Embodiments defined by each of these transition terms are within the scope of this disclosure and the inventions embodied therein.

As noted above, one aspect of the invention is a method to inhibit cancer growth and metastasis, including diminution of cancer mass by non-systemic parenteral, including topical administration of antimetastatic agents, including those agents that result in buffering the immediate environment of tumor cells, including solid tumors and melanomas. For non-systemic parenteral administration, such as intramuscular, intraperitoneal or subcutaneous administration standard formulations are sufficient. These formulations include standard excipients and other ancillary ingredients such as antioxidants, suitable salt concentrations and the like. Such formulations can be found, for example, in Remington's Pharmaceutical Sciences (13$^{th}$ Ed), Mack Publishing Company, Easton, Pa.—a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals, and may include compositions that are useful intermediates for storage or research purposes. In an embodiment, administration to humans or animals may include, without limitation, topical, sublingual, rectal, vaginal, transdermal, trancutaneous, oral, inhaled, intranasal, pulmonary, subcutaneous, pulmonary, intravenous, enteral or parenteral. Suitable topical formulations for transdermal administration of active agents for the methods provided herein are described in U.S. Ser. No. 14/757,703, to Sand B., et al., incorporated herein by reference in it's entirety. Suitable penetrants are described, for example, in PCT publications WO/2016/105499 and WO/2017/127834.

As the patients and subjects of the invention method are, in addition to humans, veterinary subjects, formulations suitable for these subjects are also appropriate. Such subjects include livestock and pets as well as sports animals such as horses, greyhounds, and the like.

In an embodiment, a "pharmaceutical composition" is intended to include, without limitation, the combination of an active agent with a carrier, inert or active, in a sterile composition suitable for diagnostic or therapeutic use in vitro, in vivo or ex vivo. In one aspect, the pharmaceutical composition is substantially free of endotoxins or is non-toxic to recipients at the dosage or concentration employed.

In an embodiment, "an effective amount" refers, without limitation, to the amount of the defined component sufficient to achieve the desired chemical composition or the desired biological and/or therapeutic result. In an embodiment, that result can be the desired pH or chemical or biological characteristic, e.g., stability of the formulation. In other embodiments, the desired result is the alleviation or amelioration of the signs, symptoms, or causes of a disease, or any other desired alteration of a biological system. When the desired result is a therapeutic response, the effective amount will, without limitation, vary depending upon the specific disease or symptom to be treated or alleviated, the age, gender and weight of the subject to be treated, the dosing regimen of the formulation, the severity of the disease condition, the manner of administration and the like, all of which can be determined readily by one of skill in the art. A desired effected may, without necessarily being therapeutic, also be a cosmetic effect, in particular for treatment for disorders of the skin described herein.

In an embodiment, a "subject" of diagnosis or treatment is, without limitation, a prokaryotic or a eukaryotic cell, a tissue culture, a tissue or an animal, e.g. a mammal, including a human. Non-human animals subject to diagnosis or treatment include, for example, without limitation, a simian, a murine, a canine, a leporid, such as a rabbit, livestock, sport animals, and pets.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

Methods

Methods for treating, preventing or ameliorating a disease, disorder, a condition, or a symptom thereof or a condition related thereto are provided herein using formulations for transdermal delivery described herein below. The methods provided herein may comprise or consist of topically administering one or more of the formulations described herein to skin of a subject in need thereof. Preferred, but non-limiting embodiments are directed to methods for treating, preventing, inhibiting or ameliorating a disease, disorder, a condition, or a symptom described below.

Caners and Tumors

Many embodiments provided herein are directed to various methods of treating cancer and/or tumors. An exemplary embodiment of a method of treating cancer in a patient according to the invention comprises administering topically and/or transdermally an effective amount of a formulation comprising one or more buffering agent to a patient in need thereof, wherein said administration is effective to inhibit or prevent the growth of a tumor or tumor cells.

Another embodiment is directed to a method of preventing metastasis of tumors comprising administering topically and/or transdermally an effective amount of a formulation comprising one or more buffering agent to a patient in need thereof, where the administration is effective to inhibit or prevents the metastasis of tumors or cancer cells.

Another embodiment is directed to a method of preventing the intravasation of tumor cells comprising administering topically and/or transdermally an effective amount of a formulation comprising one or more buffering agent to a patient in need thereof, where the administration is effective to inhibit or prevent the intravasation of tumor cells.

Another embodiment is directed to a method of treatment of cancer, the method comprising i) selecting a therapeutic agent (e.g. a chemotherapeutic of immunotherapeutic agent) described herein and formulating the therapeutic agent in a formulation comprising one or more buffering agent, and iii) administering the formulation topically and/or transdermally in an amount effective to inhibit or prevent the growth of a tumor or tumor cells.

Another embodiment is directed to a method of improving, extending the duration of remission, or maintaining remission of a cancer or tumor comprising administering topically and/or transdermally an effective amount of a formulation comprising one or more buffering agent to a patient in need thereof, where administration is effective to improve, extend the duration of remission, or maintain remission of a cancer or tumor.

In other embodiments, a method of treating cancer in a patient comprises administering topically and/or transdermally an effective amount of a formulation comprising one or more buffering agent to a patient in need thereof, where the administration is effective to alter the pH of a tissue or microenvironment proximal to a solid tumor or cancer cells in the patient, wherein the change in the pH of a tissue or microenvironment proximal to a solid tumor or cancer cells inhibits the growth of said solid tumor or cancer cells.

In other embodiments, a method of altering the pH of a tissue or microenvironment proximal to a solid tumor or cancer cells in a patient is provided. These embodiments generally comprise administering topically and/or transdermally an effective amount of a formulation comprising one or more buffering agent to a patient in need thereof, wherein the administration is effective to alter the pH of a tissue or microenvironment proximal to a solid tumor or cancer cells in the patient.

In other embodiments, a method of inhibiting or preventing the metastasis of tumors in a patient is provided. These embodiments generally comprise administering topically and/or transdermally an effective amount of a formulation comprising one or more buffering agent to a patient in need thereof, wherein the administration is effective to alter the pH of a tissue or microenvironment proximal to a solid tumor or cancer cells in the patient, and where the change in the pH of a tissue or microenvironment proximal to a solid tumor or cancer cells inhibits or prevents the metastasis of tumors or cancer cells.

In other embodiments, a method of inhibiting or preventing the intravasation of tumor cells in a patient is provided. These embodiments generally comprise administering topically and/or transdermally an effective amount of a formulation comprising one or more buffering agent to a patient in need thereof, wherein the administration is effective to inhibit or prevent the intravasation of tumor cells.

Formulations provided herein are used in methods of treating many cancers, including but not limited to breast cancer, prostate cancer, pancreatic cancer, lung cancer, bladder cancer, skin cancer, colorectal cancer, kidney cancer, liver cancer, and thyroid cancer.

Formulations provided herein are also used in methods of treating a cancer or tumor, including but not limited to Adrenocortical Carcinoma, Basal Cell Carcinoma, Bladder Cancer, Bone Cancer, Brain Tumor, Breast Cancer, Cervical Cancer, Colon Cancer, Colorectal Cancer, Esophageal Cancer, Retinoblastoma, Gastric (Stomach) Cancer, Gastrointestinal Tumors, Glioma, Head and Neck Cancer, Hepatocellular (Liver) Cancer, Islet Cell Tumors (Endocrine Pancreas), Kidney (Renal Cell) Cancer, Laryngeal Cancer, Non-small Cell Lung Cancer, Small Cell Lung Cancer, Medulloblastoma, Melanoma, Pancreatic Cancer, Prostate Cancer, Renal Cancer, Rectal cancer, and Thyroid Cancer.

While preferred embodiments of the methods provided herein are typically directed to a particular cancer, solid tumor or grouping thereof, a more complete but still non-limiting listing of suitable cancers and tumors that may be tested for effectiveness according to embodiments provided herein includes the following: lymphoblastic leukemia (ALL), acute myeloid leukemia (AML), adrenocortical carcinoma, aids-related cancers, kaposi sarcoma (soft tissue sarcoma), aids-related lymphoma (lymphoma), primary cns lymphoma (lymphoma), anal cancer, astrocytomas, atypical teratoid/rhabdoid tumor, childhood, central nervous system (brain cancer), basal cell carcinoma, bile duct cancer, bladder cancer, childhood bladder cancer, bone cancer (includes ewing sarcoma and osteosarcoma and malignant fibrous histiocytoma), brain tumors, breast cancer, childhood breast cancer, bronchial tumors, burkitt lymphoma (non-hodgkin lymphoma, carcinoid tumor (gastrointestinal), childhood carcinoid tumors, cardiac (heart) tumors, central nervous system tumors, atypical teratoid/rhabdoid tumor, childhood (brain cancer), embryonal tumors, childhood (brain cancer), germ cell tumor (childhood brain cancer), primary cns lymphoma, cervical cancer, childhood cervical cancer, cholangiocarcinoma, chordoma (childhood), chronic lymphocytic leukemia (CLL), chronic myelogenous leukemia (cml), chronic myeloproliferative neoplasms, colorectal cancer, childhood colorectal cancer, craniopharyngioma (childhood brain cancer), cutaneous t-cell lymphoma, ductal carcinoma in situ (DCIS), embryonal tumors, (childhood brain CNS cancers), endometrial cancer (uterine cancer), ependymoma, esophageal cancer, childhood esophageal cancer, esthesioneuroblastoma (head and neck cancer), Ewing sarcoma (bone cancer), extracranial germ cell tumors, extragonadal germ cell tumors, eye cancer, childhood intraocular melanoma, intraocular melanoma, retinoblastoma, fallopian tube cancer, fibrous histiocytoma of bone (malignant, and osteosarcoma), gallbladder cancer, gastric (stomach) cancer, childhood gastric (stomach) cancer, gastrointestinal carcinoid tumor, gastrointestinal stromal tumors (gist) (soft tissue sarcoma), childhood gastrointestinal stromal tumors, germ cell tumors, childhood central nervous system germ cell tumors, childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis (Langerhans cell cancer), Hodgkin lymphoma, hypopharyngeal cancer (head and neck cancer), intraocular melanoma, childhood intraocular melanoma, islet cell tumors, (pancreatic neuroendocrine tumors), Kaposi sarcoma (soft tissue sarcoma), kidney (renal cell) cancer, Langerhans cell histiocytosis, laryngeal cancer (head and neck cancer), leukemia, lip and oral cavity cancer (head and neck cancer), liver cancer, lung cancer (non-small cell and small cell), childhood lung cancer, lymphoma, male breast cancer, malignant fibrous histiocytoma of bone and osteosarcoma, melanoma, childhood melanoma, melanoma (intraocular eye), childhood intraocular melanoma, Merkel cell carcinoma (skin cancer), mesothelioma, childhood mesothelioma, metastatic cancer, metastatic squamous neck cancer with occult primary (head and neck cancer), midline tract carcinoma with nut gene changes, mouth cancer (head and neck cancer), multiple endocrine neoplasia syndromes—see unusual cancers of childhood, multiple myeloma/plasma cell neoplasms, mycosis fungoides (lymphoma), myelodysplastic syndromes, myelodysplastic/myeloproliferative neoplasms, myelogenous leukemia, chronic (CML), myeloid leukemia, (acute AML), myeloproliferative neoplasms, nasal cavity and paranasal sinus cancer (head and neck cancer), nasopharyngeal cancer (head and neck cancer), neuroblastoma, non-hodgkin lymphoma, non-small cell lung cancer, oral cancer (lip and oral cavity cancer and oropharyngeal cancer), osteosarcoma and malignant fibrous histiocytoma of bone, ovarian cancer, childhood ovarian cancer, pancreatic cancer, childhood pancreatic cancer, pancreatic neuroendocrine tumors (islet cell tumors), papillomatosis, paraganglioma, childhood paraganglioma, paranasal sinus and nasal cavity cancer, parathyroid cancer, penile cancer, pharyngeal cancer, pheochromocytoma, childhood pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, renal cell (kidney) cancer, retinoblastoma, rhabdomyosarcoma, salivary gland cancer, sarcoma, childhood rhabdomyosarcoma (soft tissue sarcoma), childhood vascular tumors (soft tissue sarcoma), Ewing sarcoma (bone cancer), Kaposi sarcoma (soft tissue sarcoma), osteosarcoma (bone cancer), soft tissue sarcoma, uterine sarcoma, Sézary syndrome (lymphoma), skin cancer, childhood skin cancer, small cell lung cancer, small intestine cancer, soft tissue sarcoma, squamous cell carcinoma of the skin, squamous neck cancer with occult primary, stomach (gastric) cancer, childhood stomach, t-cell lymphoma, testicular cancer, childhood testicular cancer, throat cancer, nasopharyngeal cancer, oropharyngeal cancer, hypopharyngeal cancer, thymoma and thymic carcinoma, thyroid cancer, transitional cell cancer of the renal pelvis and ureter kidney (renal cell cancer), ureter and renal pelvis (transitional cell cancer kidney renal cell cancer), urethral cancer, uterine cancer (endometrial), uterine sarcoma, vaginal cancer, childhood vaginal cancer, vascular tumors (soft tissue sarcoma), vulvar cancer, and Wilms tumor (and other childhood kidney tumors).

Coadministration w Anti-Cancer and Immunotherapy Agents

In another aspect, formulations and/or compounds provided herein are coadministered or administered to an animal, subject or patient in conjunction with one or more chemotherapeutic compounds such as alkylating agents, antibodies and related agents with anti-tumor properties, anthracyclines, antimetabolites, antitumor antibiotics, aromatase inhibitors, cytoskeletal disruptors (e.g. taxanes), epothilones, histone deacetylace inhibitors, kinase inhibitors, nucleoside analogues, topoisomerase inhibitors, retinoids, vinca alkaloids and derivatives, and the like. The administration or co-administration of one or more formulation or composition of the invention and one or more chemotherapeutic agents can be used for the treatment of tumors or cancer in an animal, subject or patient.

As an example, alkylating agents can be administered or coadministered with or as part of a formulation provided herein. Examples of an alkylating agents that can be co-administered include mechlorethamine, chlorambucil, ifosfamide, melphalan, busulfan, carmustine, lomustine, procarbazine, dacardazine, cisplatin, carboplatin, mitomycin C, cyclophosphamide, ifosfamide, thiotepa, and dacarbazine, and analogues thereof. See for example U.S. Pat. No. 3,046,301 describing the synthesis of chlorambucil, U.S. Pat. No. 3,732,340 describing the synthesis of ifosfamide, U.S. Pat. No. 3,018,302 for the synthesis of cyclophosphamide, U.S. Pat. No. 3,032,584 describing the synthesis of melphalan, and Braunwald et al., "Harrison's Principles of Internal Medicine," 15th Ed., McGraw-Hill, New York, N.Y., pp. 536-544 (2001) for clinical aspects of cyclophosphamide, chlorambucil, melphalan, ifosfamide, procarbazine, hexamethylmelamine, cisplatin, and carboplatin. Examples of nucleoside analogues include, but are not limited to, fludarabine pentostatin, methotrexate, fluorouracil, fluorodeoxyuridine, CB3717, azacitidine, cytarabine, floxuridine, mercaptopurine, 6-thioguanine, cladribine, and analogues thereof.

In another aspect, formulations provided herein are administered with chemosensitising agents such as those described for example in U.S. Pat. No. 3,923,785 describing the synthesis of pentostatin, U.S. Pat. No. 4,080,325 describing the synthesis of methotrexate, U.S. Pat. No. 2,802,005 describing the synthesis of fluorouracil, and Braunwald et al., "Harrison's Principles of Internal Medicine," 15th Ed., McGraw-Hill, New York, N.Y., pp. 536-544 (2001) for clinical aspects of methotrexate, 5-fluorouracil, cytosine arabinoside, 6-mercaptopurine, 6-thioguanine, and fludarabine phosphate. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992), incorporated by reference herein.

In another aspect, formulations provided herein can be administered or co-administered with diterpene compounds, including but not limited to paclitaxel, docetaxel, cabazitaxel, and the like.

In another aspect, formulations provided herein can be administered or co-administered with compounds that inhibit topoisomerase II or compounds that otherwise interact with nucleic acids in cells. Such compounds include, for example, doxorubicin, epirubicin, etoposide, teniposide, mitoxantrone, and analogues thereof. In one example, this combination is used in treatment to reduce tumor cell contamination of peripheral blood progenitor cells (PBSC) in conjunction with high-dose chemotherapy and autologous stem cell support (HDC-ASCT). See U.S. Pat. No. 6,586,428 to Geroni et al.

In another aspect, formulations provided herein can be administered or co-administered with immunotherapeutic agents. Immunotherapy has become a promising approach to treat cancer. Kruger C., et al., Immune based therapies in cancer, Histol. Histopathol, 2007, v22, 687-696. The types of immunotherapies used to treat cancer and can be categorized as active, passive or hybrid (active and passive). Active immunotherapy directs the immune system to attack tumor cells by targeting TAAs. Passive immunotherapies enhance existing anti-tumor responses and include the use of checkpoint inhibitors, monoclonal antibodies, lymphocytes and cytokines. A suitable immunotherapeutic agent or immunotherapy may be a biologic or biologically active agent such as an antibody or modified antibody or cell based therapy such as chimeric antigen receptor therapy (CAR-T). It is recognized that there may be overlap in categorizing and classifying such agent as biological agents, immunotherapeutic agents, cell-based therapeutics, biological therapeutic agents and the like. Examples of approved antibody immunotherapeutics include, alemtuzumab, atezolizumab, avelumab, ipilimumab, durvalumab, nivolumab, ofatumumab, rituximab, and trastuzumab. These and others are suitable for use in certain embodiments provided herein.

In another aspect, formulations can be administered or co-administered with biological therapeutic agents and other therapeutic drugs. For example, virulizin (Lorus Therapeutics), which is believed to stimulate the release of tumor necrosis factor, TNF-α, by tumor cells in vitro and stimulate activation of macrophage cells. This can be used in combination with one or more formulation of the invention to increase cancer cell apoptosis and treat various types of cancers including pancreatic cancer, malignant melanoma, kaposi's sarcoma (KS), lung cancer, breast cancer, uterine, ovarian and cervical cancer. Another example is CpG 7909 (Coley Pharmaceutical Group), which is believed to activate NK cells and monocytes and enhance ADCC. Cytokines such as interferons and interleukins (e.g. EPO, thrombopoietin) are biological agents useful certain embodiments in combination with one or more formulation of the invention. Other types of suitable biological therapeutic agents include RNA and protein bases-agents such as enzymes. These therapeutic agents and others can also be used in combination with formulations provided herein.

Another example of a biological therapeutic agent that is used for the treatment of certain cancers in certain embodiments are angiogensis inhibitors. Accordingly, formulations of the invention can also be combined with angiogensis inhibitors to increase anti-tumor effects. Angiogenisis is the growth of new blood vessels. This process allows tumors to grow and metastasize. Inhibiting angiogeneisis can help prevent metastasis, and stop the spread of tumors cells. Angiogenisis inhibitors include, but are not limited to, angiostatin, endostatin, thrombospondin, platelet factor 4, Cartilage-derived inhibitor (CDI), retinoids, Interleukin-12, tissue inhibitor of metalloproteinase 1, 2 and 3 (TIMP-1, TIMP-2, and TIMP-3) and proteins that block the angiogensis signaling cascade, such as anti-VEGF (Vascular Endothelial Growth Factor) and IFN-alpha. Angiogenesis inhibitors can be administered or co-administered with tumor specific constructs, including antigen-binding constructs capable of mediating, for example, ADCC and/or complement fixation or chemotherapy-conjugated antigen-binding of the invention to combat various types of cancers, for example, solid tumor cancers such as lung and breast cancer. Other examples of biological therapeutic agents include inhibitors of E-cadherin and of epidermal growth factor receptor (EGFR). Known inhibitors include erlotinib, an anti-integrin drug (Cilengitide), Cariporide, Eniporide and Amiloride.

In another aspect, formulations of the invention can be administered or co-administered with disease modifying anti-rheumatic agents (DMAR agents) for the treatment of rheumatoid arthritis, psoriasis, ulcerative colitus, systemic lupus erythematosus (SLE), Crohn's disease, ankylosing spondylitis, and various inflammatory disease processes. In such treatment, the constructs, for example, antigen-binding constructs, of the invention are commonly administered in conjunction with compounds such as azathioprine, cyclosporin, gold, hydroxychloroquine, methotrexate, penicallamine, sulphasalazine, and the like.

In another aspect, formulations provided herein can be used with palliative (non-radical) operations to surgically remove tumors. In this aspect, one or more formulations of the invention can be administered before and after surgical extractions of tumors in order to reduce the likelihood of metastasis and reoccurrence by killing any cancer cells that were not removed during the surgery.

Other diseases, conditions, and disorders described herein can be treated with formulations and methods provided herein.

Gout, Hyperuricaemia, Inflammatory Arthritis, and Related Inflammatory Disorders Gout is a form of inflammatory arthritis characterized by recurrent attacks of a red, tender, hot, and swollen joint. Pain typically comes on rapidly in less than twelve hours. The joint at the base of the big toe is affected in about half of cases. It may also result in tophi, kidney stones, or urate nephropathy. Gout is due to persistently elevated levels of uric acid in the blood. This occurs due to a combination of diet and genetic factors. At high levels, uric acid crystallizes and the crystals deposit in joints, tendons, and surrounding tissues, resulting in an attack of gout. Gout occurs more commonly in those who regularly eat meat or seafood, drink beer, or are overweight. Diagnosis of gout may be confirmed by the presence of crystals in the joint fluid or in a deposit outside the joint. Blood uric acid levels may be normal during an attack. Disorders and conditions related to gout include, for example, osteoarthritis, rheumatoid arthritis and psoriatic arthritis.

In another aspect, methods of treating a subject, ameliorating, or preventing a condition characterized by abnormal tissue levels of uric acid are provided. Methods of the invention may include the modulation of uric acid levels in subject. Accordingly, a method of treating a disease or disorder associated with abnormal levels of uric acid in a patient is provided comprising administering topically and/or transdermally an effective amount of a pharmaceutical formulation comprising one or more buffering agent to a patient having abnormal levels of uric acid and in need thereof, where the administration is effective to treat or reduce the symptoms of abnormal levels of uric acid in said patient.

Certain embodiments provided herein are directed to method of treating gout and related disorders. A method of treating gout and related disorders in accordance with the invention may comprise topically and/or transdermally administering an effective amount of a formulation comprising one or more buffering agent to a patient having gout and in need thereof, wherein said administration is effective to treat or reduce the symptoms of gout in said patient.

Some embodiments are directed to a method of treating or ameliorating gout comprising topically and/or transdermally administering an effective amount of a formulation comprising about 30% to about 35% sodium bicarbonate and, optionally, about at least 0.5% menthol to a patient having gout and in need thereof, wherein said administration is effective to treat or reduce the symptoms of gout in said patient.

Some embodiments are directed to a method of treating or ameliorating gout comprising topically and/or transdermally administering an effective amount of a formulation comprising about 30% to about 35% sodium bicarbonate and, optionally, about at least 0.5% menthol to a patient having gout and in need thereof, wherein said administration is effective to treat or reduce the symptoms of gout in said patient.

In one embodiment, a method of treating or ameliorating gout is provided comprising topically and/or transdermally administering an effective amount of a formulation comprising about 33% sodium bicarbonate and about 0.5% menthol, to a patient having gout and in need thereof, wherein said administration is effective to treat or reduce the symptoms of gout in said patient.

In some embodiments, a condition disorder related to gout or directly affected or worsened by elevated levels of uric acid in the blood in a subject is treated, including for example a recurrent gout attack, gouty arthritis, hyperuricaemia, gout related cardiovascular disorders (e.g. hypertension, cardiovascular disease, coronary heart disease), Lesch-Nyhan syndrome, Kelley-Seegmiller syndrome, kidney disease, kidney stones, kidney failure, joint inflammation, inflammatory joint disease, arthritis, osteoarthritis, rheumatoid arthritis and psoriatic arthritis, urolithiasis, plumbism, hyperparathyroidism, psoriasis or sarcoidosis.

In certain embodiments, a method of treating gout and related disorders in accordance with the invention may also comprise topically and/or transdermally administering an effective amount of a formulation comprising one or more buffering agent to a patient having gout or a related disorder and in need thereof, wherein said administration is effective to treat or reduce the symptoms of gout in said patient, where the method further includes the administration or coadministration of another drug, therapeutic agent, or treatment. Suitable therapeutic agents for these embodiments include, for example, drugs for pain and inflammation in general (e.g. colchicine), corticosteroids, nonsteroidal anti-inflammatory drugs (NSAIDS), oral urate-lowering therapy (ULT, e.g. with xanthine oxidase inhibitors, drugs that lower uric acid (e.g. allopurinol, febuxostat, lesinurad, pegloticase, probenecid). In some embodiments, such therapeutic agents may be formulated and administered as part of a formulation provided herein for topical and/or transdermal administration.

Urinary and Renal Stones and Related Disorders

Kidney stones (renal lithiasis, nephrolithiasis) are common in humans and animals, and they typically comprise hard deposits made of minerals and salts that form inside the bladder, kidneys, and urinary tract. Such stones often form when the urine becomes concentrated, allowing minerals to crystallize and stick together. Also, when a subject does not drink sufficient water there can be an accumulation of uric acid that is believed to be correlated with the formation of such stones. An excessively acidic environment in the urine of a subject is also thought to lead to the formation of kidney stones. They can be quite painful, and can lead to complications such as the blocking of the tube connecting the kidney to the bladder. Embodiments of the formulations provided herein have been found to be useful for the treatment, inhibit, amelioration of urinary and renal stones in a subject.

Accordingly, other embodiments provided herein are directed to methods of urinary and renal stones and related disorders. In an exemplary embodiment, a method of ameliorating or treating a urinary stone in accordance with the invention typically comprises topically and/or transdermally administering an effective amount of a pharmaceutical formulation comprising one or more buffering agent to a patient having a urinary stone and in need thereof, wherein said administration is effective to ameliorate, treat or reduce the symptoms of the urinary stone in said patient.

Examples of such conditions involving stones include, but not limited to bladder stones, kidney stones (calcium, calcium oxalate, calcium phosphate, cystine, magnesium ammonium phosphate, uric acid, struvite), renal stones, bilateral stone disease, urolithiasis during pregnancy, pediatric stones, stones in animals (e.g. urinary stones in animals), stones in patients with solitary kidneys, nephrolithiasis, other types of stones (e.g. bladder, urinary), patients with bleeding diathesis and related disorders, urolithiasis, as well as in conjunction with medical or surgical procedures such as a lithotripsy or ureteroscopy.

In certain embodiments, the patient is an animal such as a pet (e.g. cat, dog, bird), farm animal, or livestock. In non-limiting preferred embodiments, the urinary stone that is treated can be a bladder or kidney stone.

Skin Disorders

Other embodiments are directed to methods of treating a skin condition or disorder in a patient. These embodiments typically comprise topically and/or transdermally administering an effective amount of a formulation comprising one or more buffering agent to a patient having a skin condition or disorder and in need thereof, wherein said administration is effective to ameliorate, treat or reduce the symptoms of the skin condition or disorder.

An exemplary but non-limiting skin disorder that is treated herein in particular embodiments is melasma. Melasma is a common skin problem that leads to skin pigmentation problems such as brown to gray-brown patches, usually on the face, cheeks, bridge of their nose, forehead, chin, and above their upper lip.

Melasma is believed to be triggered or worsened by birth control pills, pregnancy, and hormone therapy, stress, thyroid disease, and sun exposure. Sun exposure is believed to cause melasma because ultraviolet rays affect the cells that control pigment (melanocytes).

Thus, in certain embodiments methods of treating melasma are provided that comprise topically and/or transdermally administering an effective amount of a formulation comprising one or more buffering agent to a patient having melasma and in need thereof, wherein said administration is effective to ameliorate, treat or reduce the symptoms of the melasma. In some embodiments, methods of the invention use formulations provided herein in conjunction with or co-administered with another treatment for melasma (e.g. sun protection or a sunscreen).

Another disorder or condition of the skin that is treated is skin damage. These embodiments typically comprise topically and/or transdermally administering an effective amount of a formulation comprising one or more buffering agent to a patient having skin damage and in need thereof, wherein said administration is effective to ameliorate, treat or reduce the skin damage or symptoms associated with the skin damage.

Other embodiments are directed to rejuvenating skin, and accordingly methods of rejuvenating skin are provided that comprise topically and/or transdermally administering an effective amount of a formulation comprising one or more buffering agent to a subject in need of skin rejuvenation.

In certain embodiments, methods are provided that prevent or ameliorate collagen acylation in the skin of a patient. Alternative embodiments are also directed to the pre-treatment of skin to prevent or ameliorate skin damage caused by collagen acylation and other factors.

Regulation of $Na^+/H^+$ exchanger isoform 1 (NHE1) activity

In normal and neoplastic cells, the maintenance of pH homeostasis is chiefly regulated by the $Na^+/H^+$ exchanger isoform 1. Dysregulation of $Na^+/H^+$ exchanger isoform 1 (NHE1) activity is the hallmark of cells undergoing tumorigenesis and metastasis, the leading cause of patient mortality. While not being bound to any theory, the acidic tumor microenvironment is thought to facilitate the development of resistance to chemotherapy drugs and to promote extracellular matrix remodeling leading to metastasis. NHE1 activity has been shown to play an important role in the regulation of cell volume and shape, while also promoting cell growth, proliferation, differentiation, and apoptosis. It may contribute to the development of multidrug resistance of tumor cells to many chemotherapy drugs, which also hinders immune rejection of these tumors. Weakly basic chemotherapy agents (e.g., doxorubicin) are likely pronated in acidic pH, which impedes their entrance into cells and prevents them from reaching their intracellular molecular targets.

It is another aspect of the invention to evaluate whether manipulating the tumor microenvironment through the modulation of NHE1 activity could aid in chemotherapy treatment strategies in a co-adjuvant manner post-surgical intervention or, alternatively, in a co-neoadjuvant manner prior to surgery.

A problem in the development of NHE1-specific inhibitors has been driven by the need to counter the adverse effects of excessive exchanger activity in the mammalian myocardium. Amiloride, a potassium-sparing diuretic that has been used clinically, is a NHE inhibitor. Several other drugs have since been and investigated in terms of their increased selectivity and potency towards NHE1 inhibition and testing these inhibitors for their anti-cancer properties is a subject of ongoing research. The two major families of these compounds are (i) the pyrazine derivatives (e.g., 5-(N,N-hexamethylene) amiloride), 5-(N,N-dimethyl) amiloride, 5-(N-ethyl-N-isopropyl-amiloride)), and (ii) the benzoylguanidines (e.g., cariporide, eniporide, HOE-694).

Thus another aspect of the invention is to evaluate the inhibition of NHE1 to be used as a target to increase the efficacy of anticancer drugs (e.g. chemotherapeutics, immunotherapeutic, biological agents described herein) and as recent studies have lent credence to this hypothesis.

Also provided herein are methods of use of a NHE1 inhibitor administered parenterally or topically directed against the various proteins regulating the reversed pH gradient of tumors. The invention also enables the strategy of targeting NHE1 in synergistic combination with 'traditional' pharmacological agents against one or more of its up-stream activators. Both topical and parenteral administration that are themselves non-systemic are contemplated as overcoming the difficulties with oral administration, compromised first-pass metabolism and unacceptable bioavailability.

Figure 16:
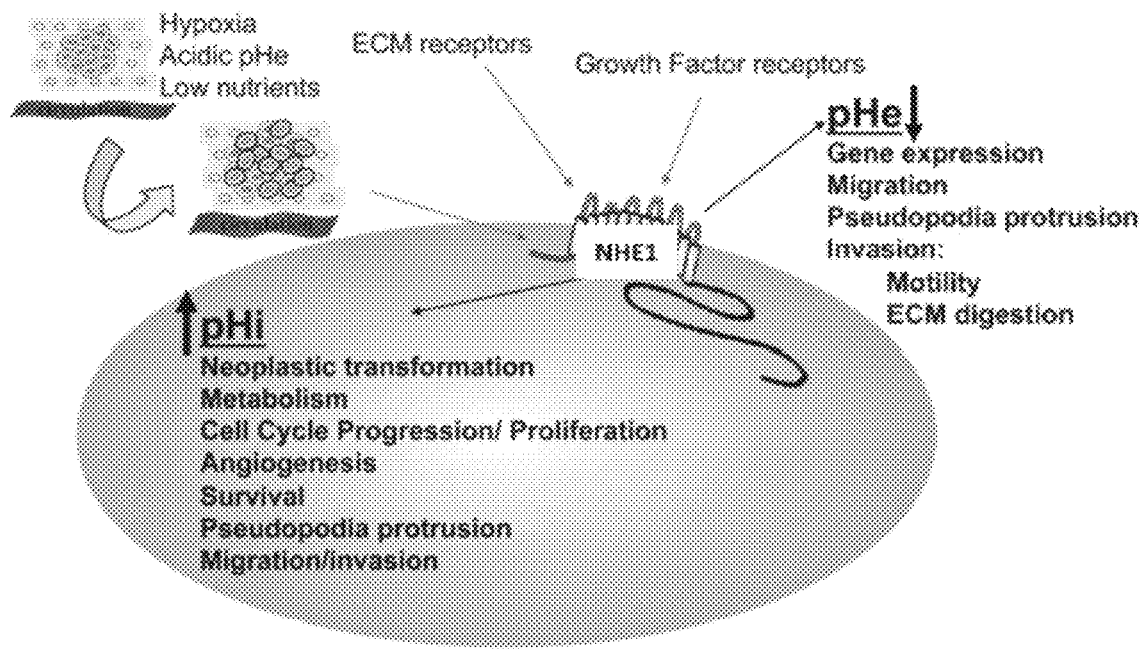
FIG. 16—shows the regulation of NHE1 and its roles in driving tumor behaviors.

FIG. 16 shows the regulation of NHE1 and its roles in driving tumor behaviors. A general scheme showing the major systems regulating the activity of NHE1 with the resultant alkalinization of intracellular pH (pHi) and acidification of extracellular pH (pHe). These altered intra- and extra-cellular environments, in turn, drive a series of tumor cell behaviors resulting in progression to more aggressive characteristics.

Figure 17:
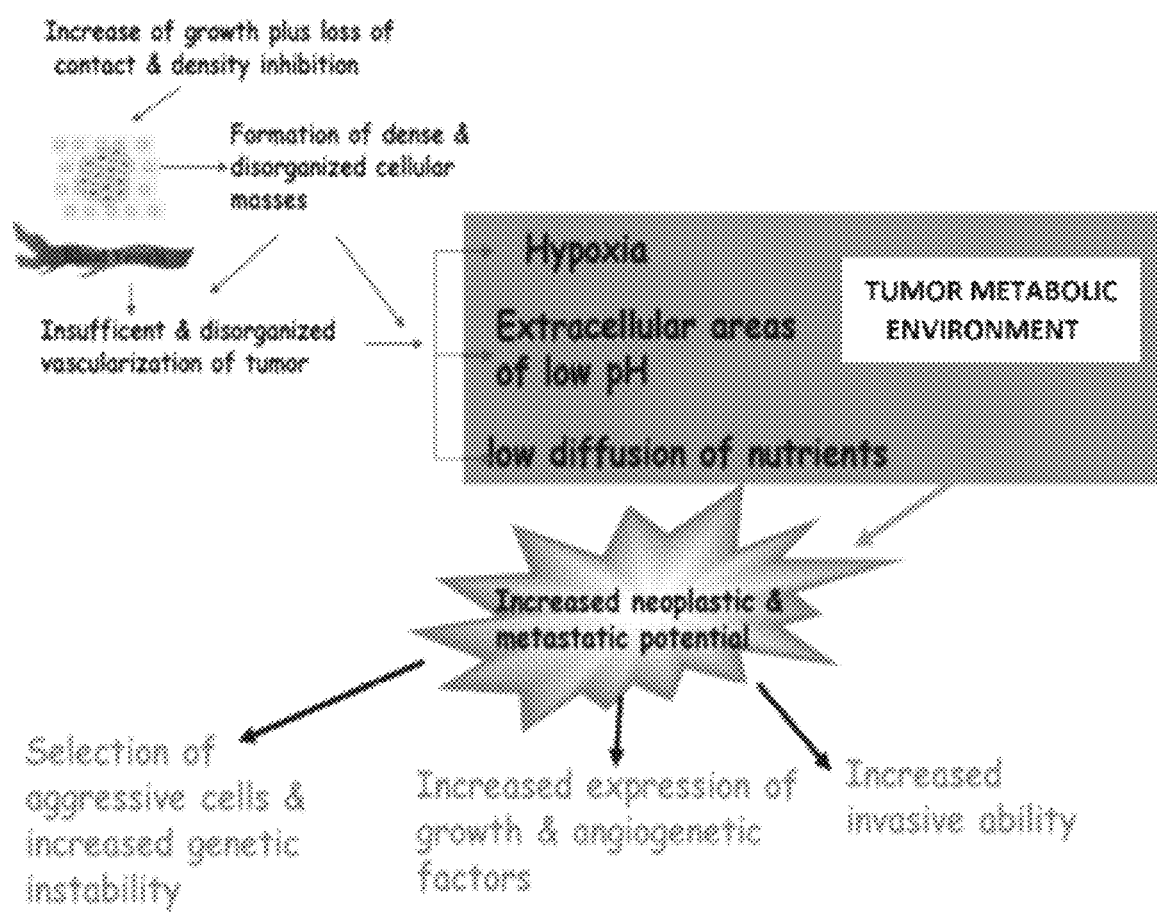
FIG. 17—illustrates the development of tumor metabolic microenvironment.

FIG. 17 illustrates the development of tumor metabolic microenvironment. General scheme showing how the dense, disorganized tumor interacts with a reduced circulatory availability to produce the tumor metabolic microenvironment, which is composed of low serum availability, hypoxia and acidic extracellular pH. Exposure to this microenvironment further drives metastatic progression.

Another aspect of the invention is directed to the use of NHE1 inhibitors as an anticancer target. Due to the importance of NHE1 in numerous physiological and pathological processes, several inhibitors have been developed. The inhibitors belong to two groups of modifications of the structure of the K-sparing diuretic, amiloride, (3.5-diamino-6-chloro-N-(diaminomethylene) pyrazinecarboxamide), the first compound found to have inhibitory activity.

The first series of other NHE1 inhibitory drugs based on the chemical scaffold of amiloride had a slightly higher inhibitory activity and specificity for NHE1. Later developed and also included are inhibitors where the pyrazine moiety of amiloride is substituted with a phenyl ring or a heterocycle pyridine to produce benzoylguanidines, including for example HOE-694, cariporide (HOE-642), and eniporide (EMD85131). There is an additional series of NHE1 inhibitor compound whose structure is independent of amiloride. One of this is SL-591227 which was the first potent and NHE1 selective non-guanidine inhibitor. The group of Tomoda developed phenoxazine derivatives (Phx-1) and Phx-3 that are highly selective for NHE1 and which stimulate apoptosis in a variety of cancer cell lines. Additionally, a Also, researchers have synthesized a pyrimidine analog named compound 9t has been recently developed (Bristol-Meyers) that is reported to have a very high inhibitory activity, as much as 500-times more potent than cariporide, and much greater selectivity for NHE1 over NHE2 with a 52% oral bioavailability and a plasma half-life of 1.5 hours in rats. It appears however that reports on the use of compound 9t either in vitro or in vivo are limited. However, compound 9t and other pyrimidine analogs are contemplated as within the scope of certain embodiments.

Inhibitors of the amiloride series are also used in various embodiments, these include cariporide and eniporide.

Another aspect of the invention is to minimize the systemic dose of the drug in order to dissociate the adverse effects and off-target effects from the beneficial effects. Importantly, the potency of cariporide and some other MHE inhibitors is related to the ionization state of the guanidine residues. Therefore, the acidic tumor microenvironment could turn out to be an advantage in terms of dose-dependent side effects as these compounds would be more efficient at inhibiting NHE1.

In certain embodiments combinations of NHE1 inhibitory drugs compounds can be used. Such combinations can include both (i) cocktails of inhibitors directed against the various proteins regulating the reversed pH gradient of tumors and (ii) the strategy of targeting NHE1 in combination with a 'traditional' pharmacological agent against one or more of its up-stream activators (FIG. 16).

These strategies finally present the promise of a real paradigm shift in cancer treatment towards manipulating the selective forces controlling the dysregulated pH dynamics to reduce both the growth and the metastatic potential of tumors (FIG. 17).

Other aspects of the invention include the combination of proton transport inhibitors and the new 'biological targeting' of certain growth factor receptors to inhibit metastasis.

Other aspects include treating tumors with hyperthermia and there is a group of studies showing that the lowering of pH by targeting NHE1 can strongly enhance the thermosensitivity of the cancer cell. These embodiments have very real and important future possibilities for the combined use of proton transporter inhibitors together with hyperthermia.

For these reasons, combination therapies are used herein to effectively treat many tumors screened for pertinent pathway dependence. In line with this, the relatively high concentration of growth factors in tumors and their positive role in NHE1 activation represents a perfect platform for the topical administration of inhibitors through the combination the NHE1 inhibitors and the new biological targeting of some of these growth factor-receptors. Accordingly, aspects of the invention include the multi-combined therapy of NHE1 inhibitors, such as cariporide, with inhibitors of one or more of these receptors having a role in both activating NHE1 and promoting tumor progression.

Other aspects include the parenterally or topically administered composition as a stand alone or in synergistic combination with traditional pharmacological agents. Topical administration is most conveniently transdermal, but further includes transmembrane administration, for example by suppository or intranasal application Other aspects include the topical administration of agents and drugs, with or without occlusion in any manner and which are not conjugated with or delivered by means of penetration enhancing formulations, but are merely applied to the intact skin with or without massaging the skin for the purpose of breaching the skin's permeation barrier.

The applicant surprisingly discovered that the combination of two hypothetical mechanisms, functioning in synergy, was successful in transdermal drug delivery (TDDD) of guest molecules of molecular weights exceeding 500 Da and, in fact, beyond 150 kDa. These two synergistic mechanisms involve different interactions between the SPPs and the cellular moiety in the "transcellular" mechanism and the CPEs in the "extracellular" mechanism.

In another aspect, the invention discloses and provides integrative and cooperative methods with compositions that are directed to the simultaneous and selective disruption of the cellular and lipid matrix contributions to the SC permeation barrier in conjunction with the transdermal delivery of agents. The mode of each physico-chemical component will be presented separately, although they may participate cooperatively in a chemical permeation enhancement (CPE) composition.

In another aspect a biochemical process, which is directed to the cellular component of the SC permeability barrier, is facilitated by a synergistic action of several biological processes, which combine to enhance transdermal drug delivery. In some embodiments, each of these processes are used individually.

Other embodiments include the use of TD-1, as well as the other cationic cyclo-peptide variants identified as TDR-2, TDR-3 and TDR-7, in which arginine substitutions are made at N-4, N-5 and N-7, and TDK-2, TDK-3 and TDK-7, in which lysine substitutions are made at N-2, N-3 and N-7. Also embodied in this patent is cationic cyclo-peptide variant TD-34 as bis-substitute peptide in N-5 and N-6. The cyclic structure and the disulfide constrained nature is critical for enhancement activity of the peptides. The TDS series of the same amino acid sequence of cyclic structure with TD-1 is further embodied as a modification via substitution of the N-terminal with three amino acids possessing the same cationic group with various side-chain lengths. The enhancement activity has been demonstrated to be proportional to side-chain length and identified as TDS-3>TDS-2>TDS-1.

While the exact mechanism is unclear, our studies have revealed the profound activity of cell penetrating peptides (CPPs) with special reference to TD-1, to be upon interactions with the skin cellular components. The CPPs function by permeating through the transcellular route passing through hydrophilic keratin-packed corneocytes that are embedded in multiple hydrophobic lipid bilayers. While partitioning into the keratin-rich corneocytes, they form bridges that bind with the filamentous keratin α-helices via hydrogen bonds in co-administration as peptide-chaperones without interacting with the guest cargo or degrading the lipid matrix. SPPs, in fact, enhance the lipid organization while simultaneously increasing skin electrical conductivity. TD-1 is non-cytotoxic and non-irritating to skin.

It has been demonstrated that the CPPs also utilize the intercellular pathways via small gaps between the corneocytes by disrupting cell-to-cell junctional desmosomes expeditiously, thereby modifying the normal ultrastructural spacing from about 30 nm to about 466 nm in as little as 30 minutes from topical administration. Transmission electron microscopy has revealed that the intercellular gaps are a transient process that will escort macromolecules across the SC permeation barrier restoring the breaches in about one hour after application.

The co-administration of CPPs has been postulated to result in a statistically significant increase in percentage of α-helices of keratins, suggesting that CPPs stabilize these structural proteins (keratins). The intra-cellular keratins are stabilized by disulfide bonds, which are tightly packed either in α-chains (α-keratins) or in β-sheet (β-keratins) structures. The high-degree of cross-linking by the disulfide bonds, hydrophobic interactions and hydrogen bonds between the keratin filament structures within the individual corneocytes confer its mechanical stability preventing free drug transport.

Keratolytic agents will disrupt the tertiary structure and hydrogen bonds between individual keratin filaments, thereby promoting penetration through intact skin. The administration of keratolytic agents will release keratin-bound active drug and enhance bioavailability.

One biochemical process is deployed to disrupt the disulfide linkage of the keratin filaments of which the corneocytes of the SC are comprised. This is contributed by means of a reducing agent containing a thiol moiety. Thioglycolic Acid (TGA) at 5% concentration is the preferred embodiment. Other agents, such as Dithiothretol (DTT), β-Mercaptoethanol (β-ME) and Urea Hydrogen Peroxide at 17.5% concentration might be similarly employed to act upon the hydrogen bonds, as well as the disulfide bonds.

An additional keratolytic agent or enzyme, such as Proteinase K might be employed to degrade the keratin substrate at about 10 mg/mL. The optimal pH of keratolytic activity is around pH 8, while activity is detected in a broad range of pH values between 6 to 11 for serine proteases. Chemical hydrolysis will further compromise the barrier property contributed by the corneocytes but the process is irreversible and concentration-dependent.

The simultaneous application of the reducing agent has been demonstrated to have no adverse effect on the keratolytic enzymes and, in fact, allows the preferential access of the enzymes to the substrate for enhanced proteolytic attack.

Sigma-Aldrich offers an appropriate keratinolytic product (K4519-500UN), which is a non-specific serine protease with the capability of degrading insoluble keratin substrates by cleaving non-terminal peptide bonds.

This patent further embodies an alternative to the reducing agent/keratolytic enzyme combination by means of two cooperating enzymes isolated from a keratin-degrading bacterium, *Stenotrophomonas* sp. strain D-1. These synergistic enzymes disrupt the disulfide bonds while simultaneously degrading the keratin substrate.

Formulations

A formulation for transdermal delivery may, for example, comprise two components or it may comprise one or more buffering agent and a penetrant. Typically, however, a penetrant is less than 85% w/w. The formulation may have a detergent of at least 1% w/w. For example, a suitable formulation may comprise about 10-56% w/w buffering agent and a penetrant. In one aspect, disclosed herein is a formulation for transdermal delivery of one or more buffering agent through the skin of a subject, comprising: a buffering agent comprising a carbonate salt in an amount between about 10-56% w/w; a penetrant portion in an amount between about 5 to 55% w/w; a detergent portion in an amount of at least 1% w/w; and wherein the formulation comprises water in an amount from none up to about 77% w/w.

In another aspect, disclosed herein is a method for transdermal delivery of a carbonate salt of the formulation comprising: a buffering agent comprising a carbonate salt in an amount between about 10-45% w/w; a penetrant portion in an amount between about 5 to 55% w/w; a detergent portion in an amount between about 1 to 15% w/w; and wherein the formulation comprises water in an amount between about 15 to 65% w/w, through the skin of a subject, wherein the carbonate salt of the formulation is in an amount between about 15-32% w/w of the formulation.

In yet another aspect, disclosed herein is a formulation for transdermal delivery of a therapeutic agent through the skin of a subject, wherein the formulation comprises at least one active agent in an amount effective for treatment of a condition in the subject and the formulation comprising: a buffering agent comprising a carbonate salt in an amount between about 10-45% w/w; a penetrant portion in an amount between about 5 to 55% w/w; a detergent portion in an amount between about 1 to 15% w/w; wherein the formulation comprises water in an amount between about 15 to 65% w/w, through the skin of a subject, wherein the carbonate salt of the formulation is in an amount between about 15-32% w/w of the formulation, therapeutic, and wherein the alkalinity of the formulation enhances penetration of the therapeutic agent.

In one aspect, disclosed herein is a formulation for transdermal delivery of one or more buffering agent through the skin of a subject, comprising: a buffering agent comprising a carbonate salt in an amount between about 10-45% w/w; a penetrant portion in an amount between about 5 to 55% w/w; a detergent portion in an amount between about 1 to 15% w/w; and wherein the formulation comprises water in an amount between about 15 to 65% w/w, and wherein the formulation comprises less than about 12% w/w lecithin.

In another aspect, disclosed herein is a method for transdermal delivery of a carbonate salt of the formulation comprising: a buffering agent comprising a carbonate salt in an amount between about 10-45% w/w; a penetrant portion in an amount between about 5 to 55% w/w; a detergent portion in an amount between about 1 to 15% w/w; and wherein the formulation comprises water in an amount between about 15 to 65% w/w, and wherein the formulation comprises less than about 12% w/w lecithin, through the skin of a subject, wherein the carbonate salt of the formulation is in an amount between about 15-32% w/w of the formulation, wherein the formulation comprises less than about 12% w/w lecithin, and wherein the alkalinity of the formulation enhances penetration of the therapeutic agent.

In yet another aspect, disclosed herein is a formulation for transdermal delivery of a therapeutic agent through the skin of a subject, wherein the formulation comprises at least one active agent in an amount effective for treatment of a condition in the subject and the formulation comprising: a buffering agent comprising a carbonate salt in an amount between about 10-45% w/w; a penetrant portion in an amount between about 5 to 55% w/w; a detergent portion in an amount between about 1 to 15% w/w; wherein the formulation comprises water in an amount between about 15 to 65% w/w, through the skin of a subject, wherein the carbonate salt of the formulation is in an amount between about 15-32% w/w of the formulation, and wherein the formulation comprises less than about 12% w/w lecithin.

In some embodiments, a suitable formulation comprises: Lipmax™ in an amount between about 1-20% w/w; benzyl alcohol in an amount between about 0.25 to 5% w/w; menthol in an amount between about 0.1-5% w/w; Pluronic® in an amount between about 0.1-5% w/w; water in an amount between about 10-80% w/w; sodium carbonate in an amount between about 1-32% w/w; sodium bicarbonate in an amount between about 1-32% w/w; ethylene glycol tetraacetic acid in an amount less than about 5% w/w; propylene glycol in an amount between about 0.5-10% w/w; almond oil in an amount between about 0.5-10% w/w; cetyl alcohol in an amount between about 0.5-10% w/w; lecithin in an amount less than about 12% w/w; Cetiol Ultimate® in an amount less than about 10% w/w; and ethanol in an amount between about 0.5-10% w/w.

In some embodiments, a suitable formulation comprises: Lipmax™ in an amount between about 1-20% w/w; benzyl alcohol in an amount between about 0.25 to 5% w/w; menthol in an amount between about 0.1-5% w/w; Durasoft® in an amount between about 0.1-5% w/w; Pluronic® in an amount between about 0.1-5% w/w; water in an amount between about 10-80% w/w; sodium carbonate in an amount less than about 32% w/w; sodium bicarbonate in an amount between about 1-32% w/w; ethylene glycol tetraacetic acid in an amount less than about 5% w/w; sodium decanoate in an amount less than about 5% w/w; propylene glycol in an amount between about 0.5-10% w/w; almond oil in an amount between about 0.5-10% w/w; zinc oxide in an amount less than about 2% w/w; cetyl alcohol in an amount between about 0.5-10% w/w; and ethanol in an amount between about 0.5-10% w/w.

In some embodiments, a suitable formulation comprises: Water in an amount between about 10-80% w/w; Phospholipon® 90 G in an amount between about 0.5-16% w/w; Myritol® 312 in an amount between about 0.5-10% w/w; isopropyl palmitate in an amount between about 1-10% w/w; Cetiol® Ultimate in an amount between about 0.25-5% w/w; stearic acid in an amount between about 0.25-5% w/w; cetyl alcohol in an amount between about 0.25-5% w/w; benzyl alcohol in an amount between about 0.25-5% w/w; propylene glycol in an amount between about 0.25-5% w/w; glycerin in an amount between about 0.25-5% w/w; ethanol in an amount between about 0.25-5% w/w; Pluronic® in an amount between about 0.1-5% w/w; Lipmax™ in an amount between about 1-20% w/w; and sodium bicarbonate in an amount between about 1-32% w/w.

In some embodiments, a suitable formulation comprises: Siligel™ in an amount between about 1-5% w/w; water in an amount between about 10-80% w/w; Phospholipon® 90 G in an amount between about 0.5-16% w/w; Myritol® 312 in an amount between about 0.5-10% w/w; isopropyl palmitate in an amount between about 1-10% w/w; Cetiol® Ultimate in an amount between about 0.25-5% w/w; stearic acid in an amount between about 0.25-5% w/w; cetyl alcohol in an amount between about 0.25-5% w/w; benzyl alcohol in an amount between about 0.25-5% w/w; propylene glycol in an amount between about 0.25-5% w/w; glycerin in an amount between about 0.25-5% w/w; ethanol in an amount between about 0.25-5% w/w; sodium hydroxide 50% w/v in an amount between about 0.1-5% w/w; Lipmax™ in an amount less than about 20% w/w; and sodium bicarbonate in an amount between about 1-32% w/w.

In some embodiments, a suitable formulation comprises: water in an amount between about 10-80% w/w; Phospholipon® 90 G in an amount between about 0.5-10% w/w; Myritol® 312 in an amount between about 0.5-10% w/w; isopropyl palmitate in an amount between about 0.5-10% w/w; Cetiol® Ultimate in an amount less than about 10% w/w; stearic Acid in an amount between about 0.25-5% w/w; cetyl alcohol in an amount between about 0.25-5% w/w; benzyl alcohol in an amount between about 0.25-5% w/w; propylene glycol in an amount between about 0.25-5% w/w; glycerin in an amount between about 0.25-5% w/w; ethanol in an amount between about 0.25-5% w/w; sodium hydroxide 50% w/v in an amount between about 0.1-5% w/w; and sodium bicarbonate in an amount between about 1-35% w/w.

In some embodiments, a suitable formulation comprises: water in an amount between about 10-40% w/w; Phospholipon® 90H in an amount between about 0.5-20% w/w; Myritol® 312 in an amount between about 0.5-10% w/w; isopropyl palmitate in an amount between about 0.5-20% w/w; Cetiol® Ultimate in an amount less than about 10% w/w; stearic acid in an amount between about 0.25-5% w/w; cetyl alcohol in an amount between about 0.25-5% w/w; benzyl alcohol in an amount between about 0.25-5% w/w; propylene glycol in an amount between about 0.25-5% w/w; glycerin in an amount between about 0.25-5% w/w; ethanol in an amount between about 0.25-5% w/w; sodium hydroxide 50% w/v in an amount between about 0.1-5% w/w; and sodium bicarbonate in an amount between about 1-35% w/w.

In some embodiments, a suitable formulation comprises: water in an amount between about 10-40% w/w; Phospholipon® 90H in an amount between about 0.5-20% w/w; Phospholipon® 90 G in an amount between about 0.5-20% w/w; Myritol® 312 in an amount between about 0.5-10% w/w; isopropyl palmitate in an amount between about 0.5-20% w/w; Cetiol® Ultimate in an amount less than about 10% w/w; stearic acid in an amount between about 0.25-5% w/w; cetyl alcohol in an amount between about 0.25-5% w/w; benzyl alcohol in an amount between about 0.25-5% w/w; propylene glycol in an amount between about 0.25-5% w/w; glycerin in an amount between about 0.25-5% w/w; ethanol in an amount between about 0.25-5% w/w; sodium hydroxide 50% w/v in an amount between about 0.1-5% w/w; and sodium bicarbonate in an amount between about 1-35% w/w.

In some embodiments, a suitable formulation comprises: water in an amount between about 10-50% w/w; Pluronic® gel 30% in an amount between about 5-30% w/w; isopropyl palmitate in an amount between about 0.5-20% w/w; stearic Acid in an amount between about 0.25-10% w/w; cetyl alcohol in an amount between about 0.25-10% w/w; benzyl alcohol in an amount between about 0.25-5% w/w; almond oil in an amount between about 0.5-10% w/w; propylene glycol in an amount between about 0.25-10% w/w; ethanol in an amount between about 0.25-5% w/w; sodium hydroxide 50% w/v in an amount between about 0.1-5% w/w; and sodium bicarbonate in an amount between about 1-32% w/w.

In some embodiments, a suitable formulation comprises: Siligel™ in an amount less than about 5% w/w; water in an amount between about 10-65% w/w; isopropyl palmitate in an amount between about 0.5-10% w/w; stearic Acid in an amount between about 0.25-10% w/w; cetyl alcohol in an amount between about 0.25-10% w/w; glycerin in an amount between about 0.25-5% w/w; Lipmax™ in an amount between about 0.25-10% w/w; ethanol in an amount less than about 5% w/w; benzyl alcohol in an amount less than about 5% w/w; sodium hydroxide 50% w/v in an amount between about 0.1-5% w/w; and sodium bicarbonate in an amount between about 1-32% w/w.

In some embodiments, a suitable formulation comprises: Aveeno® in an amount between about 20-85% w/w; and sodium bicarbonate (3DF) in an amount between about 15-45% w/w.

In some embodiments, a suitable formulation comprises: Aveeno® in an amount between about 20-85% w/w; and sodium bicarbonate (Milled #7) in an amount between about 15-45% w/w.

In some embodiments, a suitable formulation comprises: Siligel™ in an amount less than about 5% w/w; water in an amount between about 10-55% w/w; isopropyl palmitate in an amount between about 0.5-10% w/w; stearic Acid in an amount between about 0.25-5% w/w; Cetyl alcohol in an amount between about 0.25-10% w/w; almond oil in an amount between about 0.5-10% w/w; propylene glycol in an amount between about 0.25-10% w/w; ethanol in an amount less than about 5% w/w; benzyl alcohol in an amount less than about 5% w/w; sodium hydroxide 50% w/v in an amount between about 0.1-5% w/w; and sodium bicarbonate in an amount between about 1-32% w/w.

The surprising effects achieved by the formulations and methods of the present invention are in part attributable to an improved formulation that enhances delivery of a carbonate salt through the skin. In some embodiments, the formulation employs penetrants described US2009/0053290 (290), WO2014/209910 (910), and WO2017/127834. The present formulations may include a nonionic surfactant. Applicant has found that by employing carbonate salts with particle sizes as disclosed herein, delivered with the penetrants as disclosed herein, and in some embodiments providing a combination of a nonionic surfactant and a polar gelling agent, the penetration capabilities of the carbonate salts of the resulting formulation and the effective level of delivery of the carbonate salts has been enhanced. This enhanced level of penetration was also achieved using significantly less lecithin than anticipated or none at all. This result was completely unexpected as it was believed that relatively equal amounts of the benzyl alcohol and lecithin organogel especially a somewhat higher concentration of benzyl alcohol than lecithin organogel were responsible for the level of penetration achieved by prior art formulations.

Briefly, the penetrants described in the above-referenced US and PCT applications are based on combinations of synergistically acting components. Many such penetrants are based on combinations of an alcohol, such as benzyl alcohol to provide a concentration of 0.5-20% w/w of the final formulation with lecithin organogel present in the penetrant to provide 25-70% w/w of the formulation. These penetrants are also useful when the agent is a buffer, such as sodium bicarbonate, but less lecithin organogel may be required—e.g. less than 12% w/w when the sodium bicarbonate is present at high concentration as disclosed herein.

In some embodiments, the buffering component is any mildly basic compound or combination that will result in a pH of 7-8 in the microenvironment of the tumor cells. In some embodiments, the formulation has a pH of 7-10. Such buffers, in addition to carbonate and/or bicarbonate salts, include lysine buffers, chloroacetate buffers, tris buffers (i.e., buffers employing tris (hydroxymethyl) aminoethane), phosphate buffers and buffers employing non-natural amino acids with similar pKa values to lysine. In some embodiments, the carbonate and/or bicarbonate salt is in an amount between about 7-32% w/w of the formulation. For example, the enantiomers of native forms of such amino acids or analogs of lysine with longer or shorter carbon chains or branched forms thereof. Histidine buffers may also be used. Typically, the concentration of buffer in the compositions is in the range of 10-50% w/w. More typical ranges for sodium bicarbonate or sodium carbonate or both are 10-35% by weight. In some embodiments, the carbonate salt is in an amount between about 15-32% w/w of the formulation.

Alternatively, the penetrant component comprises a completion component as well as one or more electrolytes sufficient to impart viscosity and viscoelasticity, one or more surfactants and an alcohol. The completion component can be a polar liquid, a non-polar liquid or an amphiphilic substance.

The percentage of carbonate salt in the formulation will depend upon the amount required to be delivered in order to have a useful effect on treating the disorder. In general, the carbonate salt may be present in the formulation in an amount as low as 1% w/w up to about 50% w/w. Typical concentrations may include 15-32% w/w. Since the required percentage of carbonate salt depends on the frequency of administration, as well as the time allotted for administration for each application, the level of carbonate salt may be varied over a wide range. In some embodiments, the carbonate salt is sodium carbonate and/or sodium bicarbonate milled to a particle size is less than 200 µm. In some embodiments, the carbonate salt is sodium carbonate and/or sodium bicarbonate milled to a particle size is less than 70 µm. In some embodiments, the carbonate salt is sodium carbonate and/or sodium bicarbonate milled to a particle size is less than 70 µm, wherein the sodium bicarbonate is solubilized in the formulation in an amount less than 20% w/w of the formulation. In some embodiments, the carbonate salt is sodium carbonate and/or sodium bicarbonate milled to a particle size is less than 70 µm, wherein particle sizes less than about 10 µm have an enhanced penetration thru the skin of a subject. In some embodiments, the sodium carbonate and/or sodium bicarbonate are jet milled to a particle size less than about 70 µm. In some embodiments, the sodium bicarbonate is Sodium Bicarbonate USP Grade 3DF that has a particle size distribution less than 70 µm.

The formulations of the disclosure may be prepared in a number of ways. Typically, the components of the formulation are simply mixed together in the required amounts. However, it is also desirable in some instances to, for example, carry out dissolution of a carbonate salt and then add a separate preparation containing the components aiding the delivery of the carbonate salts in the form of a carrier. The concentrations of these components in the carrier, then, will be somewhat higher than the concentrations required in the final formulation. Thus, sodium bicarbonate may first be dissolved in water and then added to a carrier comprising an alcohol, lecithin and optionally a combination of a nonionic surfactant and polar gelling agent, or of ionic detergent. Alternatively, some subset of these components can first be mixed and then "topped off" with the remaining components either simultaneously or sequentially. The precise manner of preparing the formulation will depend on the choice of carbonates and the percentages of the remaining components that are desirable with respect to that carbonate salt. In some embodiments, the water is in an amount between about 10-85% w/w, 15-50% w/w, or 15-45% w/w of the formulation.

The penetrant portion is a multi-component mixture, whereby the particular concentrations of the penetration enhancers are informed in part by the molecular mass of the sodium bicarbonate, or sodium bicarbonate and the therapeutic agent to be transported. The formulation enables the sodium bicarbonate and/or therapeutic agent to become bio-available to the target site within minutes of topical administration. The formulations permit the use of minimal concentrations of therapeutic agents, as little as. $\frac{1}{1000}$th of concentrations required of alternative processes, while enabling bioactivity and positive clinical outcomes simultaneously. In some embodiments, the penetrant portion comprises an alcohol in an amount less than 5% w/w of the formulation.

One important aspect of the invention is based on the above-noted recognition that some tumors do not respond to buffer treatment as their microenvironment is not acidic and at least some of these tumors achieve metastasis by elevation of certain proteolytic enzymes that break down the extracellular matrix (ECM). If buffer treatment is contemplated, tumor cells from the biopsy of a solid tumor in a subject are therefore preferably cultured and tested in advance of treatment to insure responsiveness to buffer. Such evaluation can be carried out by any suitable means, including measurement of pH, assessment of the levels of relevant proteases, and invasion assays as impacted by buffer treatment as described in Bailey, K. M. et al (2014) supra. One important such assay is a glycolytic stress assay as described therein. Cell cultures of biopsied tumors that appear not to respond to buffer treatment as shown by such assays may benefit from administration of other antimetastatic agents and inclusion of such agents in the compositions of the invention that include buffers would also be beneficial. Thus, treatment with buffer-containing compositions alone may be contraindicated and the subject is not administered buffer as the sole active agent but diverted to alternative treatment. This does not mean, of course, that buffer is necessarily omitted from formulations used to administer alternative active agents.

The formulations comprise mixtures wherein the components interact synergistically and induce skin permeation enhancements better than that induced by the individual components. Synergies between chemicals can be exploited to design potent permeation enhancers that overcome the efficacy limitations of single enhancers. Several embodiments disclosed herein utilize three to five distinct permeation enhancers.

For topical administration, and in particular transdermal administration, the formulation will comprise penetrants including either or both chemical penetrants (CPEs) and peptide-based cellular penetrating agents (CPPs) that encourage transmission across the dermis and/or across membranes including cell membranes, as would be the case in particular for administration by suppository or intranasal administration, but for transdermal administration as well. Particularly suitable penetrants especially for those that contain at least one agent other than buffer include those that are described in the above-referenced US2009/0053290 (290), WO2014/209910 (910), and WO2017/127834. In addition to formulations with penetrants, transdermal delivery can be affected by mechanically disrupting the surface of the skin to encourage penetration, or simply by supplying the formulation applied to the skin under an occlusive patch.

Alternatively, the penetrant portion comprises a completion component as well as one or more electrolytes sufficient to impart viscosity and viscoelasticity, one or more surfactants and an alcohol. The completion component can be a polar liquid, a non-polar liquid or an amphiphilic substance. The penetrant may further comprise a keratinolytic agent effective to reduce thiol linkages, disrupt hydrogen bonding and/or effect keratin lysis and/or a cell penetrating peptide (sometimes referred to as a skin-penetrating peptide) and/or a permeation enhancer.

Lecithin organogel is a combination of lecithin with a gelling component, which is typically amphiphilic. Suitable gelling components also include isopropyl palmitate, ethyl laurate, ethyl myristate and isopropyl myristate. In some embodiments, the formulation comprises a gelling agent in an amount less than 5% w/w of the formulation. Certain hydrocarbons, such as cyclopentane, cyclooctane, trans-decalin, trans-pinane, n-pentane, n-hexane, n-hexadecane may also be used. Thus, an important permeation agent is a lecithin organogel, wherein the combination resulting from lecithin and the organic solvent acts as a permeation agent. In some embodiments, the penetrant portion comprises lecithin organogel, an alcohol, a surfactant, and a polar solvent. In some embodiments, the lecithin organogel is a combination of soy lecithin and isopropyl palmitate. In some embodiments, the penetrant portion comprises lecithin and isopropyl palmitate, undecane, isododecane, isopropyl stearate, or a combination thereof. In some embodiments, the formulation comprises Lipmax™ (sold by Lucas Meyer Cosmetics) in an amount between about 1-20 w/w or an equivalent 50/50 mixture of isopropyl palmitate and lecithin. Lecithin organogels are clear, thermodynamically stable, viscoelastic, and biocompatible jelly-like phases composed of hydrated phospholipids and appropriate organic liquid. An example of a suitable lecithin organogel is lecithin isopropyl palmitate, which is formed when isopropyl palmitate is used to dissolve lecithin. The ratio of lecithin to isopropyl palmitate may be 50:50. Illustrated below in the Examples is a formulation containing soy lecithin in combination with isopropyl palmitate; however, other lecithins could also be used such as egg lecithin or synthetic lecithins. Various esters of long chain fatty acids may also be included. Methods for making such lecithin organogels are well known in the art. In most embodiments, the lecithin organogel is present in the final formulation is less than about 20% w/w. In those compositions used to dissolve fat deposits, to alleviate pain from fat removal or in anhydrous compositions, the concentration of lecithin organogel may be as low as 0.5% w/w, 1% w/w, 5% w/w, 10% w/w or 20% w/w. In some embodiments, the penetrant portion comprises a mixture of xanthan gum, lecithin, sclerotium gum, pullulan, or a combination thereof in an amount less than 2% w/w, 5% w/w, or 10% w/w of the formulation. In some embodiments, the formulation comprises Siligel™ in an amount between about 1-5% w/w or 5-15% w/w, or an equivalent mixture of xanthan gum, lecithin, sclerotium gum, and pullulan. In some embodiments, the penetrant portion comprises a mixture of caprylic triglycerides and capric triglycerides in amount less than 2% w/w, 8% w/w, or 10% w/w of the formulation. In some embodiments, the formulation comprises Myritol® 312 in an amount between about 0.5-10% w/w, or an equivalent mixture of caprylic triglycerides and capric triglycerides.

In some embodiments, the penetrant portion comprises phosphatidyl choline in amount less than 12% w/w or 18% w/w of the formulation. In some embodiments, the penetrant portion comprises a phospholipid in amount less than 12% w/w or 18% w/w of the formulation. In some embodiments, the penetrant portion comprises a mixture of tridecane and undecane in amount less than 2% w/w, 5% w/w, or 8% w/w of the formulation. In some embodiments, the formulation comprises Cetiol Ultimate® in an amount less than about 2% w/w, 5% w/w, or 10% w/w, or an equivalent mixture of tridecane and undecane. In some embodiments, the penetrant portion comprises cetyl alcohol in amount less than 2% w/w, 5% w/w, or 8% w/w of the formulation. In some embodiments, the penetrant portion comprises benzyl alcohol in an amount less than about 2% w/w, 5% w/w, or 8% w/w. In some embodiments, the penetrant portion comprises stearic acid in an amount less than 2% w/w, 5% w/w, or 8% w/w of the formulation.

Lecithin organogels may be in the form of vesicles, microemulsions and micellar systems. In the form of self-assembled structures, such as vesicles or micelles, they can fuse with the lipid bilayers of the stratum corneum, thereby enhancing partitioning of encapsulated drug, as well as a disruption of the ordered bilayers structure. An example of a phospholipid-based permeation enhancement agent comprises a micro-emulsion-based organic gel defined as a semi-solid formation having an external solvent phase immobilized within the spaces available of a three-dimensional networked structure. This micro-emulsion-based organic gel in liquid phase is characterized by 1,2-diacyl-sn-glycero-3-phosphatidyl choline, and an organic solvent, which is at least one of: ethyl laureate, ethyl myristate, isopropyl myristate, isopropyl palmitate; cyclopentane, cyclooctane, trans-decalin, trans-pinane, n-pentane, n-hexane, n-hexadecane, and tripropylamine.

The lecithin organogels are formulated with an additional component to assist in the formation of micelles or vascular structures. In one approach, the organogels are formulated with a polar component such as water, glycerol, ethyleneglycol or formamide, in particular with water. In general, a nonionic detergent such as a poloxamer in aqueous solution is used to top off. Alternatively, an anhydrous composition may be obtained by using, instead of a polar component, a material such as a bile salt. When formulated with bile salts, the mi cellular nature of the composition is altered so that rather than a more or less spherical vesicular form, the vesicles become wormlike and are able to accommodate larger guest molecules, as well as penetrate the epidermis more effectively. Suitable bile salts include salts of deoxycholic acid, taurocholic acid, glycocholic acid, taurochenodeoxycholic acid, glycochenodeoxycholic acid, cholic acid and the like. Certain detergents, such as Tween® 80 or Span® 80 may be used as alternatives. The percentage of these components in the anhydrous forms of the composition is in the range of 1% w/w-15% w/w. In some embodiments, the range of bile salt content is 2%-6% w/w or 1%-3.5% w/w. In these essentially anhydrous forms, powdered or micronized nonionic detergent is used to top off, typically in amounts of 20%-60% w/w. In one approach to determine the amount of bile salt, the % is calculated by dividing the % w/w of lecithin by 10.

An additional component in the formulations of the disclosure is an alcohol. Benzyl alcohol and ethanol are illustrated in the Examples. in particular, derivatives of benzyl alcohol which contain substituents on the benzene ring, such as halo, alkyl and the like. The weight percentage of benzyl or other related alcohol in the final composition is 0.5-20% w/w, and again, intervening percentages such as 1% w/w, 2% w/w, 5% w/w, 7% w/w, 10% w/w, and other intermediate weight percentages are included. Due to the aromatic group present in a permeation enhancement formulation such as benzyl alcohol, the molecule has a polar end (the alcohol end) and a non-polar end (the benzene end). This enables the agent to dissolve a wider variety of drugs and agents. The alcohol concentration is substantially lower than the concentration of the lecithin organogel in the composition.

In some embodiments, as noted above, the performance of the formulations is further improved by including a nonionic detergent and polar gelling agent or including bile salts and a powdered surfactant. In both aqueous and anhydrous forms of the composition, detergents, typically nonionic detergents are added. In general, the nonionic detergent should be present in an amount of at least 2% w/w to 60% w/w. Typically, in the compositions wherein the formulation is topped off with a polar or aqueous solution containing detergent, the amount of detergent is relatively low—e.g., 2%-25% w/w, or 5-15% w/w or 7-12% w/w. However, in compositions comprising bile salts that are essentially anhydrous and are topped-off by powdered detergent, relatively higher percentages are usually used—e.g., 20%-60% w/w.

In some embodiments, the nonionic detergent provides suitable handling properties whereby the formulations are gel-like or creams at room temperature. To exert this effect, the detergent, typically a poloxamer, is present in an amount between about 2-12% w/w, preferably between about 5-25% w/w in polar formulations. In the anhydrous forms of the compositions, the detergent is added in powdered or micronized form to bring the composition to 100% and higher amounts are used. In compositions with polar constituents, rather than bile salts, the nonionic detergent is added as a solution to bring the composition to I 00%. If smaller amounts of detergent solutions are needed due to high levels of the remaining components, more concentrated solutions of the nonionic detergent are employed. Thus, for example, the percent detergent in the solution may be 10% to 40% or 20% or 30% and intermediate values depending on the percentages of the other components.

Suitable nonionic detergents include poloxamers such as Pluronic® and any other surfactant characterized by a combination of hydrophilic and hydrophobic moieties. Poloxamers are triblock copolymers of a central hydrophobic chain of polyoxypropylene flanked by two hydrophilic chains of polyethyleneoxide. Other nonionic surfactants include long chain alcohols and copolymers of hydrophilic and hydrophobic monomers where blocks of hydrophilic and hydrophobic portions are used.

In some embodiments, the formulation also contains surfactant, typically, nonionic surfactant at 2-25% w/w along with a polar solvent wherein the polar solvent is present in an amount at least in molar excess of the nonionic surfactant. In these embodiments, typically, the composition comprises the above-referenced amounts of lecithin organogel and benzyl alcohol along with a carbonate salt with a sufficient amount of a polar solution, typically an aqueous solution or polyethylene glycol solution that itself contains 10%-40% of surfactant, typically nonionic surfactant to bring the composition to 100%.

Other examples of surfactants include polyoxyethylated castor oil derivatives such as HCO-60 surfactant sold by the HallStar Company; nonoxynol; octoxynol; phenylsulfonate; poloxamers such as those sold by BASF as Pluronic® F68, Pluronic® F127, and Pluronic® L62; polyoleates; Rewopal® HV10, sodium laurate, sodium lauryl sulfate (sodium dodecyl sulfate); sodium oleate; sorbitan dilaurate; sorbitan dioleate; sorbitan monolaurate such as Span® 20 sold by Sigma-Aldrich; sorbitan monooleates; sorbitan trilaurate; sorbitan trioleate; sorbitan monopalmitate such as Span® 40 sold by Sigma-Aldrich; sorbitan stearate such as Span® 85 sold by Sigma-Aldrich; polyethylene glycol nonylphenyl ether such as Synperonic® NP sold by Sigma-Aldrich; p-(1,1,3,3-tetramethylbutyl)-phenyl ether sold as Triton™ X-100 sold by Sigma-Aldrich; and polysorbates such as polyoxyethylene (20) sorbitan monolaurate sold as Tween® 20, polysorbate 40 (polyoxyethylene (20) sorbitan monopalmitate) sold as Tween® 40, polysorbate 60 (polyoxyethylene (20) sorbitan monostearate) sold as Tween® 60, polysorbate 80 (polyoxyethylene (20) sorbitan monooleate) sold as Tween® 80, and polyoxyethylenesorbitan trioleate sold as Tween® 85 by Sigma-Aldrich. The weight percentage range of nonionic surfactant is in the range of 3% w/w-15% w/w, and again includes intermediate percentages such as 5% w/w, 7% w/w, 10% w/w, 12% w/w, and the like. In some embodiments, the detergent portion comprises a nonionic surfactant in an amount between about 2-25% w/w of the formulation; and a polar solvent in an amount less than 5% w/w of the formulation. In some embodiments, the nonionic surfactant is a poloxamer and the polar solvent is water, an alcohol, or a combination thereof. In some embodiments, the detergent portion comprises poloxamer, propylene glycol, glycerin, ethanol, 50% w/v sodium hydroxide solution, or a combination thereof. In some embodiments, the detergent portion comprises glycerin in an amount less than 3% w/w of the formulation.

In the presence of a polar gelling agent, such as water, glycerol, ethyleneglycol or formamide, a micellular structure is also often achieved. Typically, the polar agent is in molar excess of the nonionic detergent. The inclusion of the nonionic detergent/polar gelling agent combination results in a more viscous and cream-like or gel-like formulation which is suitable for application directly to the skin. This is typical of the aqueous forms of the composition.

In some embodiments other additives are included such as a gelling agent, a dispersing agent and a preservative. An example of a suitable gelling agent is hydroxypropylcellulose, which is generally available in grades from viscosities of from about 5 cps to about 25,000 cps such as about 1500 cps. All viscosity measurements are assumed to be made at room temperature unless otherwise stated. The concentration of hydroxypropylcellulose may range from about 1 % w/w to about 2% w/w of the composition. Other gelling agents are known in the art and can be used in place of, or in addition to hydroxypropylcellulose. An example of a suitable dispersing agent is glycerin. Glycerin is typically included at a concentration from about 5% w/w to about 25% w/w of the composition. A preservative may be included at a concentration effective to inhibit microbial growth, ultraviolet light and/or oxygen-induced breakdown of composition components, and the like. When a preservative is included, it may range in concentration from about 0.01% w/w to about 1.5% w/w of the composition.

Typical components that may also be included in the formulations are fatty acids, terpenes, lipids, and cationic, and anionic detergents. In some embodiments, the formulation further comprises tranexamic acid in an amount less than 2% w/w, 5% w/w, or 10% w/w of the formulation. In some embodiments, the formulation further comprises a polar solvent in an amount less than 2% w/w, 5% w/w, 10% w/w, or 20% w/w of the formulation. In some embodiments, the formulation further comprises a humectant, an emulsifier, an emollient, or a combination thereof. In some embodiments, the formulation further comprises ethylene glycol tetraacetic acid in an amount less than about 2% w/w, 5% w/w, or 10% w/w. In some embodiments, the formulation further comprises almond oil in an amount less than about 5% w/w. In some embodiments, the formulation further comprises a mixture of thermoplastic polyurethane and polycarbonate in an amount less than about 5% w/w. In some embodiments, the formulation further comprises phosphatidylethanolamine in an amount less than about 5 w/w. In some embodiments, the formulation further comprises an inositol phosphatide in an amount less than about 5% w/w.

Other solvents and related compounds that may be used in some embodiments include acetamide and derivatives, acetone, n-alkanes (chain length between 7 and 16), alkanols, diols, short chain fatty acids, cyclohexyl-1,1-dimethylethanol, dimethyl acetamide, dimethyl formamide, ethanol, ethanol/d-limonene combination, 2-ethyl-1,3-hexanediol, ethoxydiglycol (Transcutol® by Gattefosse, Lyon, France), glycerol, glycols, lauryl chloride, limonene N-methylformamide, 2-phenylethanol, 3-phenyl-1-propanol, 3-phenyl-2-propen-1-ol, polyethylene glycol, polyoxyethylene sorbitan monoesters, polypropylene glycol 425, primary alcohols (tridecanol), 1,2-propane diol, butanediol, $C_3$-$C_6$ triols or their mixtures and a polar lipid compound selected from $C_{16}$ or $C_{18}$ monounsaturated alcohol, $C_{16}$ or $C_{18}$ branched saturated alcohol and their mixtures, propylene glycol, sorbitan monolaurate sold as Span® 20 by Sigma-Aldrich, squalene, triacetin, trichloroethanol, trifluoroethanol, trimethylene glycol and xylene.

Fatty alcohols, fatty acids, fatty esters, are bilayer fluidizers that may be used in some embodiments. Examples of suitable fatty alcohols include aliphatic alcohols, decanol, lauryl alcohol (dodecanol), unolenyl alcohol, nerolidol, 1-nonanol, n-octanol, and oleyl alcohol. Examples of suitable fatty acid esters include butyl acetate, cetyl lactate, decyl N,N-dimethylamino acetate, decyl N,N-dimethylamino isopropionate, diethyleneglycol oleate, diethyl sebacate, diethyl succinate, diisopropyl sebacate, dodecyl N,N- dimethyamino acetate, dodecyl (N,N-dimethylamino)-butyrate, dodecyl N,N-dimethylamino isopropionate, dodecyl 2-(dimethyamino) propionate, E0-5-oleyl ether, ethyl acetate, ethylaceto acetate, ethyl propionate, glycerol monoethers, glycerol monolaurate, glycerol monooleate, glycerol monolinoleate, isopropyl isostearate, isopropyl linoleate, isopropyl myristate, isopropyl myristate/fatty acid monoglyceride combination, isopropyl palmitate, methyl acetate, methyl caprate, methyl laurate, methyl propionate, methyl valerate, 1-monocaproyl glycerol, monoglycerides (medium chain length), nicotinic esters (benzyl), octyl acetate, octyl N,N-dimethylamino acetate, oleyl oleate, n-pentyl N-acetylprolinate, propylene glycol monolaurate, sorbitan dilaurate, sorbitan dioleate, sorbitan monolaurate, sorbitan monolaurate, sorbitan trilaurate, sorbitan trioleate, sucrose coconut fatty ester mixtures, sucrose monolaurate, sucrose monooleate, tetradecyl N.N-dimethylamino acetate. Examples of suitable fatty acid include alkanoic acids, caprid acid, diacid, ethyloctadecanoic acid, hexanoic acid, lactic acid, lauric acid, linoelaidic acid, linoleic acid, linolenic acid, neodecanoic acid, oleic acid, palmitic acid, pelargonic acid, propionic acid, and vaccenic acid. Examples of suitable fatty alcohol ethers include α-monoglyceryl ether, E0-2-oleyl ether, E0-5-oleyl ether, E0-10-oleyl ether, ether derivatives of poly glycerols and alcohols, and (1-O-dodecyl-3-O-methyl-2-O-(2',3'-dihydroxypropyl glycerol).

Examples of completing agents that may be used in some embodiments include β- and γ-cyclodextrin complexes, hydroxypropyl methylcellulose (e.g., Carbopol® 934), liposomes, naphthalene diamide diimide, and naphthalene diester diimide.

One or more anti-oxidants may be included, such as vitamin C, vitamin E, proanthocyanidin and a-lipoic acid typically in concentrations of 0.1%-2.5% w/w.

In some applications, it is desirable to adjust the pH of the formulation to assist in permeation or to adjust the nature of the carbonate and/or of the target compounds in the subject. In some instances, the pH is adjusted to a level of pH 9-11 or 10-11 which can be done by providing appropriate buffers or simply adjusting the pH with base.

In some applications, in particular when the therapeutic agent includes an anesthetic, epinephrine or an alternate vasoconstrictor, such as phenylephrine or epinephrine sulfate may be included in the formulation if a stabilizing agent is present. Otherwise, the epinephrine should be administered in tandem since epinephrine is not stable at alkali pH.

In any of the anesthetic compositions, it may be desirable to administer the epinephrine in tandem with the transdermal anesthetic. Alternatively, treatment of the epinephrine with a chelator, such as the iron chelator Desferal® may stabilize the epinephrine sufficiently to include it in the transdermal formulation.

It is understood that some tumors do not respond to treatment with buffer, but apparently metastasize by virtue of elevated levels of proteases that attack the extracellular matrix surrounding the tumor. In any event, breakdown of the ECM would encourage metastasis. Therefore, an additional active agent that is optionally included in the compositions of the invention is one or more appropriate protease inhibitors. Particularly important are inhibitors of cathepsins, for example of cathepsin B, and inhibitors of matrix metalloproteinases (MMPs). These components are active alone or augment the effect of buffer for tumors that are not resistant to buffer treatment.

The formulations may include other components that act as excipients or serve purposes other than active anti-tumor effects. For example, preservatives like antioxidants e.g., ascorbic acid or α-lipoic acid and antibacterial agents may be included. Other components apart from therapeutically active ingredients and components that are the primary effectors of dermal penetration may include those provided for aesthetic purposes such as menthol or other aromatics, and components that affect the physical state of the composition such as emulsifiers, for example, Durasoft® (which is a mixture of thermoplastic polyurethane and polycarbonate). Typically, these ingredients are present in very small percentages of the compositions. It is understood that these latter ancillary agents are neither therapeutically ingredients nor are they components that are primarily responsible for penetration of the skin. The components that primarily effect skin penetration have been detailed as described above. However, some of these substances have some capability for effecting skin penetration. See, for example, Kunta, J. R. et al, *J. Pharm. Sci.* (1997) 86:1369-1373, describing penetration properties of menthol.

In embodiments where a bile salt is added to the combination of benzyl alcohol and lecithin organogel in lieu of topping off with an aqueous medium, micelles that would have been relatively spherical may become elongated and worm-like thus permitting superior penetration of the stratum corneum of the epidermis. The worm like formation of the micelles is particularly helpful in accommodating higher molecular weight therapeutic agents. As is known, bile salts are facial amphiphiles and include salts of taurocholic acid, glycocholic acid, taurochenodeoxycholic acid, glycochenodeoxycholic acid, cholic acid, deoxycholic acid. Detergents are also useful in lieu of bile salts and include Tween® 80 and Span® 80.

In another aspect, certain embodiments are directed to a sustained release drug delivery platform releases a therapeutic compound or compounds disclosed and made as a formulation described herein over a period of, without limitation, about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. In other aspects of this embodiment, a sustained release drug delivery platform releases a therapeutic compound or compounds disclosed herein with substantially first order release kinetics over a period of, without limitation, at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.

The formulation described in this specification may also comprise more than one therapeutic compound as desired for the particular indication being treated, preferably those with complementary activities that do not adversely affect the other proteins. The formulations to be used for in vivo administration can be sterile. This can be accomplished, for instance, without limitation, by filtration through sterile filtration membranes, prior to, or following, preparation of the formulation or other methods known in the art, including without limitation, pasteurization.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

In certain embodiments, kits can comprise, without limitation, one or more cream or lotion comprising one or more formulations described herein. In various embodiments, the kit can comprise formulation components for transdermal, topical, or subcutaneous administration, formulated to be administered as an emulsion coated patch. In all of these embodiments and others, the kits can contain one or more lotion, cream, patch, or the like in accordance with any of the foregoing, wherein each patch contains a single unit dose for administration to a subject.

Imaging components can optionally be included and the packaging also can include written or web-accessible instructions for using the formulation. A container can include, for example, a vial, bottle, patch, syringe, pre-filled syringe, tube or any of a variety of formats well known in the art for multi-dispenser packaging.

Administration and Dosing

The formulations provided herein can be topically administered in any form. For administration for the treatment of skin conditions a sufficient amount of the topical composition can be applied onto a desired area and surrounding skin, for example, in an amount sufficient to cover a desired area plus a margin of healthy skin or tissue surrounding the desired area, if possible, for example, a margin of about 0.5 inches. A desired area can be an area of the skin affected by skin disorder in some embodiments. However, in other embodiments a desired area of the skin may be unaffected or healthy, e.g. skin not having any disorder or condition. Also, the formulations can be applied to any skin surface, including for example, facial skin, and the skin of the hands, neck, chest and/or scalp.

For administration for the treatment of conditions that are not skin disorders, such as cancer and related disorders, gout, bladder and kidney stones and the like, there is usually no particular afflicted area of the patient's skin and it is often desirable to administer the formulations provided herein to several skin surfaces of the patient or a large surface area to increase the amount of lotion applied.

In applying the formulations of the invention, the formulation itself is simply placed on the skin and spread across the surface and/or massaged to aid in penetration. The amount of formulation used is typically sufficient to cover a desired surface area. In some embodiments, a protective cover is placed over the formulation once it is applied and left in place for a suitable amount of time, i.e., 5 minutes, 10 minutes, 20 minutes or more; in some embodiments an hour or two. The protective cover can simply be a bandage including a bandage supplied with a cover that is impermeable to moisture. This essentially locks in the contact of the formulation to the skin and prevents distortion of the formulation by evaporation in some cases. The composition may be applied to the skin using standard procedures for application such as a brush, a syringe, a gauze pad, a dropper, or any convenient applicator. More complex application methods, including the use of delivery devices, may also be used, but are not required. In an alternative to administering topically to intact skin, the surface of the skin may also be disrupted mechanically by the use of spring systems, laser powered systems, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed formulations that penetrate intact skin may be applied using occlusive patches, such as those in the form micro-patches. External reservoirs of the formulations for extended administration may also be employed.

In an alternative to administering topically to intact skin, the surface of the skin may also be disrupted mechanically by the use of spring systems, laser powered systems, use of iontophoresis, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed formulations that penetrate intact skin may be applied using occlusive patches, such as those in the form micro-patches. External reservoirs of the formulations for extended administration may also be employed.

Accordingly, in certain embodiments alternative methods of administering one or more buffering agent, therapeutic compounds, agents, drugs through intact skin are provided. As nonlimiting examples, these alternative methods might be selected from the following lists: on basis of working mechanism, spring systems, laser powered, energy-propelled, Lorentz force, gas/air propelled, shock wave (including ultrasound), on basis of type of load, liquid, powder, projectile, on basis of drug delivery mechanism, nanopatches, sandpaper (microdermabrasion), iontophoresis enabled, microneedles, on basis of site of delivery, intradermal, intramuscular, and subcutaneous injection. Other suitable delivery mechanisms include, without limitation, microneedle drug delivery, such as 3M Systems, Glide SDI (pushes drug as opposed to "firing" drug), MIT low pressure injectors, micropatches (single use particle insertion device), microelectro mechanical systems (MEMS), dermoelectroporation devices (DEP), transderm ionto system (DEP), TTS transdermal therapeutic systems, membrane-moderated systems (drug reservoir totally encapsulated in a shallow compartment), adhesive diffusion-controlled system (drug reservoir in a compartment fabricated from drug-impermeable metallic plastic backing), matrix dispersion type system (drug reservoir formed by homogeneously dispersing drug solids in a hydrophilic or lipophilic polymer matrix molder into medicated disc), and microreservoir system (combination of reservoir and matrix dispersion-type drug delivery system).

It has been found, generally, that the requirements for effective penetration of the skin in the case of buffers as active agents are less restrictive than those required for alternative agents useful in preventing cancer metastasis. In addition, although for these indications delivery to the locus of the solid tumor, including melanoma, or melasma or gout is desirable, effective systemic pH alteration can be used as a way to diagnose the effectiveness of penetration when topical administration is employed.

The application method is determined by the nature of the treatment but may be less critical than the nature of the formulation itself. If the application is to a skin area, it may be helpful in some instances to prepare the skin by cleansing or exfoliation. In some instances, it is helpful to adjust the pH of the skin area prior to application of the formulation itself. The application of the formulation may be by simple massaging onto the skin or by use of devices such as syringes or pumps. Patches could also be used. In some cases, it is helpful to cover the area of application to prevent evaporation or loss of the formulation.

Where the application area is essentially skin, it is helpful to seal-off the area of application subsequent to supplying the formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

In some embodiments, the disclosure is directed to administering a local anesthetic to a subject transdermally and a formulation which contains an effective amount of anesthetic along with 25%-70% w/w or 30%-60% w/w or 30%-40% w/w of lecithin organogel typically wherein the lecithin organogel comprises soy lecithin in combination with isopropyl palmitate or isopropyl myristate and benzyl alcohol in the range of 0.5%-20% w/w or 0.9%-2% w/w benzyl alcohol optionally including 1%-5% w/w or 2%-4% w/w menthol wherein the composition is topped off with a polar solution, typically an aqueous solution comprising 15%-50% w/w or 20%-40% w/w or 20%-30% w/w poloxamer, typically Pluronic® or alternatively may be an anhydrous composition comprising bile salts such as deoxycholic acid or sodium deoxycholate in the range of 4%-8% w/w, typically 6% w/w and the remainder of the composition powdered nonionic detergent, typically Pluronic®. The pH of the compositions is adjusted to 9-11, typically 10-11. The formulations are applied to the desired area of the skin and may be covered, for example, with Saran™ wrap for a suitable amount of time. Following the treatment, the skin can be repaired by applying a composition comprising linoleic acid.

A wide variety of therapeutic agents may be used in the formulations, including anesthetics, fat removal compounds, nutrients, nonsteroidal anti-inflammatory drugs (NSAIDs) agents for the treatment of migraine, hair growth modulators, antifungal agents, anti-viral agents, vaccine components, tissue volume enhancing compounds, anti-cellulite therapeutics, wound healing compounds, compounds useful to effect smoking cessation, agents for prevention of collagen shrinkage, wrinkle relief compounds such as Botox®, skin-lightening compounds, compounds for relief of bruising, cannabinoids including cannabidiols for the treatment of epilepsy, compounds for adipolysis, compounds for the treatment of hyperhidrosis, acne therapeutics, pigments for skin coloration for medical or cosmetic tattooing, sunscreen compounds, hormones, insulin, corn/callous removers, wart removers, and generally any therapeutic or prophylactic agent for which transdermal delivery is desired. As noted above, the delivery may simply affect transport across the skin into a localized subdermal location, such as treatment of nail fungus or modulation of hair growth or may effect systemic delivery such as is desirable in some instances where vaccines are used.

In addition to the compositions and formulations of the invention per se, the methods may employ a subsequent treatment with linoleic acid. As transdermal treatments generally open up the skin barrier, which is, indeed, their purpose, it is useful to seal the area of application after the treatment is finished. Thus, treatment with the formulation may be followed by treating the skin area with a composition comprising linoleic acid to seal off the area of application. The application of linoleic acid is applicable to any transdermal procedure that results in impairing the ability of the skin to act as a protective layer. Indeed, most transdermal treatments have this effect as their function is to allow carbonates to pass through the epidermis to the dermis at least, and, if systemic administration is achieved, through the dermis itself.

For administration of anesthetics as the therapeutic agent, the local anesthetic may be one or more of the following: benzocaine, lidocaine, tetracaine, bupivacaine, cocaine, etidocaine, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Combinations of anesthetic agents may also be used. The anesthetic agent{s) are included in the composition in effective amount(s). Depending on the anesthetic(s) the amounts of anesthetic or combination is typically in the range of 1 w/w to 50% w/w. The compositions of the invention provide rapid, penetrating relief that is long lasting. The pain to be treated can be either traumatic pain and/or inflammatory pain.

In one embodiment, the anesthetic is administered to relieve the pain associated with invasive fat deposit removal. Specific removal of fat deposits has been attractive for both health and cosmetic reasons. Among the methods employed are liposuction and injection of a cytolytic agent for fat such as deoxycholic acid (DCA). For example, a series of patents issued or licensed to Kythera Biopharmaceuticals is directed to methods and compositions for non-surgical removal of localized fat that involves injecting compositions containing DCA or a salt thereof. Representative issued patents are directed to formulation (U.S. Pat. No. 8,367,649); method-of-use (U.S. Pat. Nos. 8,846,066; 7,622,130; 7,754,230; 8,298,556); and synthetic DCA (U.S. Pat. No. 7,902,387).

In this aspect of the invention, conventional invasive fat removal techniques are employed along with administering a pain-relieving effective agent—typically lidocaine or related anesthetics via transdermal administration. In some embodiments, the pain-relieving transdermal formulation is applied to the area experiencing pain immediately before, during or immediately after the invasive fat-removal procedure.

Additional therapeutic agents may be included in the compositions. For example, hydrocortisone or hydrocortisone acetate may be included in an amount ranging from 0.25% w/w to about 0.5% w/w. Menthol, phenol, and terpenoids, e.g., camphor, can be incorporated for cooling pain relief. For example, menthol may be included in an amount ranging from about 0.1% w/w to about 1.0% w/w.

The compositions containing anesthetics are useful for temporary relief of pain and itching associated with minor burns, cuts, scrapes, skin irritations, inflammation and rashes due to soaps, detergents or cosmetics, or, as noted above, pain associated with removal of fat deposits.

The benefits of alkaline pH include higher penetration capability and adjustment of the active form of the fat dissolving compound when the anesthetic is used in conjugation therewith. For example, the pKa of the deoxycholic acid is 6.58 and the pH of fat is neutral. When deoxycholic acid (DCA) is injected without buffering, it is approximately an equilibrium between the protonated and unprotonated forms. Utilizing formulations with high pH buffering shifts the balance significantly to unprotonated form making the DCA more water soluble and more likely to emulsify fats.

The formulations can be applied in a single, one-time application, once a week, once a bi-week, once a month, or from one to twelve times daily, for a period of time sufficient to alleviate a condition, disease, disorder, symptoms, for example, for a period of time of one week, from 1 to 12 weeks or more, from 1 to 6 weeks, from 2 to 12 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day to hourly if needed. The presently described formulations can be topically administered once or more per day for a period of time from 1 week to 4 weeks, of from 1 week to 2 weeks, for 1 week, for 2 weeks, for 3 weeks, for 4 weeks, or for 4 weeks or more. In some instances, it may also be desirable to continue treatment indefinitely for example to inhibit or prevent carcinogenesis or for improving, extending the duration of remission, or maintaining remission of a cancer or another disease or disorder. A suitable administration for a formulation comprising a skin cream, lotion or ointment, for example is once, twice, three, four times daily, or hourly if needed.

The formulations provided herein can be applied in a therapeutically effective amount. Suitable amounts, for example, per application can include, for example, from about 1 gram to about 500 grams; from about 1 gram to about 10 grams; from about 10 grams to about 25 grams; from about 10 grams to about 50 grams; from about 10 grams to about 100 grams; from about 10 grams to about 200 grams; from about 10 grams to about 350 grams; from about 10 grams to about 500 grams; from about 20 grams to about 500 grams; from about 20 grams to about 350 grams; from about 20 grams to about 200 grams; from about 20 grams to about 100 grams; from about 20 grams to about 90 grams; from about 20 grams to about 80 grams; from about 20 grams to about 70 grams; from about 20 grams to about 60 grams; from about 20 grams to about 50 grams; from about 30 grams to about 100 grams; from about 30 grams to about 80 grams; from about 30 grams to about 70 grams; or from about 30 grams to about 60 grams. Alternatively, suitable amounts, for example, per application can include, for example, at least 5 grams; at least 10 grams; at least 15 grams; at least 20 grams; at least 25 grams; at least 30 grams; at least 35 grams; at least 40 grams; at least 50 grams; at least 55 grams; at least 60 grams; at least 65 grams; at least 70 grams; at least 75 grams; at least 80 grams; at least 85 grams; at least 90 grams; at least 100 grams; or more.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

A formulation in accordance with the subject matter described herein may be a topical dosage form packaged in, for example, a multi-use or single-use package, including for example, a tube, a tottle, a pump, a container or bottle, a vial, a jar, a packet, or a blister package.

Single dosage kits and packages containing a once per day amount of the topical formulation may be prepared. Single dose, unit dose, and once-daily disposable containers of the topical formulation are also provided.

The present topical formulation remains stable in storage for periods including up to about 5 years, between about 3 months and about 5 years, between about 3 months and about 4 years, between about 3 months and about 3 years, and alternately any time period between about 6 months and about 3 years.

A topical formulation described herein remains stable for up to at least 3 years at a temperature of less than or equal to 40° C. In an embodiment, the presently described topical formulation remains stable for at least 2 years at a temperature of less than or equal to 40° C. In an embodiment, the presently described formulation or emulsion remains stable for at least 3 years at a temperature of less than or equal to 40° C. and at a humidity of up to 75% RH, for at least 2 years at a temperature of less than or equal to 40° C. and at a humidity of up to 75% RH, or for at least 3 years at a temperature of less than or equal to 30° C. and at a humidity of up to 75% RH. In a further embodiment, the presently described biocompatible composition in accordance with the subject matter described herein remains stable for an extended period of time when packaged in a multi-use container such as a bottle dispenser or the like, and exhibits equal to or even greater stability when packaged in a single-use package.

In another aspect, the pharmaceutical composition of certain embodiments comprises a daily dose of a pH modulating composition or buffer (e.g. sodium bicarbonate as a topical formulation). A daily dose for topical or transdermal administration of any given pH modulating compound depends on the compound and animal and may be easily determined by the skilled artisan, a suitable amount is about 1 mg/kg to about 5 g/kg, and more typically the daily dose is about 10 mg/kg to about 5 g/kg, about 25 mg/kg to about 2000 mg/kg, about 50 mg/kg to about 2000 mg/kg, about 25 mg/kg to about 1000 mg/kg, about 50 mg/kg to about 1000 mg/kg, about 100 mg/kg to about 700 mg/kg, about 100 mg/kg to about 500 mg/kg, about 150 mg/kg to about 500 mg/kg, about 150 mg/kg to about 400 mg/kg, about 200 mg/kg to about 500 mg/kg, about 200 mg/kg to about 450 mg/kg, about 200 mg/kg to about 400 mg/kg, about 250 mg/kg to about 450 mg/kg, about 250 mg/kg to about 400 mg/kg, about 250 mg/kg to about 350 mg/kg, and about 275 mg/kg to about 325 mg/kg.

Alternatively, a suitable daily dose for topical or transdermal administration of a pH modulating composition or buffer (e.g. sodium bicarbonate) is at least about 1 mg/kg, at least about 10 mg/kg, at least about 25 mg/kg, at least about 30 mg/kg, at least about 35 mg/kg, at least about 40 mg/kg, at least about 41 mg/kg, at least about 42 mg/kg, at least about 43 mg/kg, at least about 44 mg/kg, at least about 45 mg/kg, at least about 46 mg/kg, at least about 47 mg/kg, at least about 48 mg/kg, at least about 49 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 90 mg/kg, at least about 100 mg/kg, at least about 125 mg/kg, at least about 150 mg/kg, at least about 160 mg/kg, at least about 170 mg/kg, at least about 175 mg/kg, at least about 180 mg/kg, at least about 190 mg/kg, at least about 200 mg/kg, at least about 225 mg/kg, at least about 250 mg/kg, at least about 275 mg/kg, at least about 300 mg/kg, at least about 325 mg/kg, at least about 350 mg/kg, at least about 375 mg/kg, at least about 400 mg/kg, at least about 425 mg/kg, at least about 450 mg/kg, at least about 475 mg/kg, at least about 500 mg/kg, at least about 550 mg/kg, at least about 600 mg/kg, at least about 700 mg/kg, at least about 800 mg/kg, at least about 900 mg/kg, at least about 1 g/kg, at least about 2 g/kg, at least about 3 g/kg, or at least about 5 g/kg.

Alternatively, a suitable dose for topical or transdermal administration of a pH modulating formulation or buffer (e.g. sodium bicarbonate) for subject (e.g. a human patient) is at least about 100 mg, at least about 500 mg, at least about 1 g, at least about 5 g, at least about 10 g, at least about 15 g, at least about 16 g, at least about 17 g, at least about 18 g, at least about 19 g, at least about 20 g, at least about 21 g, at least about 22 g, at least about 23 g, at least about 24 g, at least about 25 g, at least about 26 g, at least about 27 g, at least about 28 g, at least about 29 g, at least about 30 g, at least about 35 g, at least about 40 g, at least about 45 g, at least about 50 g, at least about 60 g, at least about 75 g, at least about 100 g, at least about 200 g, at least about 500 g, or at least about 1.0 kg. This does may be administered daily, twice a day, three times a day, four times a day, five times a day, or more than five times a day.

In another aspect, in certain embodiments a pH modulating composition or buffer (e.g. sodium bicarbonate) is administered topically or transdermally such that the dose results in a subject intake of at least about 0.1 nmol/hr/Kg, at least about 0.5 nmol/hr/Kg, at least about 0.7 nmol/hr/Kg, at least about 1.0 nmol/hr/Kg, at least about 1.1 nmol/hr/Kg, at least about 1.2 nmol/hr/Kg, at least about 1.3 nmol/hr/Kg, at least about 1.4 nmol/hr/Kg, at least about 1.5 nmol/hr/Kg, at least about 1.6 nmol/hr/Kg, at least about 1.7 nmol/hr/Kg, at least about 1.8 nmol/hr/Kg, at least about 1.9 nmol/hr/Kg, at least about 2.0 nmol/hr/Kg, at least about 2.5 nmol/hr/Kg, at least about 3.0 nmol/hr/Kg, at least about 3.5 nmol/hr/Kg, at least about 4.0 nmol/hr/Kg, at least about 5 nmol/hr/Kg, at least about 10 nmol/hr/Kg, at least about 25 nmol/hr/Kg, at least about 50 nmol/hr/Kg, at least about 100 nmol/hr/Kg, at least about 500 nmol/hr/Kg, or at least about 1 nmol/hr/Kg, In another aspect, in certain embodiments a pH modulating composition or buffer (e.g. sodium bicarbonate) is administered topically or transdermally such that the dose results in a peak plasma concentration of a buffering or pH modulating compound ranges from about 1 µg/ml to 50 µg/ml, about 5 µg/ml to about 45 µg/ml, about 5 µg/ml to about 40 µg/ml, about 5 µg/ml to about 35 µg/ml, about 5 µg/ml to about 30 µg/ml, about 5 µg/ml to about 25 µg/ml, about 1 µg/ml to about 45 µg/ml, about 1 µg/ml to about 40 µg/ml, about 1 µg/ml to about 35 µg/ml, about 1 µg/ml to about 30 µg/ml, about 1 µg/ml to about 25 µg/ml, about 1 µg/ml to about 20 µg/ml, about 1 µg/ml to about 15 µg/ml, about 1 µg/ml to about 10 µg/ml, about 1 µg/ml to about 9 µg/ml, about 1 µg/ml to about 8 µg/ml, about 1 µg/ml to about 7 µg/ml, about 1 µg/ml to about 6 µg/ml, and about 1 µg/ml to about 5 µg/ml.

In another aspect, in certain embodiments a pH modulating composition or buffer (e.g. sodium bicarbonate) is administered topically or transdermally so that plasma concentration ranges from about 1 ng/ml to 500 µg/ml, about 10 ng/ml to 500 µg/ml, about 100 ng/ml to 500 µg/ml, about 1 µg/ml to 500 µg/ml, about 10 µg/ml to 500 µg/ml, about 25 µg/ml to 500 µg/ml, about 25 µg/ml to about 450 µg/ml, about 25 µg/ml to about 400 µg/ml, about 25 µg/ml to about 350 µg/ml, about 25 µg/ml to about 300 µg/ml, about 25 µg/ml to about 250 µg/ml, about 50 µg/ml to about 500 µg/ml, about 55 µg/ml to about 500 µg/ml, about 60 µg/ml to about 500 µg/ml, about 65 µg/ml to about 500 µg/ml, about 70 µg/ml to about 500 µg/ml, about 75 µg/ml to about 500 µg/ml, about 80 µg/ml to about 500 µg/ml, about 85 µg/ml to about 500 µg/ml, about 90 µg/ml to about 500 µg/ml, about 95 µg/ml to about 500 µg/ml, about 100 µg/ml to about 500 µg/ml, about 110 µg/ml to about 500 µg/ml, about 120 µg/ml to about 500 µg/ml, about 130 µg/ml to about 500 µg/ml, about 140 µg/ml to about 500 µg/ml about 150 µg/ml to about 500 µg/ml, about 160 µg/ml to about 500 µg/ml, about 170 µg/ml to about 500 µg/ml, about 180 µg/ml to about 500 µg/ml, about 200 µg/ml to about 500 µg/ml, about 200 µg/ml to about 490 µg/ml, about 200 µg/ml to about 480 µg/ml, about 200 µg/ml to about 470 µg/ml, about 200 µg/ml to about 460 µg/ml, about 200 µg/ml to about 450 µg/ml, about 200 µg/ml to about 440 µg/ml, about 200 µg/ml to about 430 µg/ml, or about 200 µg/ml to about 400 µg/ml.

In further embodiments, a pH modulating composition or buffer (e.g. sodium bicarbonate) is administered topically or transdermally so that plasma concentration is at least 10 ng/ml, at least 25 ng/ml, at least 50 ng/ml, at least 100 ng/ml, at least 250 ng/ml, at least 0.5 µg/ml, at least 0.75 µg/ml, at least 1 µg/ml, at least 2 µg/ml, at least 3 µg/ml, at least 4 µg/ml, at least 5 µg/ml, at least 6 µg/ml, at least 7 µg/ml, at least 8 µg/ml, at least 9 µg/ml, at least 10 µg/ml, at least 15 µg/ml, at least 20 µg/ml, at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 80 µg/ml, at least 85 µg/ml, at least 90 µg/ml, at least 95 µg/ml, at least 100 µg/ml or more than 100 µg/ml.

In another aspect, a pH modulating compound or buffer (e.g. sodium bicarbonate) is administered topically or transdermally so that peak plasma concentration is reached in 10 min, 15 min, 20 min, 30 min, 45 min, 60 min, 75 min, 90 min, 2 hr, 3 hr, 4 hr, 5 hr, 6 hr, 7 hr, 8 hr, 10 hr, 12 hr or 24 hr after administration.

Aspects of the present specification disclose that the symptoms associated with a disease or disorder described herein are reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with a disease or disorder described herein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms associated with disease or disorder are reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The formulations as described herein can be used in the manufacture of medicaments and for the treatment of humans and other animals by administration in accordance with conventional procedures.

EXPERIMENTAL EXAMPLES

The compositions and methods described herein will be further understood by reference to the following examples, which are intended to be purely exemplary. The compositions and methods described herein are not limited in scope by the exemplified embodiments, which are intended as illustrations of single aspects only. Any methods that are functionally equivalent are within the scope of the invention. Various modifications of the compositions and methods described herein in addition to those expressly described herein will become apparent to those skilled in the art from the foregoing description and accompanying figures. Such modifications fall within the scope of the invention.

The following examples are intended to illustrate but not to limit the invention.

Example 1—Specific Formulations for Administration of Buffering Agents

The following compositions have been prepared and are found useful in the methods of the invention. In the tables below, "LIP" represents lecithin organogel comprised of a 1:1 molar mixture of soy lecithin containing 96% phosphatidyl choline and isopropyl palmitate; "BA" represents benzyl alcohol; PLU-F127 represents the detergent poloxamer F127 granules; PLU-Water represents PLU-F127 dissolved in deionized water. (Alternatively, commercially available Pluronic F127 30% gel could be used) and Durasoft® is a commercially available form of emulsifier.

In the tables below, sodium bicarbonate and sodium carbonate were supplied as such. Tris buffer at pH 8.1 was used. The phosphate "buffer" was supplied as Na $H_2PO_4$. The percentages are wt/wt i.e., weight percentages.

TABLE 1

Bicarbonate Formulations

|  | IB | IIB |
| --- | --- | --- |
| LIP | 30.00% | 25.00% |
| Ethanol | 1.50% | 0.00% |
| BA | 1.00% | 1.00% |
| Menthol | 0.50% | 0.90% |
| NaBicarbonate | 33.50% | 5.76% |
| PLU-F127 | 10.05% | 10.50% |
| Water in gel with PLU | 23.45% | 24.50% |
| Additional Water |  | 30.34% |
| Durasoft |  | 2.00% |
| TOTAL | 100.00% | 100.00% |

TABLE 2

Carbonate Formulations

|  | IC | IIC | IIIC | IVC |
| --- | --- | --- | --- | --- |
| LIP | 25.00% | 25.00% | 30.00% | 40.00% |
| Ethanol | 0.00% | 0.00% | 1.50% | 1.50% |
| BA | 1.00% | 1.00% | 1.00% | 1.00% |
| Menthol | 0.90% | 0.90% | 0.50% | 0.50% |
| Sodium Carbonate | 9.36% | 16.10% | 33.50% | 11.00% |
| PLU-F127 | 10.50% | 10.00% | 10.05% | 13.50% |
| Water in gel with PLU | 24.50% | 23.33% | 23.45% | 31.53% |
| Additional Water | 26.74% | 22.67% | 0.00% | 0.00% |
| Durasoft | 2.00% | 1.00% | 0.00% | 1.00% |
| TOTAL | 100.00% | 100.00% | 100.00% | 100.00% |

TABLE 3

Tris Formulations

|  | IT | IIT | IIIT | IVT |
| --- | --- | --- | --- | --- |
| LIP | 25.00% | 25.00% | 30.00% | 38.40% |
| Ethanol | 0.00% | 0.00% | 1.50% | 1.50% |
| BA | 1.00% | 1.00% | 1.00% | 1.00% |
| Menthol | 0.90% | 0.90% | 0.50% | 0.50% |
| TRIS buffer, pH 8.1 | 13.37% | 23.00% | 33.50% | 14.93% |
| PLU-F127 | 10.50% | 10.00% | 10.05% | 12.80% |
| Water in gel with PLU | 24.50% | 23.33% | 23.45% | 29.87% |
| Additional Water | 27.73% | 15.77% | 0.00% | 0.00% |
| Durasoft | 2.00% | 1.00% | 0.00% | 1.00% |
| TOTAL | 100.00% | 100.00% | 100.00% | 100.00% |

TABLE 4

Phosphate Formulations

|  | IP | IIP | III | IVP |
| --- | --- | --- | --- | --- |
| LIP | 25.00% | 25.00% | 30.00% | 37.25% |
| Ethanol | 0.00% | 0.00% | 1.50% | 1.50% |
| BA | 1.00% | 1.00% | 1.00% | 1.00% |
| Menthol | 0.90% | 0.90% | 0.50% | 0.50% |
| Monosodium phosphate | 16.02% | 27.55% | 33.50% | 17.36% |
| PLU-F127 | 10.50% | 10.00% | 10.05% | 12.42% |
| Water in gel with PLU | 24.50% | 23.33% | 23.45% | 28.97% |
| Additional Water | 20.08% | 11.22% | 0.00% | 0.00% |
| Durasoft | 2.00% | 1.00% | 0.00% | 1.00% |
| TOTAL | 100.00% | 100.00% | 100.00% | 100.00% |

TABLE 5

Carbonate, TRIS, Phosphate Combination Formulations

|  | Phos — low | Phos — high | III | IV |
| --- | --- | --- | --- | --- |
| LIP | 25.00% | 25.00% | 30.00% | 37.25% |
| Ethanol | 0.00% | 0.00% | 1.50% | 1.50% |
| BA | 1.00% | 1.00% | 1.00% | 1.00% |
| Menthol | 0.90% | 0.90% | 0.50% | 0.50% |
| Sodium Carbonate | 5.30% | 5.30% | 5.30% | 5.30% |
| TRIS (121.14) | 6.00% | 6.00% | 6.00% | 6.00% |
| Monosodium phosphate | 6.00% | 6.00% | 6.00% | 6.00% |
| PLU-F127 | 10.50% | 10.00% | 10.05% | 12.42% |
| Water in gel with PLU | 24.50% | 23.33% | 23.45% | 28.97% |
| Additional Water | 12.14% | 21.47% | 16.20% | 0.06% |
| DURASOFT | 2.00% | 1.00% | 0.00% | 1.00% |
| TOTAL | 100.00% | 100.00% | 100.00% | 100.00% |

TABLE 6

Alternative Buffers

| | 25 | 28 | 29 | A(2) | B(2) | C(2) |
|---|---|---|---|---|---|---|
| LIP | 6.00% | 12.00% | 12.00% | 14.00% | 15.00% | 18.00% |
| BA | 1.00% | 1.00% | 1.00% | 1.00% | 1.00% | 1.00% |
| Menthol | 0.50% | 0.50% | 0.50% | 0.25% | 0.25% | 0.50% |
| Durasoft | | | | 1.50% | 1.50% | 1.00% |
| Pluronic Granules | 4.20% | 4.20% | 4.20% | 5.40% | 2.10% | 3.60% |
| Water | 37.80% | 37.80% | 40.30% | 31.60% | 29.65% | 41.90% |
| Sodium Carbonate | 7.00% | 7.00% | 7.00% | — | — | 3.00% |
| Sodium Bicarbonate | 28.00% | 28.00% | 28.00% | 32.50% | 32.50% | 15.00% |
| propylene glycol | 3.00% | 3.00% | | 6.00% | 10.00% | 5.00% |
| almond oil | 3.00% | 3.00% | 3.00% | 4.00% | 3.00% | 4.50% |
| zinc oxide | | | | 0.25% | 0.50% | |
| cetyl alcohol | 2.00% | 2.00% | 2.00% | 2.00% | 3.00% | 3.00% |
| lecithin | 3.00% | | | | | |
| cetiol ultimate (mixture of tridecane and ethanol | 1.50% | 1.50% | 1.50% | 1.50% | 1.50% | 1.50% |
| EGTA | | | 0.50% | | | 1.00% |
| Sodium Decanoate | | | | | | 1.00% |
| TOTAL | 100.00% | 100.00% | 100.00% | 100.00% | 100.00% | 100.00% |

TABLE 7

Anhydrous Formulations

| | 26 | 27 | 30 |
|---|---|---|---|
| menthol | 0.20% | 0.20% | 0.50% |
| Ethanol | 2.00% | 2.00% | 1.50% |
| Benzyl Alcohol | 8.00% | 8.00% | 1.00% |
| Cetyl Alcohol | | | 2.00% |
| Almond Oil | 5.00% | 5.00% | 3.00% |
| Lecithin | 15.90% | 15.90% | 6.00% |
| Lipmax | 15.90% | 15.90% | 6.00% |
| Propylene Glycol | 3.00% | 3.00% | 0.00% |
| F127 Pluronic Powder | 16.00% | 16.00% | 4.20% |
| Water | | | 39.80% |
| Sodium Bicarbonate | 26.00% | 0.00% | 28.00% |
| Sodium Carbonate | 7.00% | 33.00% | 7.00% |
| Durasoft | 1.00% | 1.00% | 1.00% |
| | 100.00% | 100.00% | 100.00% |

Example 2—Topical Administration of Bicarbonate

24 NCR nude 5 week old male mice were used in this study, divided into four groups of six mice each. Topical compositions were applied to the back of each mouse from hip to shoulder three times per day for 8 successive days for a total of 24 applications. A control group was administered sodium bicarbonate in water by mouth. The groups are as follows:

Group 1. Sodium bicarbonate in H$_2$0
Group 2. transdermal bicarbonate Dose #1 (30 μL)(10 μL × 3 doses)
Group 3. transdermal bicarbonate Dose #2 (220 μL)(73 μL × 3 doses)
Group 4. transdermal bicarbonate Dose #3 (1110 μL)
(2 ×185 μL × 3 doses)

The transdermal formulations comprise penetrants to result in the formulations as follows: LIP-30.0%, EtOH-1.5%, BA-1.0%, menthol-0.5%, sodium bicarbonate-33.5%, PLU-F127-10.1%, PLU-water-23.5%; i.e., Formulation IB in Table 1. The concentration of sodium bicarbonate in the control group was 200 mM and the consumption was ad libidum. The concentration of sodium bicarbonate in the transdermal formulations was 33.5% wt/wt.

Urine samples were collected at one hour, three hours and six hours after the first drug application and stored at 4° C. for subsequent pH determination. On days 2-12 urine was collected twice daily—prior to the first application and 15 minutes after the last application. The mice were sacrificed one hour after the last drug application on day 8 and the back skin was harvested and placed on bibulous paper.

To set a base line for pH without dosing, prior to beginning the protocol, urinary pH was measured at three time points during a single day in seven mice at 0900, five mice at 1300 and four mice at 1630. The pH of the urine had an overall mean value of 5.57 which did not vary over this time period.

As shown in FIG. 1, all of the groups showed an increase in urine pH over the first six hours of treatment. The most significant increase occurred in Group 3 which was administered 220 microliters of the formulation.

Although the study was designed to be conducted for two weeks (Mon-Fri), it was terminated after day eight because the members of Group 2 (1,110 microliter) developed skin irritation; this was shown even in the low dose group receiving 30 microliters, i.e., Group 2.

Figure 2:
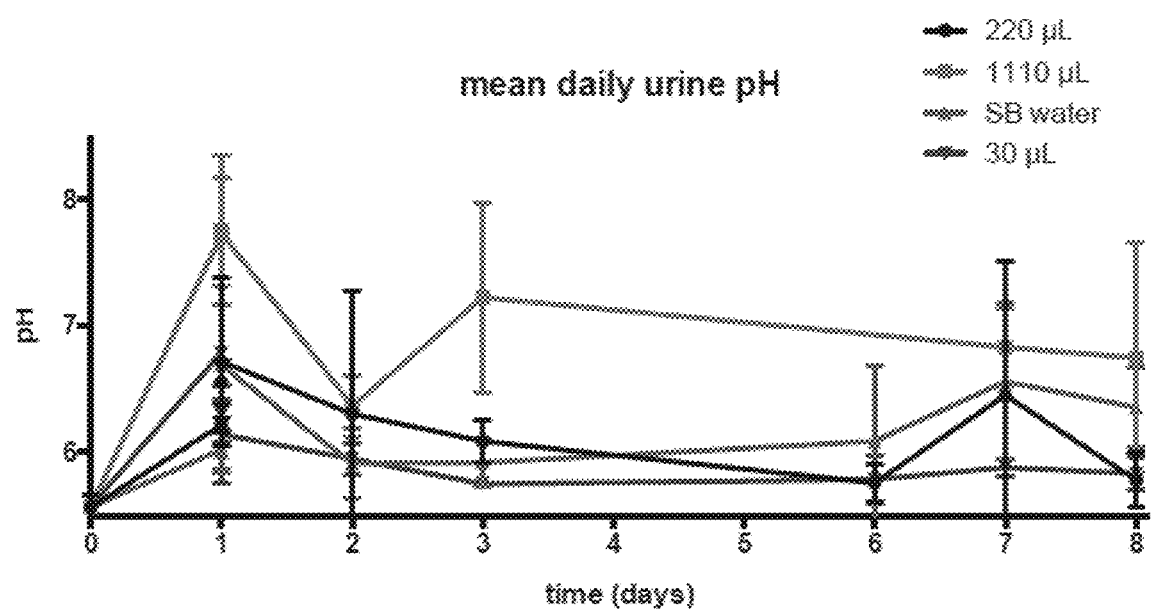
FIG. 2 shows the mean daily urine pH of experimental subjects as a function of time after administration of a formulation of sodium bicarbonate in the formulations and dosages of FIG. 1.

FIG. 2 shows the urine values of pH over the course of the eight day study. Although there was some variation, the group receiving the highest dosage (Group 4) was able to maintain a high pH over the course of the study.

Figure 3:
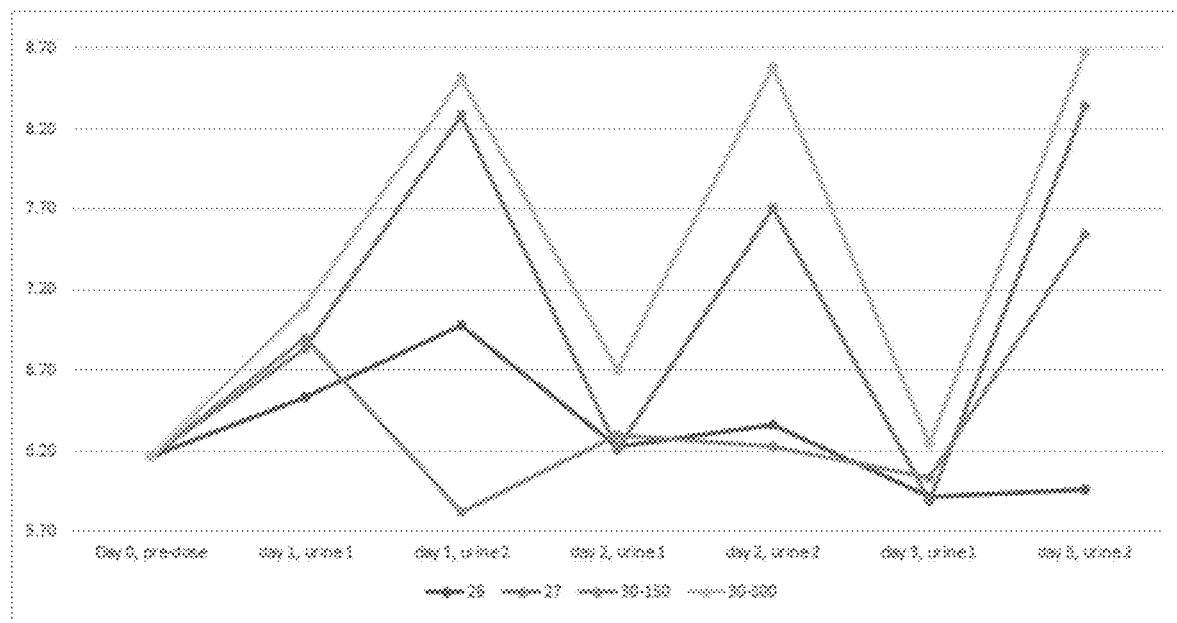
FIG. 3 shows the time course of urine pH over a 3-day period using alternative topical formulations.

The study was repeated using the formulations 25, 28 and 29 in Table 6 with the results shown in Table 8 and using the formulations in Table 7 with results shown in FIG. 3.

TABLE 8

Mean urine pH at two collection time points on day one and overall.

| | urine 1 | urine 2 | overall |
|---|---|---|---|
| SB water | 6.30 | 6.03 | 6.15 |
| 25 | 6.36 | 6.77 | 6.62 |
| 28 | 6.92 | 6.86 | 6.89 |
| 29 | 6.82 | 7.31 | 6.97 |

As shown, transdermal administration was more effective than oral administration.

Example 3—Transdermal Absorption in Humans

Healthy human Subjects Aged 18-60 were enrolled in a double-blinded, placebo controlled, randomized and crossover in designed study. The subjects applied 0.6 g/kg of body weight of formulation of Table 9, per randomization group, as follows: legs from ankle to top of thighs; arms from wrist to shoulder (including the deltoids) or drank 0.13 ounces of water per kg bodyweight (equates to about 8 ounces for a 140 pound subject) at 15 min, 1 hr 15 min, 2 hours and 15 min, 3 hours and 15 mins to control for dilution of urine.

TABLE 9

| | |
|---|---|
| LIP | 30.0% |
| Ethanol | 1.5% |
| BA | 1.0% |
| Menthol or limonene for lipophilic) | 0.5% |
| NaBicarbonate | 33.5% |
| PLU-F127 | 10.1% |
| PLU-Water | 23.5% |

At hourly intervals (at 1, 2, 3, and 4 hours) from start time of application, subjects collected 10-20 ml (approximately a Tablespoon) of urine and the pH was determined. The results are shown in Table 10.

TABLE 10

Average Urine pH values for each treatment and time point

| Product | Baseline (n = 20) | 1 hour (n = 20) | 2 hours (n = 20) | 3 hours (n = 19) | 4 hours (n = 20) |
|---|---|---|---|---|---|
| Control (oral) | 5.75 | 5.95 | 6.01 | 6.08 | 6.01 |
| Formulation | 5.86 | 6.11 | 6.27 | 6.24 | 6.23 |

No adverse effects were shown and the transdermal formulation out-performed oral administration.

Example 4—Treatment of Gout in Humans

A randomized, double-blinded, placebo controlled study of the efficacy and safety of a topical alkalinizing treatment for reducing pain associated with an acute gout flare was conducted to determine if topical application of sodium bicarbonate and menthol in a transdermal delivery system can effectively and safely reduce pain associated with an acute gout flare and if time to resolution is shortened.

40 subjects with a past history of gout and presenting in the clinic with a gout attack that started within 36 hours and who had been prescribed colchicine, aged 18+ were employed randomized into groups of 20.

The formulations used are shown in Table 11.

TABLE 11

Gout Formulations

| Ingredient | Control | Active |
|---|---|---|
| Menthol | 0.00% | 0.50% |
| Ethanol | 1.50% | 1.50% |
| Benzyl Alcohol | 1.00% | 1.00% |
| Cetyl Alcohol | 2.00% | 2.00% |
| Almond Oil | 3.00% | 3.00% |
| Lecithin | 10.00% | 7.00% |
| IPP | 10.00% | 7.00% |
| Propylene Glycol | 5.00% | 5.00% |
| Poloxamer/Pluronic Powder | 9.00% | 5.40% |
| Water | 57.50% | 33.60% |
| Sodium Bicarbonate | 0.00% | 33.00% |
| Durosoft PK-SG | 1.00% | 1.00% |
| | 100.00% | 100.00% |

Subjects applied 10 ml of Control or Active cream to the entire limb of each affected joint three times a day. One identified "target joint" and up to 2 additional joints were followed.

The subjects reported joint pain as measured using a 11-point scale (0-10, with 0 as "no pain" and 10 as "worst possible pain"). The reduction in pain in the target joints for the Active group (two subjects) was −3.0 points both after 30 minutes and 24 hours and −3.5 points at 4 days and 6 days Subjects in the ControlGroup showed no reduction at 30 minutes and 2 days and only −1 point after 24 hours and at 4 and 6 days. The maximum reduction in pain in a secondary joint for the Active group was −2 points, versus less or no reduction in pain for the Control group.

The reduction in pain associated with Active product use was observed as early as 15 minutes after product application.

A follow-up study was performed. This study was double-blinded, randomized, placebo controlled, and parallel group design. Forty subjects, female and male, aged 18+, with a clinical diagnosis of gout, history of uric acid >6.8 mg/dl, on stable medication regimen, presenting in the clinic within 36 hours of initiation of acute gout attack and prescribed colchicine were included. The key exclusion criteria for the study included >stage 3 kidney disease, tophaceous gout, and recent/concurrent initiation of other pain medications (e.g. NSAID, corticosteroids).

Subjects were randomized to receive placebo lotion or sodium bicarbonate transdermal lotion (33% sodium bicarbonate and 0.5% menthol) and instructed to apply to the entire limb of up to three affected joints (a target joint and up to two other joints). Outcome measures included pain using a numeric rating scale (0-10), time to resolution (defined as 50% reduction in pain) range of motion and satisfaction with the treatment. Time-points were baseline, 15 & 30 min, and 1, 2, 4, 6, 8, 10, 12, and 14 days.

Figure 4:
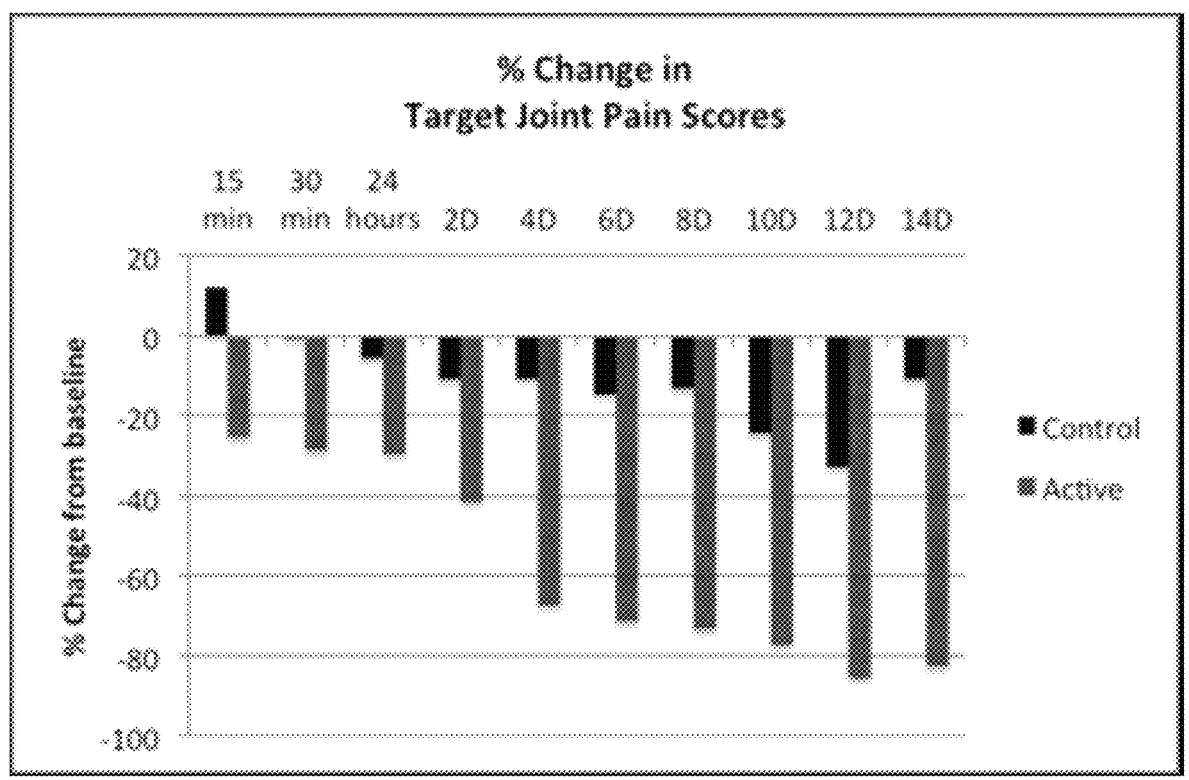
FIG. 4 shows the % change in target joint pain scores measured starting at 15 min and over a 14 day period.
Figure 5:
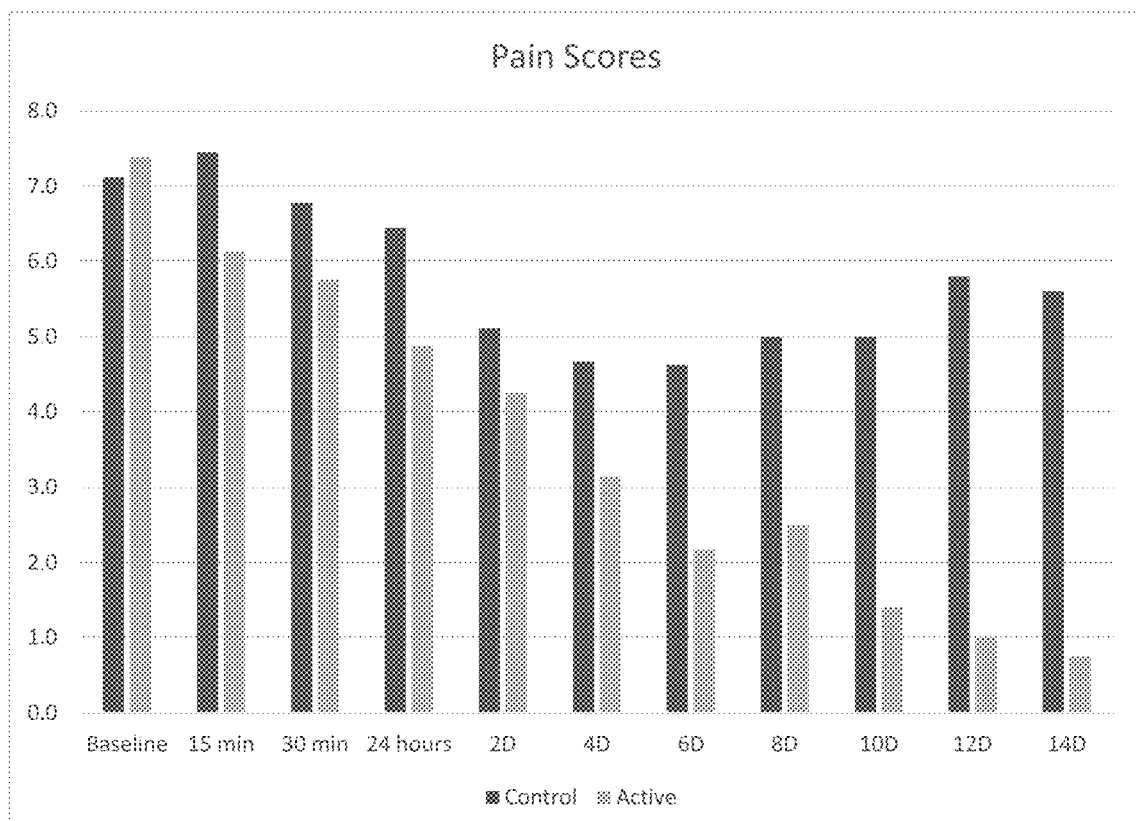
FIG. 5 shows the target joint pain scores on a scale of 0-8, measured starting at 15 min and over a 14 day period.

The data was analyzed for 5 control and 4 active subjects. FIG. 4 shows the % reduction in pain scores over time in the target joint. A similar effect was observed for other involved joints. Pain resolution was not reached by 3 control subjects, but was an average of 7 days in the two who resolved. All subjects in the active group resolved, with the average being 3.25 days. Range of motion improvement at the last time-point collected was 50% for control and 100% for active. Subject satisfaction was 67% reporting 'Neutral' and 33% 'Satisfied' in control and 67% 'Extremely Satisfied' and 33% 'Neutral' for active. No treatment related adverse events were reported. The data indicates that topical transdermal delivery of sodium bicarbonate in a lotion form as provided herein may safely and significantly reduce pain, as early as 15 min, and speed resolution of acute gout attacks. FIG. 5 shows the target joint pain scores from zero to 8, measured starting at 15 min and over a 14 day period.

Subjective pain scores of multiple joints that were identified as 'target joints' were collected from patients in response to treatment to measure effectiveness. Target joints are identified by the characteristics of level of pain, pain experience similar to previous gout attacks, etc. Target joints included the left ankle, left metatarsophalangeal joint, left great toe, right knee, left 1st MTP, right 1st MTP, left $4^{th}$ MT joint, right wrist, left elbow, left hand interphalangeal joints, left knee, right foot, right wrist, right $4^{th}$ TMT, and left 1st MTP and pain of these joints was measured in response to treatment of a patient.

TABLE 12

Gout joint pain measurements.

| | Baseline_joint_A | Target joint Baseline | D1_target_pain_15 | D1_target_joint_pain_30 | D1_target_joint_pain_24 hr |
|---|---|---|---|---|---|
| Group A | | | | | |
| Group A | Left Ankle | 9 | 9 | 9 | 8 |
| Group A | Left Metatarsophalangeal joint | 5 | 5 | 5 | 5 |
| Group A | Left Ankle | 8 | 8 | 6 | 6 |
| Group A | Left great toe | 5 | 8 | 6 | 7 |
| Group A | Right Knee | 6 | 6 | 5 | 5 |
| Group A | Left ankle | 8 | 8 | 8 | 7 |
| Group A | Left 1st MTP | 7 | 7 | 7 | 5 |
| Group A | R 1st MTP | 7 | 8 | 7 | 7 |
| Group A | Left 4th MT joint | 9 | 8 | 8 | 8 |
| | Average | 7.1 | 7.4 | 6.8 | 6.4 |
| Group B | Right Wrist | 5 | 4 | 4 | 4 |
| Group B | Left elbow | 6 | 2 | 1 | 1 |
| Group B | Left hand Interphalangeal joints | 10 | 8 | 8 | 8 |
| Group B | LEFT KNEE | 5 | 5 | 4 | 3 |
| Group B | Right foot | 6 | 6 | 5 | 4 |
| Group B | Right Wrist | 8 | 6 | 6 | 6 |
| Group B | Right 4th TMT | 9 | 9 | 9 | 8 |
| Group B | L 1st MTP | 10 | 9 | 9 | 5 |
| | Average | 7.4 | 6.1 | 5.8 | 4.9 |

| | Baseline_joint_A | D2_target_joint_pain | D4_target_joint_pain | D6_target_joint_pain | D8_target_joint_pain |
|---|---|---|---|---|---|
| Group A | | | | | |
| Group A | Left Ankle | 9 | 8 | 8 | 8 |
| Group A | Left Metatarsophalangeal joint | 5 | 5 | 4 | 5 |
| Group A | Left Ankle | 6 | 7 | 7 | 8 |
| Group A | Left great toe | 6 | 6 | 6 | 6 |
| Group A | Right Knee | 5 | 5 | 5 | 6 |
| Group A | Left ankle | 4 | 4 | 4 | 2 |
| Group A | Left 1st MTP | 4 | 3 | 0 | |
| Group A | R 1st MTP | 6 | 4 | 3 | 0 |
| Group A | Left 4th MT joint | 1 | 0 | | |
| | Average | 5.1 | 4.7 | 4.6 | 5.0 |
| Group B | Right Wrist | 3 | 2 | 2 | 1 |
| Group B | Left elbow | 2 | 2 | 2 | 2 |

TABLE 12-continued

Gout joint pain measurements.

| | | | | | |
|---|---|---|---|---|---|
| Group B | Left hand Interphalangeal joints | 4 | 3 | 3 | 2 |
| Group B | LEFT KNEE | 3 | 3 | 2 | 3 |
| Group B | Right foot | 5 | 5 | | 5 |
| Group B | Right Wrist | 6 | | | |
| Group B | Right 4th TMT | 7 | 5 | 4 | 2 |
| Group B | L 1st MTP | 4 | 2 | 0 | |
| | Average | 4.3 | 3.1 | 2.2 | 2.5 |

| | | Baseline_joint_A | D10_target_joint_pain | D12_target_joint_pain | D14_target_joint_pain |
|---|---|---|---|---|---|
| Group A | | | | | |
| Group A | Left Ankle | | 7 | 8 | 8 |
| Group A | Left Metatarsophalangeal joint | | 4 | 2 | 4 |
| Group A | Left Ankle | | 8 | 7 | 7 |
| Group A | Left great toe | | 6 | 6 | 5 |
| Group A | Right Knee | | 5 | 6 | 4 |
| Group A | Left ankle | | 0 | | |
| Group A | Left 1st MTP | | | | |
| Group A | R 1st MTP | | | | |
| Group A | Left 4th MT joint | | | | |
| | Average | | 5.0 | 5.8 | 5.6 |
| Group B | Right Wrist | | 1 | 0 | 0 |
| Group B | Left elbow | | 2 | 2 | 2 |
| Group B | Left hand Interphalangeal joints | | 2 | 0 | 0 |
| Group B | LEFT KNEE | | 2 | 2 | 1 |
| Group B | Right foot | | | | |
| Group B | Right Wrist | | | | |
| Group B | Right 4th TMT | | 0 | | |
| Group B | L 1st MTP | | | | |
| | Average | | 1.4 | 1.0 | 0.8 |

Pain scores (0-10 scale with 0 being no pain and 10 being the worst possible pain) were collected from patients at the time points indicated following treatment of the entire limb that the target joint is located on with a transdermal buffer formulation with 0.5% menthol or a control formulation (same base without the buffer or menthol).

TABLE 13

Gout joint pain measurements. Table 13 presents the same data as Table 13 and adds the % change from baseline for each timepoint.

| | | Baseline_joint_A | Target joint Baseline | D1_target_pain_15 | Absolute Change 15 min | % charge 15 min |
|---|---|---|---|---|---|---|
| Group A | | | | | | |
| Group A | Left Ankle | | 9 | 9 | 0.00 | 0.00 |
| Group A | Left Metatarsophalangeal joint | | 5 | 5 | 0.00 | 0.00 |

TABLE 13-continued

Gout joint pain measurements. Table 13 presents the same data as Table 13 and adds the % change from baseline for each timepoint.

| | | | | | |
|---|---|---|---|---|---|
| Group A | Left Ankle | 8 | 8 | 0.00 | 0.00 |
| Group A | Left great toe | 5 | 8 | 0.00 | 0.00 |
| Group A | Right Knee | 6 | 6 | 0.00 | 0.00 |
| Group A | Left ankle | 8 | 8 | 0.00 | 0.00 |
| Group A | Left 1st MTP | 7 | 7 | 0.00 | 0.00 |
| Group A | R 1st MTP | 7 | 8 | 0.00 | 0.00 |
| Group A | left 4th MT joint | 9 | 8 | 0.00 | 0.00 |
| | Average | 7.1 | 7.4 | 0.0 | 0.0 |
| Group B | Right wrist | 5 | 4 | 0.00 | 0.00 |
| Group B | Left elbow | 5 | 2 | 0.00 | 0.00 |
| Group B | Lefthand Interphalangeal joints | 10 | 8 | 0.00 | 0.00 |
| Group B | LEFT KNEE | 5 | 5 | 0.00 | 0.00 |
| Group B | Right foot | 6 | 6 | 0.00 | 0.00 |
| Group B | Right Wrist | 8 | 6 | 0.00 | 0.00 |
| Group B | Right 4th TMT | 9 | 9 | 0.00 | 0.00 |
| Group B | L 1stMTP | 10 | 9 | 0.00 | 0.00 |
| | Average | 7.4 | 6.1 | 0.00 | 0.00 |

| | | Baseline_joint_A | D1_target_joint_pain_30 | Absolute Change 30 min | % change 30 min | D1_target_joint_pain_24 hr |
|---|---|---|---|---|---|---|
| Group A | | | | | | |
| Group A | Left Ankle | | 9 | 0.00 | 0.00 | 8 |
| Group A | Left Metatarsophalangeal joint | | 5 | 0.00 | 0.00 | 5 |
| Group A | Left Ankle | | 6 | −2.00 | −25.00 | 6 |
| Group A | Left great toe | | 6 | −2.00 | −25.00 | 7 |
| Group A | Right Knee | | 5 | −1.00 | −16.67 | 5 |
| Group A | Left ankle | | 8 | 0.00 | 0.00 | 7 |
| Group A | Left 1st MTP | | 7 | 0.00 | 0.00 | 5 |
| Group A | R 1st MTP | | 7 | −1.00 | −12.50 | 7 |
| Group A | left 4th MT joint | | 8 | 0.00 | 0.00 | 8 |
| | Average | | 6.8 | −0.7 | −8.8 | 6.4 |
| Group B | Right wrist | | 4 | 0.00 | 0.00 | 4 |
| Group B | Left elbow | | 1 | −1.00 | −50.00 | 1 |
| Group B | Lefthand Interphalangeal joints | | 6 | 0.00 | 0.00 | 8 |
| Group B | LEFT KNEE | | 4 | −1.00 | −20.00 | 3 |
| Group B | Right foot | | 5 | −1.00 | −16.67 | 4 |
| Group B | Right Wrist | | 6 | 0.00 | 0.00 | 6 |
| Group B | Right 4th TMT | | 9 | 0.00 | 0.00 | 8 |
| Group B | L 1stMTP | | 9 | 0.00 | 0.00 | 5 |
| | Average | | 5.8 | −0.38 | −10.83 | 4.9 |

TABLE 13-continued

Gout joint pain measurements. Table 13 presents the same data as Table 13 and adds the % change from baseline for each timepoint.

|  | Baseline_joint_A | D1 Absolute change | % change D1 | D2_target_joint_pain | D2 absolute change |
|---|---|---|---|---|---|
| Group A |  |  |  |  |  |
| Group A | Left Ankle | −1.00 | −11.11 | 9 | 0.00 |
| Group A | Left Metatarsophalangeal joint | 0.00 | 0.00 | 5 | 0.00 |
| Group A | Left Ankle | −2.00 | −25.00 | 6 | −2.00 |
| Group A | Left great toe | −1.00 | −12.50 | 6 | −2.00 |
| Group A | Right Knee | −1.00 | −16.67 | 5 | −1.00 |
| Group A | Left ankle | −1.00 | −12.50 | 4 | −4.00 |
| Group A | Left 1st MTP | −2.00 | −28.57 | 4 | −3.00 |
| Group A | R 1st MTP | −1.00 | −12.50 | 6 | −2.00 |
| Group A | left 4th MT joint | 0.00 | 0.00 | 1 | −7.00 |
|  | Average | −1.0 | −13.2 | 5.1 | −2.8 |
| Group B | Right wrist | 0.00 | 0.00 | 3 | −1.00 |
| Group B | Left elbow | −1.00 | −50.00 | 2 | 0.00 |
| Group B | Lefthand Interphalangeal joints | 0.00 | 0.00 | 4 | −4.00 |
| Group B | LEFT KNEE | −2.00 | −40.00 | 3 | −2.00 |
| Group B | Right foot | −2.00 | −33.33 | 5 | −1.00 |
| Group B | Right Wrist | 0.00 | 0.00 | 6 | 0.00 |
| Group B | Right 4th TMT | −1.00 | −11.11 | 7 | −2.00 |
| Group B | L 1stMTP | −4.00 | −44.41 | 4 | −5.00 |
|  | Average | −1.25 | −22.36 | 4.3 | −1.88 |

|  | Baseline_joint_A | D2 % change | D4_target_joint_pain | D4 absolute change | D4 % change |
|---|---|---|---|---|---|
| Group A |  |  |  |  |  |
| Group A | Left Ankle | 0.00 | 8 | −1.00 | −11.11 |
| Group A | Left Metatarsophalangeal joint | 0.00 | 5 | 0.00 | 0.00 |
| Group A | Left Ankle | −25.00 | 7 | −1.00 | −12.50 |
| Group A | Left great toe | −25.00 | 6 | −2.00 | −25.00 |
| Group A | Right Knee | −16.67 | 5 | −1.00 | −16.67 |
| Group A | Left ankle | −50.00 | 4 | −4.00 | −50.00 |
| Group A | Left 1st MTP | −42.86 | 3 | −4.00 | −57.14 |
| Group A | R 1st MTP | −25.00 | 4 | −4.00 | −50.00 |
| Group A | left 4th MT joint | −67.50 | 0 | −8.00 | −100.00 |
|  | Average | −30.2 | 4.7 | −2.8 | −35.8 |
| Group B | Right wrist | −25.00 | 2 | −2.00 | −50.00 |
| Group B | Left elbow | 0.00 | 2 | 0.00 | 0.00 |
| Group B | Lefthand Interphalangeal joints | −50.00 | 3 | −5.00 | −62.50 |
| Group B | LEFT KNEE | −40.00 | 3 | −2.00 | −40.00 |
| Group B | Right foot | −16.67 | 5 | −1.00 | −16.67 |
| Group B | Right Wrist | 0.00 |  |  |  |

TABLE 13-continued

Gout joint pain measurements. Table 13 presents the same data as Table 13 and adds the % change from baseline for each timepoint.

| | | | | |
|---|---|---|---|---|
| Group B Right 4th TMT | −22.22 | 5 | −4.00 | −44.44 |
| Group B L 1stMTP | −55.56 | 2 | −7.00 | −77.78 |
| Average | −26.18 | 3.1 | −3.00 | −41.63 |

| Baseline_joint_A | D6_target_joint_pain | D6 absolute change | D6 % change | D8_target_joint_pain |
|---|---|---|---|---|
| Group A | | | | |
| Group A Left Ankle | 8 | −1.00 | −11.11 | 8 |
| Group A Left Metatarsophalangeal joint | 4 | −1.00 | −20.00 | 5 |
| Group A Left Ankle | 7 | −1.00 | −12.50 | 8 |
| Group A Left great toe | 6 | −2.00 | −25.00 | 6 |
| Group A Right Knee | 5 | −1.00 | −16.67 | 6 |
| Group A Left ankle | 4 | −4.00 | −50.00 | 2 |
| Group A Left 1st MTP | 0 | −7.00 | −100.00 | |
| Group A R 1st MTP | 3 | −5.00 | −62.50 | 0 |
| Group A left 4th MT joint | | | | |
| Average | 4.6 | −2.8 | −37.2 | 5.0 |
| Group B Right wrist | 2 | −2.00 | −50.00 | 1 |
| Group B Left elbow | 2 | 0.00 | 0.00 | 2 |
| Group B Lefthand Interphalangeal joints | 3 | −5.00 | −62.50 | 2 |
| Group B LEFT KNEE | 2 | −3.00 | −60.00 | 3 |
| Group B Right foot | | | | 5 |
| Group B Right Wrist | | | | |
| Group B Right 4th TMT | 4 | −5.00 | −55.56 | 2 |
| Group B L 1stMTP | 0 | −9.00 | −100.00 | |
| Average | 2.2 | −4.00 | −54.68 | 2.5 |

| Baseline_joint_A | D8 absolute change | D8 % change | D10_target_joint_pain | D10 absolute change |
|---|---|---|---|---|
| Group A | | | | |
| Group A Left Ankle | −1.00 | −11.11 | 7 | −2.00 |
| Group A Left Metatarsophalangeal joint | 0.00 | 0.00 | 4 | −1.00 |
| Group A Left Ankle | 0.00 | 0.00 | 8 | 0.00 |
| Group A Left great toe | −2.00 | −25.00 | 6 | −2.00 |
| Group A Right Knee | 0.00 | 0.00 | 5 | −1.00 |
| Group A Left ankle | −6.00 | −75.00 | 0 | −8.00 |
| Group A Left 1st MTP | | | | |
| Group A R 1st MTP | −8.00 | −100.00 | | |
| Group A left 4th MT joint | | | | |
| Average | −2.4 | −30.2 | 5.0 | −2.3 |
| Group B Right wrist | −3.00 | −75.00 | 1 | −3.00 |
| Group B Left elbow | 0.00 | 0.00 | 2 | 0.00 |
| Group B Lefthand Interphalangeal joints | −6.00 | −75.00 | 2 | −6.00 |

TABLE 13-continued

Gout joint pain measurements. Table 13 presents the same data as Table 13 and adds the % change from baseline for each timepoint.

| | | | | | |
|---|---|---|---|---|---|
| Group B | LEFT KNEE | −2.00 | −40.00 | 2 | −3.00 |
| Group B | Right foot | −1.00 | −16.67 | | |
| Group B | Right Wrist | | | | |
| Group B | Right 4th TMT | −7.00 | −77.78 | 0 | −9.00 |
| Group B | L 1stMTP | | | | |
| | Average | −3.17 | −47.41 | 1.4 | −4.20 |

| | Baseline_joint_A | D10 % change | D12_target_joint_pain |
|---|---|---|---|
| Group A | | | |
| Group A | Left Ankle | −22.22 | 8 |
| Group A | Left Metatarso-phalangeal joint | −20.00 | 2 |
| Group A | Left Ankle | 0.00 | 7 |
| Group A | Left great toe | −25.00 | 6 |
| Group A | Right Knee | −16.67 | 6 |
| Group A | Left ankle | −100.00 | |
| Group A | Left 1st MTP | | |
| Group A | R 1st MTP | | |
| Group A | left 4th MT joint | | |
| | Average | −30.6 | 5.8 |
| Group B | Right wrist | −75.00 | 0 |
| Group B | Left elbow | 0.00 | 2 |
| Group B | Lefthand Interphalangeal joints | −75.00 | 0 |
| Group B | LEFT KNEE | −60.00 | 2 |
| Group B | Right foot | | |
| Group B | Right Wrist | | |
| Group B | Right 4th TMT | −100.00 | |
| Group B | L 1stMTP | | |
| | Average | −62.00 | 1.0 |

Example 5—Treatment of Melasma in Humans

A randomized, double-blind study was conducted evaluating tranexamic acid in a transdermal delivery system, alone or with skin turnover agents for improvement of melasma to evaluate the efficacy and safety of 1) tranexamic acid (TA), 2) TA and 5% glycolic acid (GA) and 3) TA used in combination with retinoic acid (RA) to control for the improvement of melasma. All the formulations including Control are alkaline. The formulations used are shown in Table 14.

TABLE 14

Melasma Formulations

| Ingredient | Control | Active (TA) | Active (TA + CA) |
|---|---|---|---|
| Tranexamic Acid | 0.000% | 6.000% | 6.000% |
| Glycolic Acid | 0.000% | 0.000% | 5.000% |
| Sodium Carbonate | 1.060% | 1.000% | 1.000% |
| Triethanolamine | 0.000% | 0.000% | 1.000% |
| Lecithin | 13.300% | 12.500% | 12.500% |
| IPP | 13.300% | 12.500% | 12.500% |
| Benzyl Alcohol | 1.060% | 1.000% | 1.000% |
| Durosoft PK-SG | 1.060% | 1.000% | 1.000% |
| Poloxamer/Pluronic Powder | 9.255% | 8.700% | 6.900% |
| Water | 60.745% | 57.100% | 52.900% |
| Crisp Fruit Fragrance | 0.220% | 0.200% | 0.200% |
| | 100.000% | 100.000% | 100.000% |

36 women aged 18-65 with moderate to severe melasma were divided into groups of 12 each, and the subjects applied the formulations twice daily at the site of the melasma. The Groups are as follows: Group 1: Control; Group 2: Tranexamic acid (TA) 6% Formulation; Group 3: TA 6%+Glycolic Acid 5% (GA) Combined Formulation; Group 4: TA 6% Formulation and Retinoic Acid 0.25% (RA) (separate products, with TA applied immediately before RA).

Outcome measures were by Standardized 2D photography, 5 views-frontal, 45 and 90 degrees and included blinded Investigator Global Assessment of Improvement compared to baseline; subject Self-Assessment of Improvement compared to baseline and VISIA System Photography (one site). Adverse events were evaluated as well.

Follow-ups were by a 3 day phone call and visits at 2, 4, 8 and 12 weeks. In all these groups including Control had 50%-65% of subjects showed reduction in pigment after 30 days both by independent assessment and self-assessment. The results were generally improved for Groups 3 and 4 compared to Group 2—at 30 days independent assessment found 50% of Group 2 subjects improved, and 60% and 65% of subjects in Groups 3 and 4 respectively. (Self-assessment results showed little differences all at about 60%.)

Example 6—Administration of Bicarbonate Topically Using Selected Formulations

An objective of this series of studies was to compare different transdermal compounds to determine which compound, dose, concentration combinations induce the highest urine with the lowest levels of skin irritation. Presented below are data and results from several experiments that determine and compare various formulations in terms of effectiveness for treatment and side effects, and in particular tolerance from skin irritation.

In the first study, twenty-four 6 week old female SCID mice were used in this study, divided into four groups of six mice each. The backs of mice were treated with hair removal compound before topical formulations were applied. Topical formulations were then applied to the back of each mouse from hip to shoulder three times per day at a dose of 500, totaling 150 µl for 3 consecutive days. Urine samples were collected twice daily, one in the morning and one in the afternoon and stored at 4° C. for subsequent pH determination. The transdermal formulations from Study 1 comprise formulations as follows: Group A, 15.8% sodium bicarbonate in water; Group B, 29% lysine in water; Group C, 9.3% Sodium Phosphate in water; Group D, 23.4% Tris in water (see Table 15). Pre-dosing urine pH from 15 mice was 5.97±0.06 (mean±SEM). The transdermal formulations from cohort Groups A-D are shown in Table 15.

TABLE 15

Buffer Formulations Tested

| Cohorts | Buffer formulation | Total dose/clay |
|---|---|---|
| Group A | 15.8% sodium carbonate | 150 µl |
| Group B | 29% lysine | 150 µl |
| Group C | 9.3% trisodium phosphate | 150 µl |
| Group D | 23.4% TRIS | 150 µl |

Figure 6:
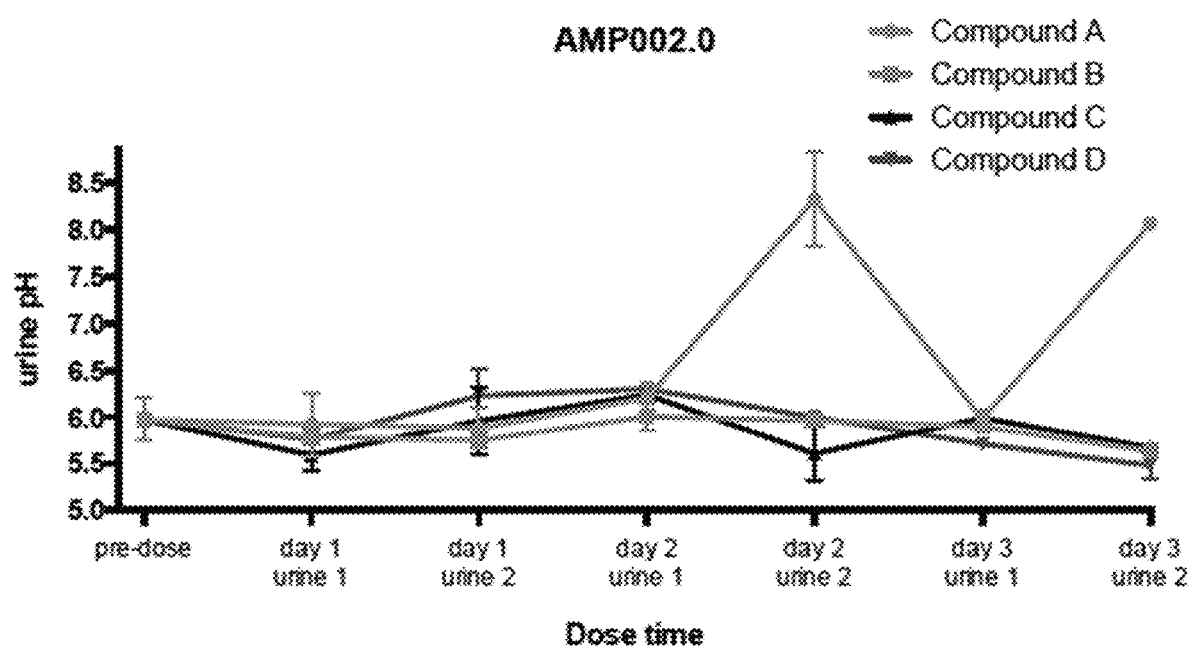
FIG. 6 shows the time course of urine pH over a 3-day period using and comparing four different topical formulations.

In all cohort groups the formulations absorbed quickly and easily. Formula A caused severe skin irritation after the first day and scabbing by the end of the third day in the Group A cohort mice (not shown). However, formulation A is the only one tested in Table 15 that significantly increased urine pH after the second day of dosing, and cyclic diurnal variation was evident by day 2 (see FIG. 6).

In a second study, a variation of the above study was performed with the exclusion of Formula A in which the mice received larger doses to test the effect of larger doses (100 µl/dose, 3 times a day). The total dose/day in these cohort mice was 300 µl/day. Formula A was excluded from further testing because, while it was effective in increasing urine pH, it caused sever skin irritation and intolerance in mice. The transdermal formulations from Study 2 included the following formulations: Group B, 29% lysine in water; Group C, 9.3% Sodium Phosphate in water; Group D, 23.4% Tris in water (see Table 16).

TABLE 16

Buffer Formulations Tested

| Cohorts | Buffer formulation | Total dose/day |
|---|---|---|
| Group B | 29% lysine | 300 µl |
| Group C | 9.3% trisodium phosphate | 300 µl |
| Group D | 23.4% TRIS | 300 µl |

Figure 7:
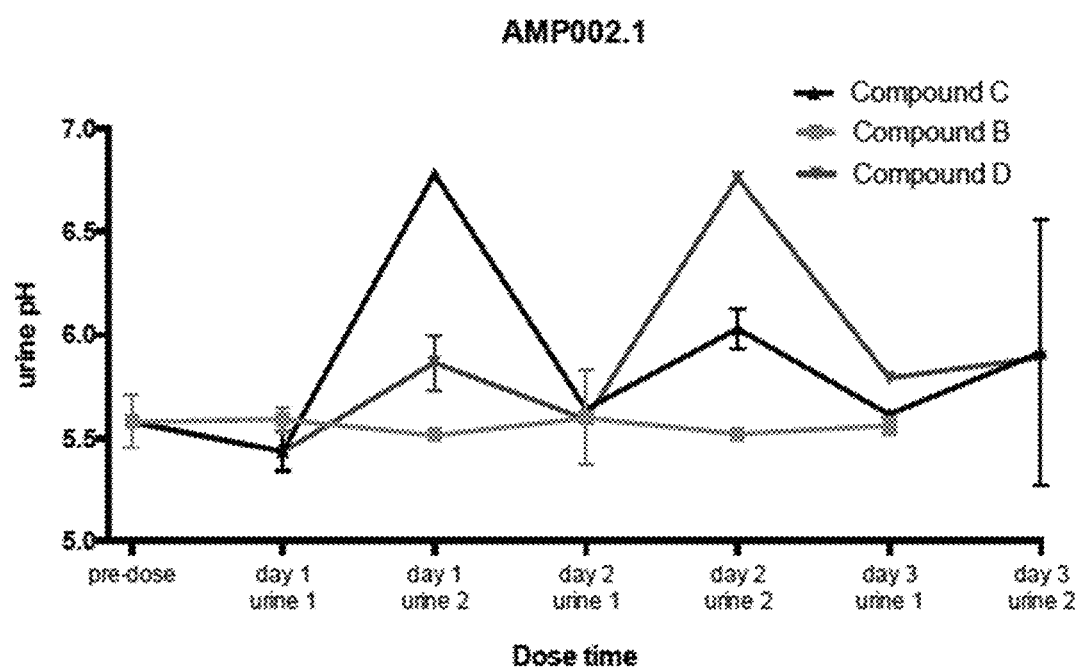
FIG. 7 shows the time course of urine pH over a 3-day period using and comparing three different topical formulations.

Pre-dosing urine pH from 10 mice was 5.58±0.04 (mean±SEM). The transdermal agent absorbed quickly and easily in all cohort groups (A-D). No skin irritation observed in any of the cohorts. As illustrated in FIG. 7, the results show that compounds C and D increased urine pH at various intervals. Urine collected for the 2nd time on day 1 was highest in pH in mice treated with compound C (FIG. 7). Urine collected for the 2nd time on day 2 was highest in pH in mice treated with compound D (FIG. 7).

In the third study, a variation of study II above was then performed with a higher total dose/day to test the effect of larger doses (100 µl/dose, 3 times a day). The total does/day in these cohort mice was 300 µl/day. Formula A was excluded from further testing because, while it was effective in increasing urine pH, it caused sever skin irritation and intolerance in mice. The transdermal formulations from Study 2 comprised formulations as follows: Group B, 29% lysine in water; Group C, 9.3% Sodium Phosphate in water; Group D, 23.4% Tris in water (see Table 16). Pre-dosing urine from 10 mice was 5.58±0.04 (mean±SEM). The transdermal agent absorbed quickly and easily in all cohort groups (B,C,D). There was no skin irritation observed in any of the cohorts. The results are shown in FIG. 7, where it can be seen that compounds C and D increased urine pH at various intervals. Urine was collected for the 2nd time on day 1 was highest in pH in mice treated with compound C (FIG. 7). Urine collected for the 2nd time on day 2 was highest in pH in mice treated with compound D (FIG. 7).

TABLE 17

Buffer Formulations Tested

| Cohorts | Buffer formulation | Total dose/day |
|---|---|---|
| Group E | 7.5% Sodium Carbonate | 300 µl |
| Group F | 7.5% Sodium Carbonate (w selected penetration enhancers) | 300 µl |
| Group G | 7.5% Sodium Carbonate, 6% Sodium Bicarbonate | 300 µl |
| Group H | 33.3% TRIS | 300 µl |

Figure 8:
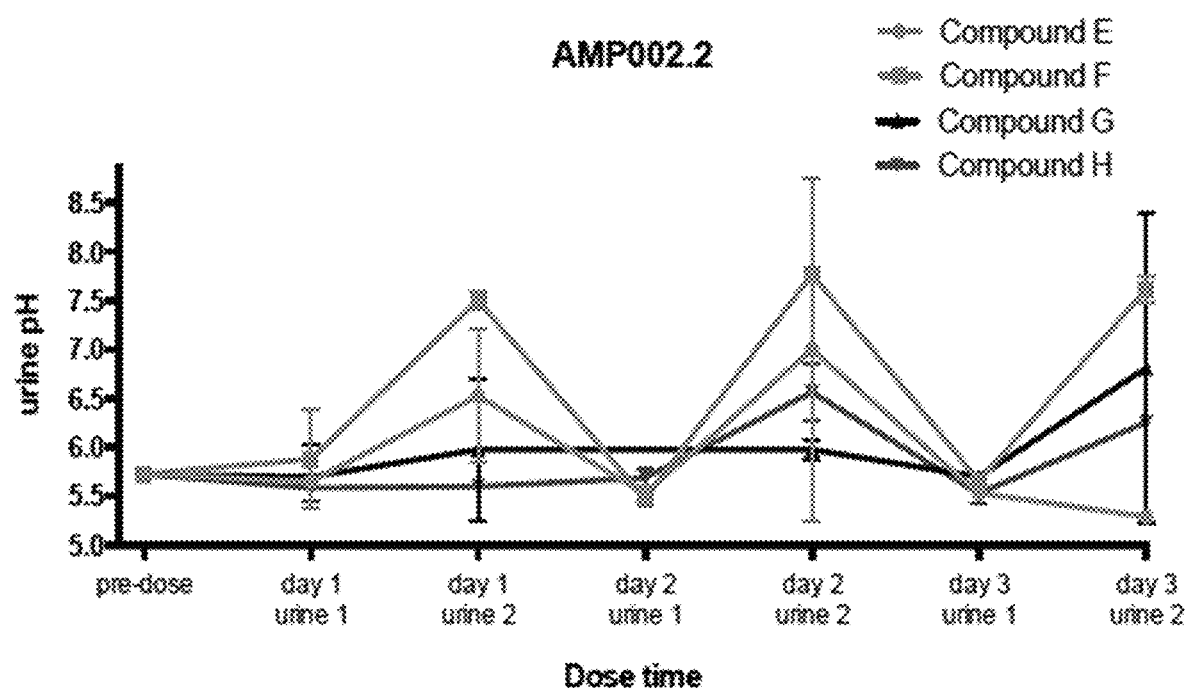
FIG. 8 shows the time course of urine pH over a 3-day period using and comparing four different topical formulations.

In a fourth study, a variation of the second study above was preformed where mice received a total dose of 300 µl/day of the formulations shown in Table 17. Pre-dosing urine levels from 4 mice was 5.73±0.02 (mean±SEM). As shown in FIG. 8, all compounds were able to increase urine pH significantly. Urine pH increases were observed after the 2nd collection of urine towards the end of the study day. Compound F (7.5% Sodium Carbonate with modified penetration enhancers) consistently induced the highest urine pH (FIG. 8).

In a fifth study, compound F (7.5% Sodium Carbonate with selected penetration enhancers) were tested in three doses of cohorts as follows: 150 µL/day, 200 µL/day, and 300 µL/day. One group was treated with 200 mM sodium bicarbonate drinking water as a positive control. The formulations used in this study are shown in Table 18.

TABLE 18

Buffer Formulations Tested

| Cohorts | Buffer formulation | Total dose/day |
|---|---|---|
| Group F | 7.5% Sodium Carbonate | 150 µl |
| Group F | 7.5% Sodium Carbonate (w selected penetration enhancers) | 200 µl |
| Group F | 7.5% Sodium Carbonate, 6% Sodium Bicarbonate | 300 µl |
| Group SB | 200 mM Sodium Bicarbonate water | ad libitum |

Pre-dosing urine from 6 mice was 5.6±0.03 (mean±SEM). The pH measurement results are presented in FIG. 8, which also shows that the response of compound F at a dose of 150 µL/day was similar to that at 300 µL/day (FIG. 8)

In another study, three doses of compound F (7.5% Sodium Carbonate with selected penetration enhancers) were test in three of the cohorts 30 µL/day, 75 µL/day, and 150 µL/day. One group was treated with 200 mM sodium bicarbonate drinking water as a positive control. The formulations tested are shown in Table 19.

TABLE 19

Buffer Formulations Tested

| Cohorts | Buffer formulation | Total dose/day |
|---|---|---|
| Group F | 7.5% Sodium Carbonate | 30 µl |
| Group F | 7.5% Sodium Carbonate (w selected penetration enhancers) | 75 µl |
| Group F | 7.5% Sodium Carbonate, 6% Sodium Bicarbonate | 150 µl |
| Group SB | 200 mM Sodium Bicarbonate water | ad libitum |

Figure 9:
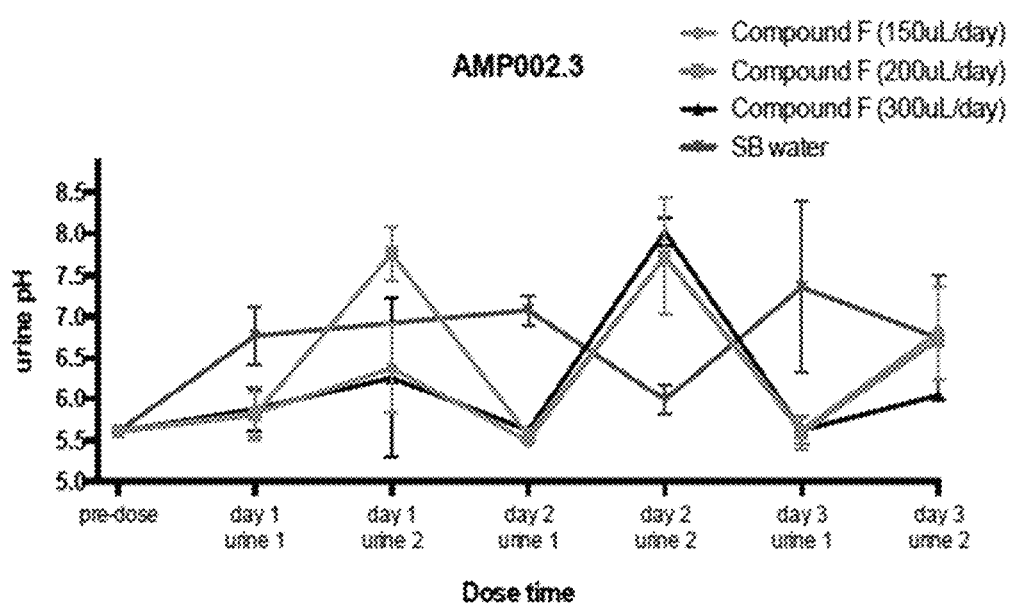
FIG. 9 shows the time course of urine pH over a 3-day period using one formulation applied topically at three doses.

The pre-dosing urine pH from 3 mice was 5.57±0.06 (mean±SEM). As shown in FIG. 9, urine pH values trended lower in all groups in this round of studies. Higher urine pH levels were observed in the 150 µL/day cohort, and was most similar to the sodium bicarbonate water positive control group (FIG. 9).

Figure 10:
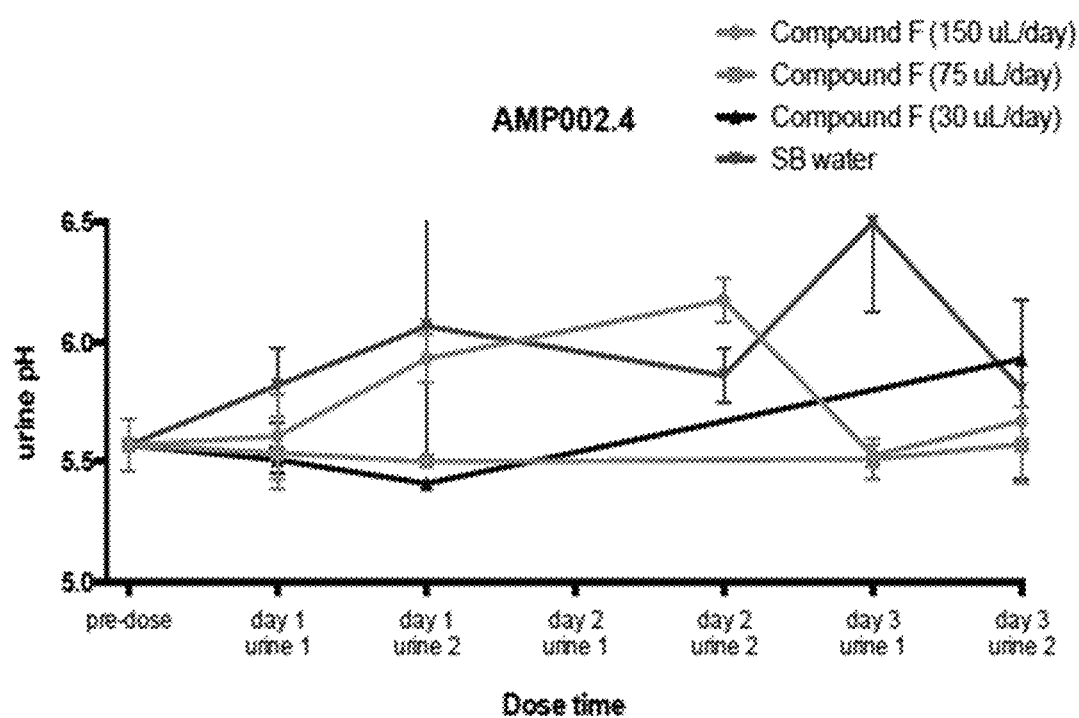
FIG. 10 shows the time course of urine pH over a 3-day period using one formulation applied topically at three doses.

In another study, three doses of compound F (7.5% Sodium Carbonate) was tested in three of the cohorts at doses of 100 µL/day, 125 µL/day, and 150 µL/day. One group was treated with 200 mM sodium bicarbonate drinking water as a positive control. The formulations tested are shown in Table 20 and results of the dose response curve are shown in FIG. 10. With reference to the selected penetration enhancers referenced in the formulations of Table 19 and 20, these were 0.11% diethanolamine, 1.94% sodium caprate, and 0.20% sodium lauryl sulfate. EDTA in an amount of 0.30% was also added to the formulations of Table 19 and 20. Other penetration enhancers as well as different amount of penetration enhancers are suitable in other embodiments.

TABLE 20

Buffer Formulations Tested

| Cohorts | Buffer formulation | Total dose/day |
|---|---|---|
| Group F | 7.5% Sodium Carbonate | 100 µl |
| Group F | 7.5% Sodium Carbonate (w selected penetration enhancers) | 125 µl |
| Group F | 7.5% Sodium Carbonate, 6% Sodium Bicarbonate | 150 µl |
| Group SB | 200 mM Sodium Bicarbonate water | ad libitum |

FIG. 10 is a dose response curve showing urine pH for 3 days, showing the 200 mM sodium bicarbonate control, 100 µl of formulation, 1250 of formulation, and 150 µl of formulation.

Figure 11:
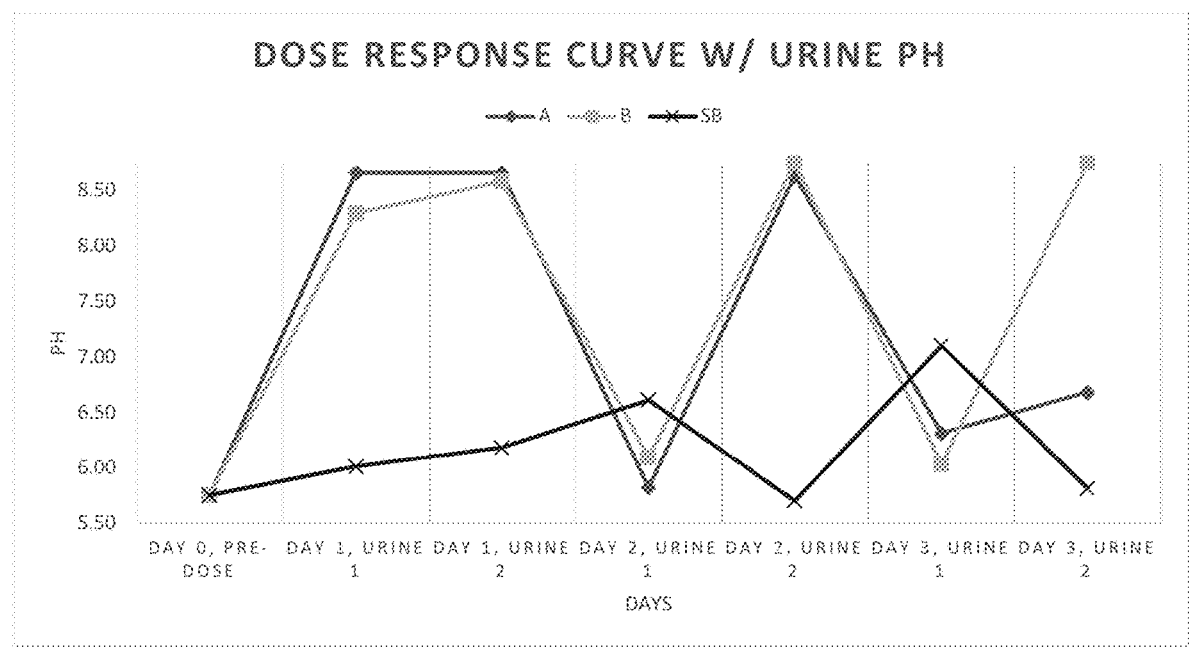
FIG. 11 is a dose response curve showing urine pH for 3 days, where the 200 mM sodium bicarbonate control is shown in yellow, the 100 µl of formulation is grey, the 125 µl of formulation is orange, and the dose amount of 150 µl of formulation is blue.

FIG. 11 shows urine pH measured over 3 days for two pH modulating buffering formulations: A, B, and 200 mM sodium bicarbonate in water administered as libitum as a control. These pH modulating buffering compounds are presented in Table 21.

TABLE 21

Formulation Compositions Study

| Ingredient | Formula A | Formula B |
|---|---|---|
| LIP | 14.00% | 15.00% |
| BA | 1.00% | 1.00% |
| Menthol | 0.25% | 0.25% |
| Durasoft | 1.50% | 1.50% |
| Pluronic Granules | 5.40% | 2.10% |
| Water | 31.60% | 29.65% |
| Sodium Carbonate | — | — |
| Sodium Bicarbonate | 32.50% | 32.50% |
| EGTA | — | — |
| sodium deconate | — | — |
| propylene glycol | 6.00% | 10.00% |
| almond oil | 4.00% | 3.00% |
| zinc oxide | 0.25% | 0.50% |
| cetyl alcohol | 2.00% | 3.00% |
| ethanol | 1.50% | 1.50% |

Figure 12:
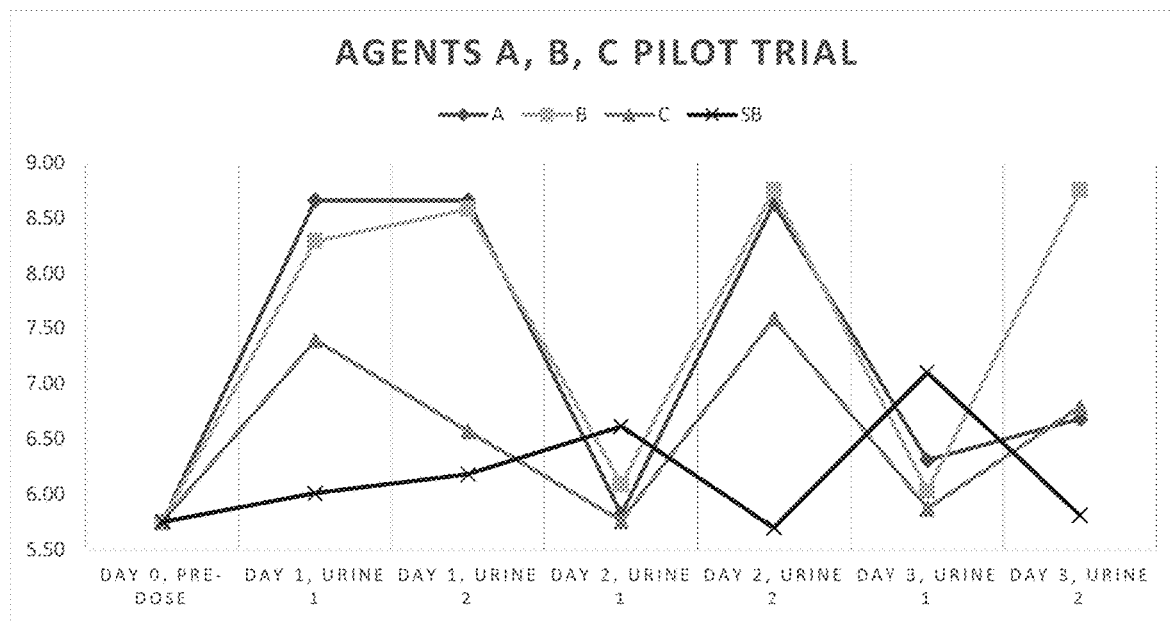
FIG. 12 shows urine pH measured over 3 days for two pH modulating buffering formulations: A, B and 200 mM sodium bicarbonate in water administered as libitum as a control.

FIG. 12 shows urine pH measured over 3 days for three pH modulating buffering formulations: A, #25, #28, #29 and 200 mM sodium bicarbonate in water administered as libitum as a control. These pH modulating buffering compounds are presented in Table 20.

TABLE 20

Formulation Compositions Study

| Ingredient | Formula 25 | Formula 28 | Formula 29 |
|---|---|---|---|
| LIP | 6.00% | 12.00% | 12.00% |
| BA | 1.00% | 1.00% | 1.00% |
| Menthol | 0.50% | 0.50% | 0.50% |
| Pluronic Granules | 4.20% | 4.20% | 4.20% |
| Water | 37.80% | 37.80% | 40.30% |
| Sodium Carbonate | 7.00% | 7.00% | 7.00% |
| Sodium Bicarbonate | 28.00% | 28.00% | 28.00% |
| EGTA | — | — | 0.50% |
| propylene glycol | 3.00% | 3.00% | — |
| almond oil | 3.00% | 3.00% | 3.00% |
| cetyl alcohol | 3.00% | 3.00% | 3.00% |
| lecithin | 3.00% | — | — |
| cetiol ultimate | 3.00% | — | — |
| ethanol | 1.50% | 1.50% | 1.50% |

Figure 13:
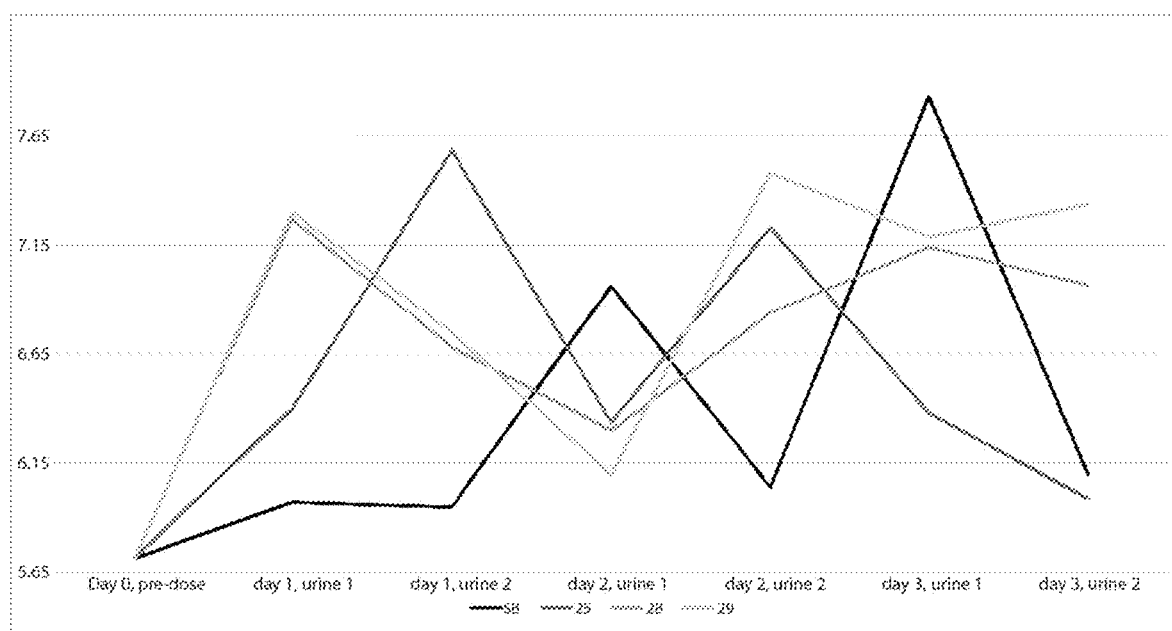
FIG. 13 shows urine pH measured over 3 days for three pH modulating buffering formulations: A, #25, #28, #29 and 200 mM sodium bicarbonate in water administered as libitum as a control.

FIG. 13 shows urine pH measured over 3 days for three pH modulating buffering formulations: #25, #28, and #29 and control (SB, 200 mM sodium bicarbonate in water).

Figure 14:
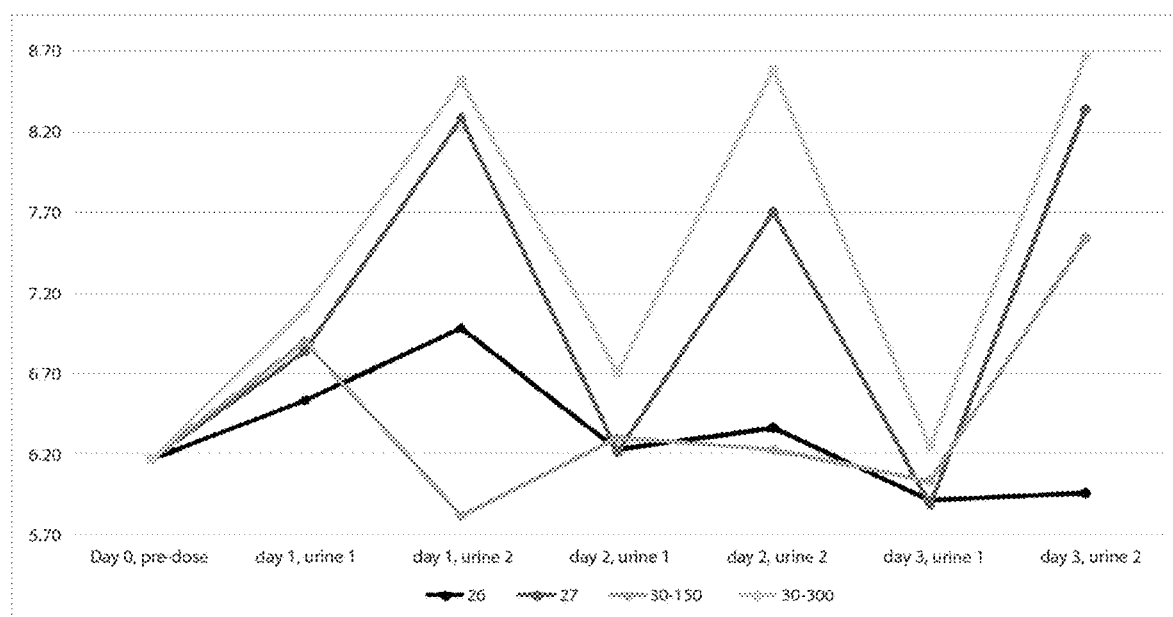
FIG. 14 shows urine pH measured over 3 days for three pH modulating buffering formulations: #26 and #27.
Figure 15:
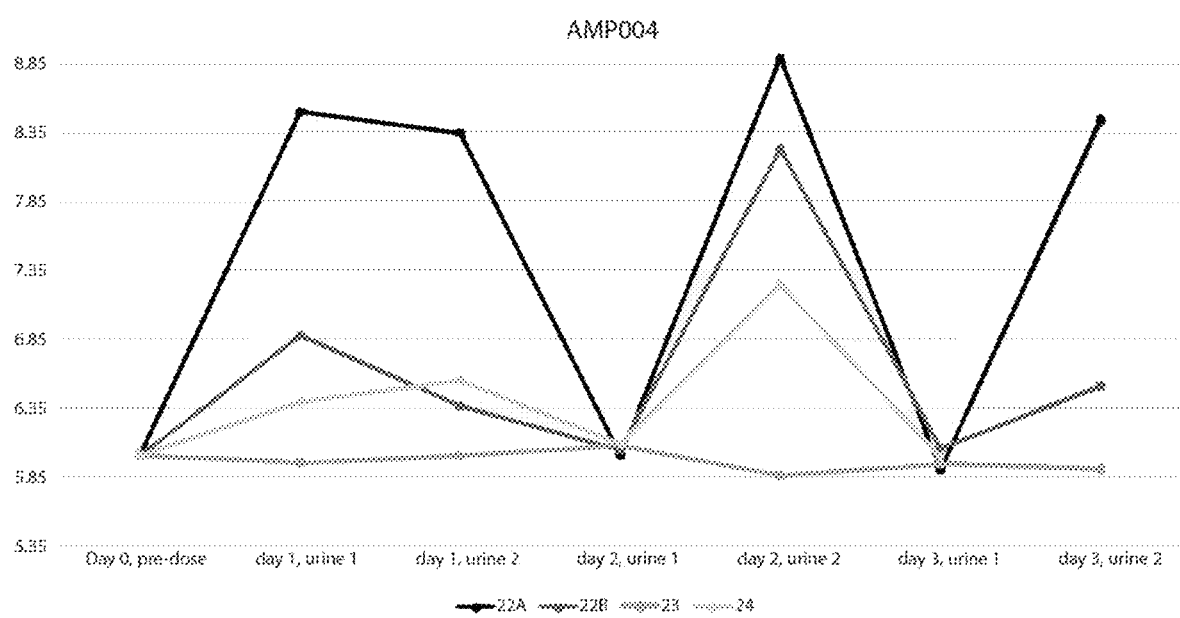
FIG. 15 shows urine pH measured over 3 days for four pH modulating buffering formulations: #22A, #22B, #23, and #24.

FIG. 14 shows urine pH measured over 3 days for four pH modulating buffering formulations: #22A, #22B, #23, and #24.

The data and results from the studies reported in Example 6 can be summarized as follows. A formulation of 150 µL/day of 29.0% Lysine HCL, 9.3% Trisodium Phosphate, and 23.4% TRIS did not significantly raise urine pH. Doubling the doses (300 µL/day) of 9.3% Trisodium Phosphate and 23.4% TRIS did not significantly raise urine pH. Doubling dose (300 µL/day) of 29.0% Lysine had no impact on urine pH. All formulations of sodium carbonate tested consistently increases urine pH. A formulation of 15.8% sodium carbonate is highly effective in raising urine pH, but caused skin irritation marked by redness and scabbing within 3 days. A formulation of 7.5% sodium carbonate (with selected penetration enhancers) achieved similar outcomes as 15.8%, but with no skin irritation. A formulation of 7.5% sodium carbonate (with modified penetration enhancers) appeared to have a greater impact on increasing urine pH than 7.5% sodium carbonate. Changes in urine pH induced by formulations comprising 7.5% sodium carbonate (with selected penetration enhancers) appears to be dose dependent. Doses of 7.5% sodium carbonate (with selected penetration enhancers) higher than 150 µL/day were not any more effective in increasing urine pH. The dose of 150 µL/day of 7.5% sodium carbonate (with selected penetration enhancers described herein) was more optimal in raising urine pH than lower doses. Urine pH increased after application during the day, then returned to baseline levels overnight.

Example 7—CPE Formulation

This is an example of an integrative cooperative CPE formulation directed to the extra-cellular matrix to which might be added selected cysteine cathepsin protease-inhibitors, with or without a suitable buffering agent to NHE1 isoform inhibitor as a synergistic composition.
1. Cetyltrimethyl ammonium bromide (from about 2.0% to about 10.0%)
2. Sodium cholate: Lecithin (96% pure): Isopropyl myristate (equi-molar 1:1:1 (from about 10% to about 40.0%)
3. Sodium citrate (titrate to transparency/incr. viscosity of #2.)
4. Benzyl alcohol (from about 2.0% to about 30.0%)
5. Cis-Palmitoleic acid (from about 20.0% to about 30% of BA)
6. Methyl pyrrolidone (0.4%)/Dodecyl pyridinium (1.1%) (from about 0.5% to about 5.0%)
7. Pluronic 127 (qs to 100%)

Example 8—Penetration Enhancing Formulation

This is an example of the formulation, which is directed to the cellular component of the SC permeability barrier to which might be added selected cysteine cathepsin protease-inhibitors, with or without a suitable buffering agent, and NHE1 isoform inhibitor as a synergistic composition.
1. ACSSSPSKHCG, [alanine-cysteine-serine-serine-serine-proline-serine-lysine-hisitidine-cysteine-glycine] identified as TD-1
2. Thioglycolic Acid (TGA) (from about 2.0% to about 7.0% concentration) [may be substituted by other reducing agents]
3. Proteinase K (from about 5 mg/mL to about 15 mg/mL)

Example 9—Use of Topical Buffering Agents to Increase Effectiveness of Weak Base Chemotherapeutics without Adverse Events In this experiment, doxorubicin in conjunction with a formulations of the invention are tested for their ability to enhance the cytotoxicity without adverse events observed with buffering therapies are administered orally.

In vitro test were first performed and demonstrated significant increases in drug uptake and cytotoxicity. Experiments were performed using MCF-7 cells grown to log phase in 96-well plates and medium was exchanged for one at either pH 6.8 or 7.4 containing 0.208 µCi per well of 14C doxorubicin. Medium pH was buffered using non-volatile buffers (10 mM MES, 20 mM HEPES and 10 mM TRICINE) in combination with bicarbonate concentrations that were adjusted to be in equilibrium with 5% ambient carbon dioxide. Twenty-four hours later, regular growth medium was replaced and cells allowed to grow a subsequent 72 h, after which time they were fixed and stained with crystal violet for determination of cell number. In-vitro, raising the pHe from 6.8 to 7.4 resulted in a 2.25-fold enhancement of cytotoxicity and a 2.56-fold increase in intracellular doxorubicin concentrations.

In vivo tests were performed and doxorubicin in conjunction with buffering formulations of the invention demonstrated a significantly lowered tumor growth rate compared to treatment with doxorubicin alone and without adverse events observed when buffering therapies were administered orally. In this experiment MCF-7 tumors were grown in the mammary fat pads of 6-week-old female SCID mice, to sizes of 50-200 mm3, and were forcibly randomized according to tumor size into six groups:
Group A and B: Control
Group C and D: 200 mM sodium bicarbonate drinking water ad libitum
Group E and F: 50 µL×3 doses approximately Q8 hours (total daily dose of 150 µL) of formulation in Table 21 below as follows:

TABLE 21

| Ingredient | Group E and F Formulation |
| --- | --- |
| LIP | 6.00% |
| BA | 1.00% |
| Menthol | 0.50% |
| Pluronic Granules | 4.20% |
| Water | Q.S. |
| Sodium Bicarbonate | 33.00% |
| Propylene glycol | 3.00% |
| almond oil | 3.00% |
| cetyl alcohol | 3.00% |
| lecithin | 3.00% |
| cetiol ultimate | 3.00% |
| ethanol | 1.50% |

The start of the bicarbonate treatment was designated as day 1. On days 3, 7 and 11, animals in groups B, D, and F were injected i.p. with 1.6 mg kg-1 doxorubicin while animals in groups A, C, and E (n=10 each) received saline injections of the same volume, as per established protocols. On day 15, animals in Groups C and D were placed back on normal drinking water and animals in Groups E and F ceased received t.i.d. topical applications.

Tumor volumes and animal weights were monitored every 2 days. Doxorubicin had a significant effect on the tumor growth rate (Groups B growth rate decreased ~30% over assessment period). This effect was greater in animals co-treated with bicarbonate whether by oral or topical administration (With both Groups D and F observing a 55% reduction in growth rate). In this embodiment, bicarbonate alone (Groups C and E) had no significant effect on the growth rate alone. Other characteristics of tumors that increase its potential for carcinogenesis other than growth rates are measured by other parameters as well, including inhibition metastasis. In the inventor's experience, different embodiments disclosed herein may have differential effects on different characteristics of tumors (e.g. growth rate, volume, metastasis, pH microenvironment, etc.).

In addition to tumor volumes, animals in group D experienced anal discharge suggesting increased GI tract cytotoxicity of doxorubicin when orally dosed. This adverse event was not noted in topically dosed animals that received doxorubicin (Group F).

Example 10—Use of Topical Buffering Agents to Increase Effectiveness of Immunotherapies in Melanoma In this experiment, we studied the effects of a formulations of the invention on the efficacy of immunotherapy for melanoma. It is understood that the highly acidic tumor microenvironment might blunt the effectiveness of anti-tumor immunity.

For three days C57BL/6 mice received 50 µL×3 doses approximately Q8 hours (total daily dose of 150 µL) of 33% sodium bicarbonate in a formulation of the invention detailed below. On day 4, the mice were subject to tumor injection and continued to receive the sodium bicarbonate topical until the end of the experiment. Control mice received a placebo topical cream as detailed in Table 22 below.

TABLE 22

| Ingredient | Control | Active |
|---|---|---|
| Ethanol | 1.50% | 1.50% |
| Benzyl Alcohol | 1.00% | 1.00% |
| Cetyl Alcohol | 2.00% | 2.00% |
| Almond Oil | 3.00% | 3.00% |
| Lecithin | 10.00% | 7.00% |
| IPP | 10.00% | 7.00% |
| Propylene Glycol | 5.00% | 5.00% |
| Poloxamer/Pluronic Powder | 9.00% | 5.40% |
| Water | Q.S. | Q.S. |
| Sodium Bicarbonate | 0.00% | 33.00% |
| Durosoft PK-SG | 1.00% | 1.00% |
|  | 100.00% | 100.00% |

A total of $1 \times 10^5$ B16 melanoma tumor cells were injected s.c. in the left flank of the C57BL/6 mice. Mice received i.p. injections of 20 mg/kg of anti-PD1 or anti-CTLA4 antibodies on day 4 and continued to receive antibodies every 3 days until the end of the experiment. Mice were humanely euthanized when tumors exceeded 1.5 cm in diameter, appeared necrotic, or interfered with locomotion. Tumors were collected and weighed.

The topical sodium bicarbonate improved CTLA4 therapy in B16 melanoma decreasing mean tumor size from ~800 mm³ in controls to ~550 mm³ in actives and decreasing tumor weight from a mean of ~775 mg in the control arm to a mean of ~400 mg in the active arm.

The topical sodium bicarbonate improved PD1 therapy in B16 melanoma decreasing mean tumor size from ~250 mm² in controls to ~150 mm² in actives and decreasing tumor weight from a mean of ~650 mg in the control arm to a mean of ~325 g in the active arm.

Example 11=Use of Topical Buffering to Increase Effectiveness of Immunotherapies in Pancreatic Tumors In this experiment, we studied the effects of formulations of the invention on the efficacy of immunotherapy for pancreatic tumors. It is understood that the highly acidic tumor microenvironment might blunt the effectiveness of anti-tumor immunity.

For three days C57BL/6 mice received 50 µL×3 doses approximately Q8 hours (total daily dose of 150 µL) of 33% sodium bicarbonate in a formulation of the invention detailed below. On day 4, the mice were subject to tumor injection and continued to receive the sodium bicarbonate topical until the end of the experiment. Control mice received a placebo topical cream as detailed in Table 23 below.

TABLE 23

| Ingredient | Control | Active |
|---|---|---|
| Ethanol | 1.50% | 1.50% |
| Benzyl Alcohol | 1.00% | 1.00% |
| Cetyl Alcohol | 2.00% | 2.00% |
| Almond Oil | 3.00% | 3.00% |
| Lecithin | 10.00% | 7.00% |
| TPP | 10.00% | 7.00% |
| Propylene Glycol | 5.00% | 5.00% |
| Poloxamer/Pluronic Powder | 9.00% | 5.40% |
| Water | Q.S. | Q.S. |
| Sodium Bicarbonate | 0.00% | 33.00% |
| Durosoft PK-SG | 1.00% | 1.00% |
|  | 100.00% | 100.00% |

A total of $1 \times 10^5$ Panc02 pancreatic tumor cells were injected s.c. in the left flank of the C57BL/6 mice. Mice received i.p. injections of 20 mg/kg of anti-PD1 antibodies on day 4 and continued to receive antibodies every 3 days until the end of the experiment. Mice were humanely euthanized when tumors exceeded 1.5 cm in diameter, appeared necrotic, or interfered with locomotion. Tumors were collected and weighed.

The topical sodium bicarbonate improved PD1 therapy in Panc02 decreasing tumor weight from a mean of ~650 mg in the control arm to a mean of ~300 g in the active arm.

Example 12—Use of Topical Buffering Agents to Decrease Primary Tumor Metastases and Increase Survival in Metastatic Breast Cancer In this experiment, topical applications of buffer with formulations of the invention were tested for their ability to buffer extracellular acidity and inhibit the spread of metastases and increase overall survival in a mouse model for metastatic breast cancer. The topical formulations of the invention were compared to a "no treatment" control as well as orally delivered buffer as a positive control.

In vivo tests were performed as follows: 72 female Ncr nude mice aged 6 weeks were injected with $5 \times 10^6$ MDA-MB-231/eGFP cells in the mammary fatpad to generate orthotopic "primary" tumors. The following day after tumor inoculation, mice were then randomized into 5 treatment groups as outlined below.

The treatment groups were:
Group A: Untreated Control
Group B: 200 mM sodium bicarbonate drinking water ad libitum
Group C: 50 μL×3 doses daily (total daily dose of 150 μL) of formulation detailed below
Group D: 50 μL×3 doses d (total daily dose of 150 μL) of formulation detailed below
Group E: 50 μL×3 doses daily (total daily dose of 150 μL) of formulation detailed below The formulations of the embodiment are shown in Table 24 were as follows:

TABLE 24

| Ingredient | % weight |
|---|---|
| Group | C |
| Menthol | 0.50% |
| Ethanol | 1.50% |
| Benzyl Alcohol | 1.00% |
| Cetyl Alcohol | 2.00% |
| Almond Oil | 3.00% |
| LIP | 14.00% |
| Propylene Glycol | 5.00% |
| 30% Pluronic Gel | 18.00% |
| DI Water | 21.00% |
| Sodium Bicarbonate | 33.00% |
| Durosoft PK-SG | 1.00% |
| Total | 100.00% |
| Group | D |
| Menthol | 0.50% |
| Benzyl Alcohol | 1.00% |
| LIP | 25.00% |
| Cetyl Alcohol | 1.50% |
| Stearic Acid | 1.50% |
| Deionized Water | 3.24% |
| Ethanol | 1.50% |
| 30% Pluronic Gel | 30.56% |
| NaOH 50% Solution | 1.00% |
| Sodium Bicarbonate | 33.20% |
| Durosoft PK-SG | 1.00% |
| Total | 100.00% |
| Group | E |
| Menthol | 0.50% |
| Benzyl Alcohol | 1.00% |
| Cetyl Alcohol | 2.00% |
| Stearic Acid | 2.00% |
| Almond Oil | 3.00% |
| LIP | 14.00% |
| Ethanol | 1.50% |
| Propylene Glycol | 5.00% |
| 30% Pluronic Gel | 18.00% |
| DI Water | 18.00% |
| 50% NaOH Solution | 1.00% |
| Sodium Bicarbonate | 33.00% |
| Durosoft PK-SG | 1.00% |
| Total | 100.00% |

Application of transdermal agent in treatment groups C, D, and E occurred 3 times/day for 120 days. Volumes of primary tumors in mammary fat pads were measured twice weekly and calculated from orthogonal measurements of external dimensions as (width)2×(length)/2. Surgical resections of primary tumors occurred tumors reached 350-500 mm3 Mice were euthanized by cervical dislocation when tumor burden became excessive (primary, intraperitoneal, or lymph node >2000 mm3) or when mouse progressed to a moribund state. Survival data were expressed as a Kaplan-Meier curve.

Upon termination of the survival experiment, tumor metastases were identified by gross necropsy. All tumor tissue was fixed in 10% neutral buffered formalin (NBF). The green fluorescent (GFP) tumors were detected using a 470 nm/40 nm excitation filter and imaged using a mounted digital camera. Whole lung images data were analyzed with Adobe Photoshop 5.0 using the "magic wand" tool to select lung area and green fluorescent tumor lesions. Pixel area of the selected images was measured using ImageJ.

The primary tumor growth rates were observed to be the same in all active Groups, Groups B, C, D, and E. This is consistent with earlier findings in orally administered buffering therapies.

There were significant differences observed in metastatic rates in all groups treated with buffer, Groups B, C, D, and E. In addition, topically applied buffer groups, Groups C, D, and E demonstrated lower metastatic rates compared to orally dosed, Group B. As follows:

In the untreated Group A, metastatic rates were as follows:
Intestinal: 36%
Mesentery: 14%
Lymph Node: 64%
Lung: 79%

In the orally treated, Group B, metastatic rates were as follows:
Group A Metastatic Rates:
Intestinal: 0%
Mesentery: 0%
Lymph Node: 27%
Lung: 8%

In the topically treated groups, Group C, D and E metastatic rates were all lower and within the following ranges:
Group A Metastatic Rates:
Intestinal: 0%
Mesentery: 0%
Lymph Node: 5-27%
Lung: 3-8%

There were significant differences observed in survival rates in all groups treated with buffer, Groups B, C, D, and E. In addition, topically applied buffer groups, Groups C, D, and E demonstrated lower metastatic rates compared to orally dosed, Group B. As follows:
% of mice surviving to 120 days:
Group A: 20%
Group B: 60%
Groups C-G: 60%-70%

Example 13—Treatment Primary Tumor Growth, pH and Spontaneous Metastases with Formulations of the Invention To investigate the effect of various formulations provided herein on primary tumor growth, Luciferase expressing prostate cancer cells, PC3M-luc, will be subcutaneously into the right flank of male SCID mice. A suitable skin portion of all animals can be removed of hair to allow directed application of a particular formulation. Four days prior to injections, half of the animals will be treated with different amounts of selected formulation.

Animals will be imaged weekly via bioluminescence. Images from representative animals will be taken as an indication of growth of the primary tumor in both cohorts of animals. A plot of bioluminescence of the primary tumor versus time can then be established.

The tumor pH will also be taken immediately prior to euthanasia (29 days after injection of the primary tumor), and the tumors are to be harvested immediately afterwards. The mean tumor pH for each animal will be averaged within each treatment group (tap versus IEPA); and the error can be calculated as the standard error between the mean tumor pH in each group.

Necrosis of the primary tumor can also be studied by H&E staining and counted by area, as outlined in Hashim et al., Clin Exp. Metastasis (2011), 28:841-849; DOI 10.1007/s10585-011-9415-7, incorporated by reference herein.

Methods

Three days prior to inoculation with tumor cells, 4-6 week old male beige SCID mice (Harlan, Madison, Wis.) are placed into experimental cohort groups. Animal weights were measured and recorded twice weekly, and the overall health of each animal was noted to ensure timely endpoints within the experiment.

Cell culture and inoculation. PC3M cells (−Luc6 clone) are available from obtained from Caliper (Hopkinton, Mass.). The cells are cultured using MEM/EBSS media, supplemented with 10% fetal bovine serum, 1% penicillin streptomycin, 1% nonessential amino acids, 1% sodium pyruvate and 1% MEM vitamins. In preparation for inoculation into mice, the cells can be trypsinized and rinsed once with sterile phosphate buffered saline (PBS) prior to resuspension at a concentration of 5×106 cells in 200 µl PBS. For primary tumor injection, animals are prepared by removing the hair from the injection site, and 200 µl containing 5×106 cells in PBS were injected subcutaneously into the right flank of each mouse. For experimental metastases, 200 µl containing 5×106 cells in PBS are then injected directly and slowly (over the course of 1 min) into the tail vein of each mouse. In both preparations, cell distributions were verified by bioluminescent imaging immediately following injection.

Bioluminescent imaging. Animals are anesthetized with isoflurane and injected intraperitoneally with 10 µl per g body weight of sterile d-luciferin substrate prepared in PBS at 15 mg/ml (resulting dose 150 µg/g body weight). After 5 min, mice are transferred to the thermo-regulated, light-tight chamber of the In Vivo Imaging System, IVIS-200 (Caliper; Hopkinton, Mass.). Photographic images are acquired first, and the bioluminescent images can be overlaid on top of these images. Bioluminescent images are acquired by measuring photons emitted from luciferase-expressing cells and transmitted through the tissue. The exposure time for the bioluminescent image acquisition typically ranges from 0.5 s (whole tumor images) up to 2 min (lung metastases) to ensure non-saturation, and differences in exposure time are corrected by expressing data as total flux in photons/sec, rather than photon counts. Images can be analyzed using the LivingImage software (Caliper; Hopkinton, Mass.)

Necrosis counting. The center section (~5 mm) of the subcutaneous tumor of each animal will be fixed in paraffin blocks prior to staining one 4 µm thick cross-sectional sample per animal with hematoxylin and eosin for histology. Histology slides can be scanned using the Aperio™ (Vista, Calif.) ScanScope XT with a 20×/0.8NA objective lens (200×) at a rate of 2 min per slide via Basler tri-linear-array. Image analysis can be performed using an Aperio Genie® v1 customized algorithm in conjunction with Positive Pixel Count v9 with the following optimized thresholds [Hue value=0.2; Hue width=0.6; color saturation threshold=0.05; IWP(High)=210; Iwp(Low)=Ip(High)=160; Ip(low)=Isp (High)=80; Isp(Low)=0]. The algorithm is applied to the entire slide's digital image to determine the percentage of necrosis by detecting the number of pixels that satisfy the color and intensity specification defined above (necrotic), divided by the number of pixels in non-necrotic tissue.

Magnetic resonance imaging and spectroscopy. MR images and spectra can be obtained on a Varian MR imaging spectrometer ASR310 (Agilent Life Sciences Technologies, Santa Clara, Calif.) with a 30 cm horizontal clear bore operating at a field strength of 7 T. For reference, a high-resolution spectrum of IEPA in D20 can be obtained on a Varian Nuclear Magnetic Resonance spectrometer with a 54 mm vertical bore opening at a field strength of 9.4 T. For in vivo spectroscopic imaging, naïve mice were allowed to drink IEPA for 3 days prior to imaging. The animals are to be sedated using isoflurane, placed in the animal cradle for insertion into the bore of the 7 T Varian MRI and maintained warm using a continuous warm air blower (Small Animal Instruments, Inc., Stonybrook, N.Y.). Temperatures can be measured using a fiber optic endorectal thermometer in conjunction with the MR compatible animal monitoring system (Model 1025, Small Animal Instruments, Inc. Stony Brook, N.Y.). SCOUT images are taken to verify location, and T2 weighted images for anatomical identification were obtained using a fast spin echo (FSEMS) pulse sequence, with FOV=40×80 (mm), 15 coronal slices, 1 mm thick, no gap, TR=2450 s, effective TE=72 ms, with fat suppression on. Spectra can be obtained using a stimulated echo (STEAM) localization sequence on a 2×2×2.5 mm3 voxel in the bladder with 256 averages (flip angle 90 deg, TE 9.44, TM 8.01, and TR 2000), for an 8.5 min acquisition. Images and spectra were processed using the Varian Vnmrj software or using MATLAB (MathWorks, Inc, Natick, Mass.).

Electrode measurement of pH. Animals can be sedated using isoflurane, and placed on a warming surface to maintain appropriate body temperature for the duration of the experiment. Both the needle microelectrode and the reference electrode can be obtained from Microelectrodes, Inc., (Bedford, N.H.). A shallow small (<5 mm) incision is typically made in an alternate (nontumor) site and the 1 mm reference electrode was placed subcutaneously therein. A needle micro electrode (OD 0.8 mm with a beveled end) is inserted up to 1.3 cm into the center of the tumor, and was held in place for up to 1 min, until pH readings stabilized. The needle is rotated once in each location, to allow the pH electrode to re-read at the same depth in order to make two independent measurements per location. The pH is typically measured at three locations, one near the center/core of the tumor, one in a mid-region of the tumor, and one at the rim of the tumor; these values are averaged to report a mean for each animal After the pH was measured in the primary tumor, the animals are euthanized (29 days after subcutaneous injection of the primary tumor cells). Before and after the pH is measured in each animal, the pH electrodes are used to measure a standard pH 7 buffer solution (Thermo Fisher Scientific, Inc., Waltham, Mass.).

Example 14—Use of Formulations of the Invention on Syngenic Melanoma Growth in CB57/BL Mice In this experiment serval formulations according to the invention are evaluated for effectiveness on tumor growth in a syngenic melanoma mouse model.

In vitro study. The murine B16F10 and the human A375 melanoma cell line is available from ATCC (Milan, Italy); the Me1501, Me30966 and WM793 human melanoma cells are also available commercially. Cells are seeded in 96 wells plates at the concentration of 5000 cells/well. The cells are maintained in RPMI culture medium with 10% of FBS at pH 7.4.

In vivo studies. Approximately 5×105 B16F10 melanoma cells are subcutaneously injected in the right flank of subject animals. Tumors are calipered twice a week and mice were weighted once a week. Mice are divided into a control group and treatment groups that receive different dosages of various formulations provided herein. Mice are checked twice a week by a veterinarian responsible for animal welfare monitoring for signs of sufferance such as weight loss, decreased water and food consumption, poor hair coat, decreased activity levels and tumor ulcerations. Endpoints were maximum tumor volume of 1200 mm3 accordingly to the guidelines for a correct laboratory practice and signs of poor quality of life.

In vivo MRI guided 31P MRS. A group of CB57/BL mice carrying syngenic melanoma tumors B16F10 implanted in the right flank are subjected to an MRI study. Upon reaching the tumor volume of 800 mm3 mice were gavaged with a single non-toxic dose of 4 or 8 g/l of formulation solubilized in 200 µl of water. Mice are subjected to MRI/MRS analyses by using a Varian Inova 200/183 MRI/MRS system for small animals operating at 4.7 T. Animals can be anesthetized with sevoflurane 2.5% in O2 1 l/min. Throughout the anesthesia procedures the ECG, PO2, and PCO2, are to be routinely monitored as per ISS guidelines and current literature. Temperature is maintained at 37±0.5° C. by a feedback controlled water circulating heating cradle. Tumor extracellular pH (pHe) value is measured from chemical shift difference between the exogenous cell impermeant 31P reporter 3-APP resonance and that of α-ATP.

The 3-APP probe (128 mg/kg) is administered i.p. immediately prior to MRI/MRS analyses. A three turn 31P surface coil specifically designed to fit superficial tumors combined with a butterfly 1H coil (RAPID Biomedical, Rimpar, Germany) for shimming and positioning of the volume of interest (VOI) can be used. T1-weighted gradient-echo multislice contiguous images (TR/TE=400/3.5 msec, a α 70°, thickness=1 mm, 8 averages, 19 slices, matrix 128×128, FOV=3×3 cm2 which correspond to in plane resolution of 0.2×0.2 mm2) are acquired to localize the tumor. 1H localized spectra is used to optimize magnetic field homogeneity in order to increase the signal resolution within the tumor (1H PRESS, TR/TE=2,000/23 msec). 31P localized spectra are acquired from the tumor with a pulse-acquire sequence (TR=3,000 ms, α=25°, 256 averages) before and up to 1.5 h after formulation administration.

Statistical analysis. Differences between treatment groups, both in vitro and in vivo, can be analyzed by one-way ANOVA and Bonferroni t-test. Data can be expressed as mean±SD and SE for in vivo experiments, and p values reported are two-sided. P values<0.05 are generally considered as statistically significant. Statistical analysis can be performed with Sigmastat 2006 software.

Example 15—Coadministration Treatments and Combinational Therapies

In this experiment, a more exhaustive study of several different chemotherapeutic agents, immunotherapeutic agents, and biological agents will be performed. Various biological, chemotherapeutic, and immunotherapeutic agents are tested in conjunction with formulations of the invention for their ability to treat cancer, reduce metastasis, reduce carcinogenesis, maintain remission, and the other methods relating to cancer and tumors described herein. Methods are performed in accordance with Examples 9-11 above, with particular biologic, chemotherapeutic and immunotherapeutic agents additionally added to test their effect on primary tumor growth.

Biological agents that are cytokines such as interferons and interleukins will be tested.

Also tested will be chemotherapeutic agents such as alkylating agents, anthracyclines, antimetabolites, antitumor antibiotics, aromatase inhibitors, taxanes and related compounds, cytoskeletal disruptors, epothilones, histone deacetylace inhibitors, kinase inhibitors, nucleoside analogues, topoisomerase inhibitors, retinoids, and vinca alkaloids and derivatives thereof. Chemotherapeutic agents to be tested include anthracyclines, antimetabolites, antitumor antibiotics, aromatase inhibitors, taxanes, and others described herein.

Immunotherapeutic agents include antibodies and cell based approaches will be tested. Those tested will include alemtuzumab, atezolizumab, avelumab, ipilimumab, durvalumab, nivolumab, ofatumumab, rituximab, and others described herein.

In related experiments, in vivo approaches to modifying gene expression are tested in conjunction with formulations of the invention for their ability to reduce cancer, metastasis, inhibit or prevent carcinogenesis, enhance immune response, etc. One approach tested will utilize the CRISPR to modify genes and gene expression of selected target genes described herein and to use this therapy in conjunction with certain topical formulations of the invention for various aspects of treating cancer described herein such as treating or preventing cancer, preventing carcinogenesis, maintaining remission, and the like. Suitable methods for screening targets and performing CRISP are described in U.S. Ser. No. 15/575,325 entitled 'Screening Methods for Cancer Therapy', filed Nov. 17, 2017, incorporated by reference herein.

Aspects of the present specification may also be described as follows:

1. A method of treating a proliferative disorder associated with cancer in a patient, the method comprising administering an effective amount of a formulation for transdermal delivery through the skin of a subject comprising one or more buffering agent to a patient in need thereof, wherein said administration is effective to i) inhibit or prevent the growth of a tumor or tumor cells, ii) inhibit or prevent the metastasis of tumors or cancer cells, iii) inhibit or prevent carcinogenesis, iv) inhibit or prevent the intravasation of tumor cells, or v) improve or extend the duration of remission, or maintain remission of a cancer or tumor.

2. A method according to claim 1, wherein said treating a proliferative disorder inhibits or prevents the growth of a tumor or tumor cells.

3. A method according to claim 1, wherein said treating a proliferative disorder inhibits or prevents the metastasis of tumors or cancer cells.

4. A method according to claim 1, wherein said treating a proliferative disorder inhibits or prevents carcinogenesis.

5. A method according to claim 1, wherein said treating a proliferative disorder inhibits or prevents the intravasation of tumor cells.

6. A method according to claim 1, wherein said treating a proliferative improves or extends the duration of remission or maintains remission of a cancer or tumor.

7. A method of treating cancer in a patient, the method comprising administering an effective amount of a formulation for transdermal delivery through the skin of a subject comprising one or more buffering agent to a patient in need thereof, wherein said administration is effective to inhibit or prevent the growth of a tumor or tumor cells.

8. A method of preventing metastasis of tumors, the method comprising administering an effective amount of a formulation for transdermal delivery through the skin of a subject comprising one or more buffering agent to a patient in need thereof, wherein said administration is effective to inhibit or prevent the metastasis of tumors or cancer cells.

9. A method according to claim 1, wherein said formulation for transdermal delivery through the skin of a subject comprises a buffering agent comprising a carbonate salt in an amount between about 10-56% w/w; a penetrant portion in an amount between about 5 to 55% w/w; a detergent portion in an amount of at least 1% w/w; and wherein the formulation comprises water in an amount from 0% w/w up to 70% w/w, and wherein the formulation optionally comprises lecithin in an amount less than about 12% w/w.

10. A method according to claim 1, wherein said formulation for transdermal delivery through the skin of a subject comprises a buffering agent comprising at least one carbonate salt, lysine, tris, a phosphate buffer and/or 2-imidazole-1-yl-3-ethoxycarbonylpropionic acid (IEPA), or a combination thereof in an amount between about 10-56% w/w; and a penetrant portion in an amount between about 44 to 90% w/w, wherein the penetrant portion comprises water in an amount less than about 85% w/w, and wherein the formulation comprises less than about 12% w/w lecithin.

11. A method according to claim 10, wherein a chemotherapeutic or immunotherapeutic agent is co-administered with said formulation comprising one or more buffering agent.

12. A method according to claim 10, wherein said administration is effective to alter the pH of a tissue or microenvironment proximal to a solid tumor or cancer cells in the patient.

13. A method according to claim 11, wherein the chemotherapeutic or immunotherapeutic agent is selected from alkylating agents, antibodies and related binding proteins, anthracyclines, antimetabolites, antitumor antibiotics, aromatase inhibitors, taxanes and related compounds, cytoskeletal disruptors, epothilones, histone deacetylace inhibitors, kinase inhibitors, nucleoside analogues, topoisomerase inhibitors, retinoids, and vinca alkaloids and derivatives thereof.

14. A method according to claim 13, wherein the chemotherapeutic or immunotherapeutic agent is an immunotherapeutic agent selected from alemtuzumab, atezolizumab, avelumab, ipilimumab, durvalumab, nivolumab, ofatumumab, rituximab and trastuzumab.

15. A method according to claim 10, comprising a carbonate salt in an amount between about 7-56% w/w of the formulation.

16. A method according to claim 9 or 15, wherein the carbonate salt in said formulation is in an amount between about 15-32% w/w of the formulation.

17. A method according to claim 9 or 15, wherein the carbonate salt in said formulation is sodium carbonate and/or sodium bicarbonate milled to a particle size is less than 200 μm.

18. A method according to claim 9 or 15, wherein the penetrant component in said formulation is in an amount between about 18-42% w/w of the formulation.

19. A method according to claim 9 or 15, wherein the water in said formulation is in an amount between about 15-42% w/w of the formulation.

20. A method according to claim 9 or 15, wherein the penetrant portion in said formulation comprises an alcohol in an amount less than 5% w/w of the formulation.

21. A method according to claim 9 or 15, wherein the penetrant portion in said formulation comprises lecithin organogel, an alcohol, a surfactant, and a polar solvent.

22. A method according to claim 9 or 15, wherein the penetrant portion in said formulation comprises lecithin organogel in an amount less than 5% w/w of the formulation.

23. A method according to claim 22, wherein the lecithin organogel in said formulation is a combination of soy lecithin and isopropyl palmitate.

24. A method according to claim 9 or 15, wherein the penetrant portion in said formulation comprises lecithin and isopropyl palmitate, undecane, isododecane, isopropyl stearate, or a combination thereof.

25. A method according to claim 9 or 15, wherein the penetrant portion in said formulation comprises a mixture of xanthan gum, lecithin, sclerotium gum, pullulan, or a combination thereof in an amount less than 5% w/w of the formulation.

26. A method according to claim 9 or 15, wherein the penetrant portion in said formulation comprises a mixture of caprylic triglycerides and capric triglycerides in amount less than 8% w/w of the formulation.

27. A method according to claim 9 or 15, wherein the penetrant portion in said formulation comprises phosphatidyl choline in amount less than 12% w/w of the formulation.

28. A method according to claim 9 or 15, wherein the penetrant portion in said formulation comprises a phospholipid in amount less than 12% w/w of the formulation.

29. A method according to claim 9 or 15, wherein the penetrant portion in said formulation comprises a mixture of tridecane and undecane in amount less than 5% w/w of the formulation.

30. A method according to claim 9 or 15, wherein the penetrant portion in said formulation comprises cetyl alcohol in amount less than 5% w/w of the formulation.

31. A method according to claim 9 or 15, wherein the penetrant portion in said formulation comprises benzyl alcohol in an amount less than about 5 w/w.

32. A method according to claim 9 or 15 wherein the penetrant portion in said formulation comprises stearic acid in an amount less than 5% w/w of the formulation.

33. A method according to claim 9 or 15, wherein said formulation comprises a gelling agent in an amount less than 5% w/w of the formulation.

34. A method according to claim 9 or 15 wherein the detergent portion in said formulation comprises a nonionic surfactant in an amount between about 2-25% w/w of the formulation; and a polar solvent in an amount less than 5% w/w of the formulation.

35. A method according to claim 34, wherein the nonionic surfactant in said formulation is a poloxamer and the polar solvent is water, an alcohol, or a combination thereof.

36. A method according to claim 34, wherein the detergent portion in said formulation comprises poloxamer, propylene glycol, glycerin, ethanol, 50% w/v sodium hydroxide solution, or a combination thereof.

37. A method according to claim 9 or 15, wherein the detergent portion in said formulation comprises glycerin in an amount less than 3% w/w of the formulation.

38. A method according to claim 9 or 15, wherein the carbonate salt is sodium carbonate and/or sodium bicarbonate in said formulation is milled to a particle size is less than 70 μm.

39. A method according to claim 9 or 15, wherein the carbonate salt in said formulation is sodium carbonate and/or sodium bicarbonate milled to a particle size is less than 70 µm, wherein the sodium bicarbonate is solubilized in the formulation in an amount less than 20% w/w of the formulation.

40. A method according to claim 9 or 15, wherein the carbonate salt in said formulation is sodium carbonate and/or sodium bicarbonate milled to a particle size is less than 70 µm, wherein particle sizes less than about 10 µm have an enhanced penetration thru the skin of a subject.

41. A method according to claim 9 or 15, wherein said formulation further comprises tranexamic acid in an amount less than 5 w/w of the formulation.

42. A method according to claim 9 or 15, wherein said formulation further comprises a polar solvent in an amount less than 5 w/w of the formulation.

43. A method according to claim 9 or 15, wherein said formulation further comprises a humectant, an emulsifier, an emollient, or a combination thereof.

44. A method according to claim 9 or 15, wherein said formulation further comprises ethylene glycol tetraacetic acid in an amount less than about 5 w/w.

45. A method according to claim 9 or 15, wherein said formulation further comprises almond oil in an amount less than about 5% w/w.

46. A method according to claim 9 or 15, wherein said formulation further comprises a mixture of thermoplastic polyurethane and polycarbonate in an amount less than about 5 w/w.

47. A method according to claim 9 or 15, wherein said formulation further comprises phosphatidylethanolamine in an amount less than about 5% w/w.

48. A method according to claim 9 or 15, wherein said formulation further comprises an inositol phosphatide in an amount less than about 5 w/w.

49. A method of preventing the intravasation of tumor cells, the method comprising administering topically and/or transdermally an effective amount of a formulation for transdermal delivery comprising one or more buffering agent to a patient in need thereof, wherein said administration is effective to inhibit or prevent the intravasation of tumor cells.

50. A method of improving, extending the duration of remission, or maintaining remission of a cancer or tumor, the method comprising administering topically and/or transdermally an effective amount of a formulation for transdermal delivery comprising one or more buffering agent to a patient in need thereof, wherein said administration is effective to improve or extend the duration of remission or maintain remission of a cancer or tumor.

51. A method of treatment of cancer comprising i) selecting a therapeutic agent comprising. a chemotherapeutic or an immunotherapeutic agent, ii) formulating the therapeutic agent in a suitable formulation, iii) administering the formulation comprising the therapeutic agent, and iv) before, during or after step iii), administering a formulation for transdermal delivery comprising one or more buffering agent topically and/or transdermally in an amount effective to inhibit or prevent the growth of a tumor or tumor cells.

52. A method of altering the pH of a tissue or microenvironment proximal to a solid tumor or cancer cells in a patient, the method comprising administering topically and/or transdermally an effective amount of a formulation for transdermal delivery comprising one or more buffering agent to a patient in need thereof, wherein said administration is effective to alter the pH of a tissue or microenvironment proximal to a solid tumor or cancer cells in the patient.

53. A method of treating a disease or disorder associated with abnormal levels of uric acid in a patient, the method comprising administering topically and/or transdermally an effective amount of a pharmaceutical formulation comprising one or more buffering agent to a patient having abnormal levels of uric acid and in need thereof, wherein said administration is effective to treat or reduce the symptoms of abnormal levels of uric acid in said patient.

54. A method according to claim 53, wherein the disease or disorder includes one of more of the following: gout, recurrent gout attack, prevention of gout, gouty arthritis, hyperuricaemia, gout-related cardiovascular disorders, Lesch-Nyhan syndrome, Kelley-Seegmiller syndrome, kidney disease, kidney stones, kidney failure, joint inflammation, inflammatory joint disease, arthritis, osteoarthritis, rheumatoid arthritis and psoriatic arthritis, urolithiasis, plumbism, hyperparathyroidism, psoriasis or sarcoidosis.

55. A method according to claim 54, wherein the disease or disorder is gout or the prevention of gout.

56. A method according to claim 54, wherein the disease or disorder comprises urolithiasis, kidney stones, or bladder stones.

57. A method according to claim 56, wherein the subject is an animal that is treated for urinary or renal stones.

58. A method of treating a urinary stone in a patient, the method comprising administering topically and/or transdermally an effective amount of a pharmaceutical formulation comprising one or more buffering agent to a patient in need thereof, wherein said administration is effective to ameliorate, treat or reduce the symptoms, size, or severity of the urinary stone.

59. A method according to the claim 58, wherein the patient is an animal

60. A method according to the claim 59, wherein the animal is cat or dog.

61. A method according to the claim 58, wherein the urinary stone is a bladder or kidney stone.

62. A method of treating a skin disorder in a subject, the method comprising administering topically and/or transdermally an effective amount of a formulation comprising one or more buffering agent to a patient having a skin disorder and in need thereof, wherein said administration is effective to treat or reduce the skin disorder symptoms in said patient.

63. A method according to the claim 62, wherein the skin disorder is melasma and said administration is effective to treat or reduce the melasma symptoms in said patient.

64. A method according to the claim 63, wherein the skin disorder is premature aging and the method prevents or inhibits collagen acylation in the skin of said patient.

65. A method of treating melasma comprising administering one or more buffering agent with a sun protecting lotion or cream.

66. A method according to any one of the preceding claims wherein said formulation for transdermal delivery comprises a buffering agent comprising a carbonate salt in an amount between about 10-45% w/w; a penetrant portion in an amount between about 5 to 55% w/w; a detergent portion in an amount between about 1 to 15% w/w; and wherein the formulation comprises water in an amount between about 15 to 65% w/w, and wherein the formulation comprises less than about 12% w/w lecithin.

67. A method according to claim 65, wherein the administering is performed topically by directly contacting the skin of said subject with the formulation provided to said subject.

68. A method according to claim 66, wherein prior to application of the formulation skin of said patient is pretreated by abrasion, tape-stripping, microderm-abrasion, or microneedling.

69. A medical formulation kit, the kit comprising a lotion for administering topically and/or transdermally a formulation comprising a buffering agent and administration directions that includes instructions for amounts and use for a medical professional.

70. A method according to claim 58, wherein the carbonate salt in said formulation is in an amount between about 7-32% w/w of the formulation.

71. A method according to claim 65, wherein the carbonate salt in said formulation is in an amount between about 15-32% w/w of the formulation.

72. A method according to claim 65, wherein the penetrant component in said formulation is in an amount between about 18-42% w/w of the formulation.

73. A method according to claim 65, wherein the water in said formulation is in an amount between about 15-42% w/w of the formulation.

74. A method according to claim 65, wherein the penetrant portion in said formulation comprises an alcohol in an amount less than 5% w/w of the formulation.

75. A method according to claim 65, wherein the penetrant portion in said formulation comprises lecithin organogel, an alcohol, a surfactant, and a polar solvent.

76. A method according to claim 65, wherein the penetrant portion in said formulation comprises lecithin organogel in an amount less than 5% w/w of the formulation.

77. A method according to claim 18, wherein the lecithin organogel in said formulation is a combination of soy lecithin and isopropyl palmitate.

78. A method according to claim 65, wherein the penetrant portion in said formulation comprises lecithin and isopropyl palmitate, undecane, isododecane, isopropyl stearate, or a combination thereof.

79. A method according to claim 65, wherein the penetrant portion in said formulation comprises a mixture of xanthan gum, lecithin, sclerotium gum, pullulan, or a combination thereof in an amount less than 5% w/w of the formulation.

80. A method according to claim 65, wherein the penetrant portion in said formulation comprises a mixture of caprylic triglycerides and capric triglycerides in amount less than 8% w/w of the formulation.

81. A method according to claim 65, wherein the penetrant portion in said formulation comprises phosphatidyl choline in amount less than 12% w/w of the formulation.

82. A method according to claim 65, wherein the penetrant portion in said formulation comprises a phospholipid in amount less than 12% w/w of the formulation.

83. A method according to claim 65, wherein the penetrant portion in said formulation comprises a mixture of tridecane and undecane in amount less than 5% w/w of the formulation.

84. A method according to claim 65, wherein the penetrant portion in said formulation comprises cetyl alcohol in amount less than 5% w/w of the formulation.

85. A method according to claim 65, wherein the penetrant portion in said formulation comprises benzyl alcohol in an amount less than about 5 w/w.

86. A method according to claim 65 wherein the penetrant portion in said formulation comprises stearic acid in an amount less than 5% w/w of the formulation.

87. A method according to claim 65, wherein said formulation comprises a gelling agent in an amount less than 5% w/w of the formulation.

88. A method according to claim 65 wherein the detergent portion in said formulation comprises a nonionic surfactant in an amount between about 2-25% w/w of the formulation; and a polar solvent in an amount less than 5% w/w of the formulation.

89. A method according to claim 81, wherein the nonionic surfactant in said formulation is a poloxamer and the polar solvent is water, an alcohol, or a combination thereof.

90. A method according to claim 81, wherein the detergent portion in said formulation comprises poloxamer, propylene glycol, glycerin, ethanol, 50% w/v sodium hydroxide solution, or a combination thereof.

91. A method according to claim 65, wherein the detergent portion in said formulation comprises glycerin in an amount less than 3% w/w of the formulation.

92. A method according to claim 65, wherein the carbonate salt in said formulation is sodium carbonate and/or sodium bicarbonate milled to a particle size is less than 200 µm.

93. A method according to claim 65, wherein the carbonate salt is sodium carbonate and/or sodium bicarbonate in said formulation is milled to a particle size is less than 70 µm.

94. A method according to claim 65, wherein the carbonate salt in said formulation is sodium carbonate and/or sodium bicarbonate milled to a particle size is less than 70 µm, wherein the sodium bicarbonate is solubilized in the formulation in an amount less than 20% w/w of the formulation.

95. A method according to claim 65, wherein the carbonate salt in said formulation is sodium carbonate and/or sodium bicarbonate milled to a particle size is less than 70 µm, wherein particle sizes less than about 10 µm have an enhanced penetration thru the skin of a subject.

96. A method according to claim 65, wherein said formulation further comprises tranexamic acid in an amount less than 5% w/w of the formulation.

97. A method according to claim 65, wherein said formulation further comprises a polar solvent in an amount less than 5 w/w of the formulation.

98. A method according to claim 65, wherein said formulation further comprises a humectant, an emulsifier, an emollient, or a combination thereof 99. A method according to claim 65, wherein said formulation further comprises ethylene glycol tetraacetic acid in an amount less than about 5 w/w.

100. A method according to claim 65, wherein said formulation further comprises almond oil in an amount less than about 5 w/w.

101. A method according to claim 65, wherein said formulation further comprises a mixture of thermoplastic polyurethane and polycarbonate in an amount less than about 5 w/w.

102. A method according to claim 65, wherein said formulation further comprises phosphatidylethanolamine in an amount less than about 5% w/w.

103. A method according to claim 65, wherein said formulation further comprises an inositol phosphatide in an amount less than about 5 w/w.

104. A method of evaluating a formulation for the treatment for cancer or a proliferative disorder related to cancer, the method comprising administering a formulation for transdermal delivery through the skin of a subject comprising one or more buffering agent, wherein said administration is evaluated for effectiveness to i) inhibit or prevent the metastasis of tumors or cancer cells, ii) inhibit or prevent the growth of a tumor or tumor cells, iii) inhibit or prevent carcinogenesis, iv) inhibit or prevent the intravasation of tumor cells, or v) improve or extend the duration of remission, or maintain remission of a cancer or tumor.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for treating rheumatoid arthritis or reducing a symptom of rheumatoid arthritis, the method comprising steps of:
   (1) identifying a subject having rheumatoid arthritis or having a symptom thereof; and
   (2) topically administering to the identified subject a transdermal formulation,
   wherein the transdermal formulation comprises a penetrant or a penetration enhancer and an amount of one or more buffering agents that is effective in treating rheumatoid arthritis or reducing a symptom thereof, and
   wherein the one or more buffering agents are selected from sodium bicarbonate, sodium carbonate, a carbonate salt, a bicarbonate salt, a phosphate buffer, TRIS, and lysine
   wherein the amount of the one or more buffering agents that is effective in treating rheumatoid arthritis or reducing a symptom thereof is from about 10% to about 56% w/w relative to the formulation.

2. The method of claim 1, wherein the transdermal formulation comprises two or more buffering agents.

3. The method of claim 2, wherein the transdermal formulation comprises three or more buffering agents.

4. The method of claim 2, wherein, when present, the sodium bicarbonate is at a concentration from about 1% to about 35% w/w of the transdermal formulation, the sodium carbonate is at a concentration from about 1% to about 32% w/w of the transdermal formulation, the carbonate salt is at a concentration of about 10% to about 45% w/w of the transdermal formulation, the bicarbonate salt is at a concentration of about 7% to about 32% w/w of the transdermal formulation, the TRIS is at a concentration of about 6% to about 34% w/w of the transdermal formulation, the lysine is at a concentration of about 29% w/w of the transdermal formulation, and/or the phosphate buffer is at a concentration of about 6% to about 34% w/w of the transdermal formulation, and wherein the amount of the two or more buffering agents that is effective in treating rheumatoid arthritis or reducing a symptom thereof is from about 10% to about 56% w/w relative to the formulation.

5. The method of claim 3, wherein, when present, the sodium bicarbonate is at a concentration from about 1% to about 35% w/w of the transdermal formulation, the sodium carbonate is at a concentration from about 1% to about 32% w/w of the transdermal formulation, the carbonate salt is at a concentration of about 10% to about 45% w/w of the transdermal formulation, the bicarbonate salt is at a concentration of about 7% to about 32% w/w of the transdermal formulation, the TRIS is at a concentration of about 6% to about 34% w/w of the transdermal formulation, the lysine is at a concentration of about 29% w/w of the transdermal formulation, and/or the phosphate buffer is at a concentration of about 6% to about 34% w/w of the transdermal formulation, and wherein the amount of the three or more buffering agents that is effective in treating rheumatoid arthritis or reducing a symptom thereof is from about 10% to about 56% w/w relative to the formulation.

6. The method of claim 1, wherein, when present, the sodium bicarbonate is at a concentration from about 1% to about 35% w/w of the transdermal formulation, the sodium carbonate is at a concentration from about 1% to about 32% w/w of the transdermal formulation, the carbonate salt is at a concentration of about 10% to about 45% w/w of the transdermal formulation, the bicarbonate salt is at a concentration of about 7% to about 32% w/w of the transdermal formulation, the TRIS is at a concentration of about 6% to about 34% w/w of the transdermal formulation, the lysine is at a concentration of about 29% w/w of the transdermal formulation, and/or the phosphate buffer is at a concentration of about 6% to about 34% w/w of the transdermal formulation, and wherein the amount of the one or more buffering agents that is effective in treating rheumatoid arthritis or reducing a symptom thereof is from about 10% to about 56% w/w relative to the formulation.

7. The method of claim 1, wherein when the one or more buffering agents comprises sodium bicarbonate, sodium carbonate, a carbonate salt, and/or a bicarbonate salt, the one or more buffering agents is present in an amount from about 10% to about 45% w/w relative to the formulation.

8. The method of claim 7, wherein the one or more buffering agents present in an amount from about 10% to about 35% w/w relative to the formulation.

9. The method of claim 1, wherein the transdermal formulation is formulated as a cream, lotion, or ointment.

10. The method of claim 1, wherein the formulation further comprises menthol.

11. The method of claim 10, wherein the menthol is at a concentration from about 0.1% to about 5% w/w of the transdermal formulation.

12. The method of claim 11, wherein the menthol is at a concentration of about 0.5% w/w of the transdermal formulation.

13. The method of claim 1, wherein the method further comprises administering another therapeutic agent selected from an analgesic, an anti-inflammatory, a corticosteroid, a nonsteroidal anti-inflammatory drug (NSAID), or a disease modifying anti-rheumatic agent (DMAR agent), or a combination thereof and, wherein the DMAR agent is one or more of azathioprine, cyclosporin, gold, hydroxychloroquine, methotrexate, penicallamine, and sulphasalazine.

14. The method of claim 1, wherein the penetrant or a penetration enhancer comprising one or more of benzyl alcohol, cetyl alcohol, isododecane, isopropyl palmitate (IPP), isopropyl stearate, menthol, phosphatidyl choline, undecane, and lecithin, wherein the lecithin is selected from an egg lecithin, a soy lecithin, and a synthetic lecithin.

15. The method of claim 1, wherein the transdermal formulation further comprises a source of fatty acids comprising one or more of an alkanoic acid, caprid acid, diacid, ethyloctadecanoic acid, hexanoic acid, lactic acid, lauric acid, a lecithin, linoelaidic acid, linoleic acid, linolenic acid, neodecanoic acid, oleic acid, palmitic acid, pelargonic acid, propionic acid, stearic acid, and vaccenic acid, wherein the lecithin is selected from an egg lecithin, a soy lecithin, and a synthetic lecithin.

16. The method of claim 1, wherein the transdermal formulation further comprises a source of fatty acids, and a polar solvent, and one or more of a humectant, an emulsifier, a surfactant, and an emollient; and wherein the formulation is formulated as a cream, lotion, or ointment.

17. The method of claim 16, wherein the emulsifier comprises one or more of cetyl alcohol, polyglyceryl-4 Laurate (Durosoft®), and a phosphatidylcholine (Phospholipon® 90G).

18. The method of claim 16, wherein the humectant comprises propylene glycol.

19. The method of claim 16, wherein the surfactant comprises one or more of a polyoxyethylated castor oil derivative, nonoxynol, octoxynol, phenylsulfonate, a poloxamer (e.g., a Pluronic®), a polyoleates, sodium laurate, sodium lauryl sulfate (sodium dodecyl sulfate), sodium oleate, sorbitan dilaurate, sorbitan dioleate, a sorbitan monolaurate, a sorbitan monooleate; sorbitan trilaurate, sorbitan trioleate, a sorbitan monopalmitate, a sorbitan stearate; a polyethylene glycol, a nonylphenyl ether, p-(1,1,3,3-tetramethylbutyl)-phenyl ether (Triton™ X-100), or a polysorbate (e.g., Tween®).

20. A method for treating rheumatoid arthritis or reducing a symptom of rheumatoid arthritis, the method comprising steps of:
(1) identifying a subject having rheumatoid arthritis or having a symptom thereof; and
(2) topically administering to the identified subject a transdermal formulation
wherein the transdermal formulation comprises a buffering agent in an amount that is effective in treating rheumatoid arthritis or reducing a symptom thereof, and
wherein the buffering agent comprises: sodium bicarbonate, sodium carbonate, a second carbonate salt, a second bicarbonate salt, TRIS, and/or lysine, and, optionally, comprises menthol and
wherein the amount of the buffering agent that is effective in treating rheumatoid arthritis or reducing a symptom thereof is from about 10% to about 56% w/w relative to the formulation; and
(3) administering an analgesic, an anti-inflammatory, a corticosteroid, or a nonsteroidal anti-inflammatory drug (NSAID), or a disease modifying anti-rheumatic agent (DMAR agent) before, contemporaneously with, or after administering the transdermal formulation, wherein the DMAR agent, when administered, is one or more of azathioprine, cyclosporin, gold, hydroxychloroquine, methotrexate, penicallamine, and sulphasalazine.

\* \* \* \* \*